United States Patent [19]

Matsuo et al.

[11] Patent Number: 4,771,045
[45] Date of Patent: Sep. 13, 1988

[54] 2-OXOZETIDINONE DERIVATIVES, THEIR PRODUCTION AND USE

[75] Inventors: Taisuke Matsuo, late of Ibaraki, by Michiko Matsuo, Takeshi Matsuo, Tazuko Matsuo, heirs; Michihiko Ochiai, Suita, both of Japan

[73] Assignee: Takeda Chemical Industries, Ltd., Osaka, Japan

[21] Appl. No.: 498,594

[22] Filed: May 26, 1983

[30] Foreign Application Priority Data

May 31, 1982 [JP] Japan .................................. 57-93462

[51] Int. Cl.$^4$ ................. A61K 31/395; A61K 31/425; C07D 205/08; C07D 417/12
[52] U.S. Cl. .................................... 514/210; 540/355
[58] Field of Search ........................ 260/245.4, 239 A; 540/355; 514/210

[56] References Cited

FOREIGN PATENT DOCUMENTS

| 53815 | 6/1982 | European Pat. Off. . |
| 0053816 | 6/1982 | European Pat. Off. . |
| 0061763 | 10/1982 | European Pat. Off. . |
| 0068466 | 1/1983 | European Pat. Off. . |
| 3225619 | 2/1983 | Fed. Rep. of Germany . |
| 57-131759 | 12/1982 | Japan . |
| 57-212179 | 12/1982 | Japan . |
| 82/01872 | 6/1982 | PCT Int'l Appl. . |

Primary Examiner—Mark L. Berch
Attorney, Agent, or Firm—Wenderoth, Lind & Ponack

[57] ABSTRACT

Novel 1-sulfo-2-oxoazetidine derivatives and their production and use.

These 1-sulfo-2-oxoazetidine derivatives exhibit excellent antimicrobial activity against gram-positive and gram-negative bacteria, and β-lactamase inhibitory activity, thus being of value as a prophylactic or therapeutic agent for infectious diseases in mammals.

3 Claims, No Drawings

2-OXOZETIDINONE DERIVATIVES, THEIR PRODUCTION AND USE

This invention relates to novel 2-oxoazetidine derivatives having antimicrobial activity or β-lactamase inhibitory activity.

Recently, a variety of 2-oxoazetidine derivatives have been synthesized. For example, it has been known that the reaction of a vinyl ester and chlorosulfonyl isocyanate gives a 4-acetoxy-2-oxoazetidine compound, into which a benzoyloxy, alkylthio or benzylthio group, for instance, can be introduced at the 4-position by nucleophilic substitution (Annalen der Chemie, 1974, 539). In this process, a compound having a chlorosulfonyl substituent at the 1-position is presumably formed as an intermediate, but the chlorosulfonyl group is easily eliminated, so that it is difficult to isolate such intermediate.

Furthermore, it has been reported that 1-sulfo-2-oxoazetidine having an alkyl substituent at 4-position of the azetidine ring is prepared, for example, by subjecting a corresponding 1-unsubstituted-2-oxoazetidine derivative to a sulfonation reaction (British laid open patent application No. 2,071,650), but production of 1-sulfo-2-oxoazetidines having substituents which are bonded with other atoms than carbon atom at 4-position of the azetidine ring has not been known.

The present inventors conducted intensive research for the purpose of obtaining novel and useful 2-oxoazetidine derivatives and found that 1-sulfo-2-oxoazetidine derivatives [I] as mentioned below show excellent antimicrobial activity against gram-positive and gram-negative bacteria, and β-lactamase inhibitory activity. Further research based on this finding has led to the present invention.

Thus, the present invention relates to: a compound of the formula:

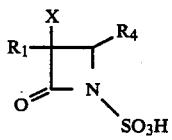
[I]

wherein $R_1$ is an amino group which may be acylated or protected; X is hydrogen or a methoxy group; $R_4$ is (1) a sulfamoyl group, (2) a group of the formula, —S—Y—Z where Y is an alkylene group of 1 to 3 carbon atoms or an alkenylene group of 2 to 3 carbon atoms, and Z is ① an alkanoyloxy group of 2 to 4 carbon atoms, ② a sulfocarbamoyl group, ③ an optionally protected carbamoyloxy group, ④ a sulfocarbamoyloxy group, or ⑤ an amino group which may be substituted by a sulfo group, an alkanoyl group of 2 to 4 carbon atoms or an aralkyloxycarbonyl group, (3) a triazolyl group which is bonded with the azetidine ring on a nitrogen atom of the triazol ring, which may be substituted by an alkoxycarbonyl group of 2 to 5 carbon atoms, or (4) an azido group, with a proviso that when $R_4$ is an azido group, $R_1$ is a group of the formula,

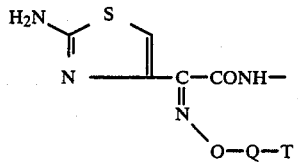

where Q is an alkylene group of 1 to 3 carbon atoms, and T is an optionally esterified carboxyl group; or a pharmaceutically acceptable salt or ester thereof.

Referring to the above formula, $R_4$ is (1) a sulfamoyl group, (2) a group of the formula, —S—Y—Z where Y is an alkylene group of 1 to 3 carbon atoms such as methylene, methylmethylene, dimethylmethylene, ethylmethylene, ethylene and methylethylene, or an alkenylene group of 2 to 3 carbon atoms such as vinylene and propenylene, and Z is ① an alkanoyloxy group of 2 to 4 carbon atoms such as acetoxy, propionyloxy and butyryloxy, ② a sulfocarbamoyl group, ③ an optionally protected carbamoyloxy group, the protective group being a haloacetyl group such as monochloroacetyl, dichloroacetyl and trichloroacetyl, ④ a sulfocarbamoyloxy group, or ⑤ an amino group which may be substituted by (a) a sulfo group, (b) an alkanoyl group of 2 to 4 carbon atoms such as acetyl, propionyl and butyryl, or (c) an aralkyloxycarbonyl group such as benzyloxycarbonyl and phenethyloxycarboyl, (3) a triazolyl group (e.g. 1,2,3-triazolyl, 1,2,4-triazolyl) which is bonded with the azetidine ring on a nitrogen atom of the triazol ring, which may be substituted by an alkoxycarbonyl group of 2 to 5 carbon atoms such as methoxycarbonyl, ethoxycarbonyl, propoxycarbonyl, butoxycarbonyl, sec-butoxycarbonyl and tert-butoxycarbonyl, or (4) an azido group, with a proviso that when $R_4$ is an azido group, $R_1$ is a group of the formula,

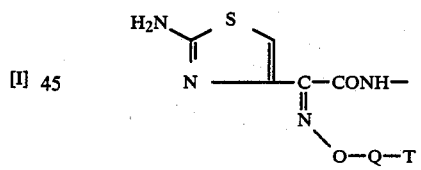

where Q is an alkylene group of 1 to 3 carbon atoms, such as methylene, methylmethylene, dimethylmethylene, ethylmethylene, ethylene and methylethylene, and T is an optionally esterified carboxyl group, the ester residue being a lower alkyl group of 1 to 3 carbon atoms (e.g. methyl, ethyl, propyl) which may optionally be substituted by a trimethylsilyl group.

Preferably, $R_4$ is (1) a group of the formula, —S—Y—Z where Y is an alkylene group of 1 to 3 carbon atoms, Z is an alkanoyloxy group of 2 to 4 carbon atoms, an optionally protected carbamoyloxy group, or an amino group which may be substituted by an aralkyloxycarbonyl group, (2) triazolyl group which is bonded with the azetidine ring on a nitrogen atom of the triazol ring, which may be substituted by an alkoxycarbonyl group of 2 to 5 carbon atoms, and (3) an azido group, with a proviso that when $R_4$ is an azido group, $R_1$ is a group of the formula,

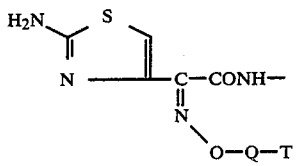

where Q is an alkylene group of 1 to 3 carbon atoms, and T is an optionally esterified carboxyl group.

Referring to a group of the formula, —S—Y—Z represented by $R_4$, preferably Y is a methylene or ethylene group and Z is an acetoxy group, a carbamoyloxy group, or a sulfocarbamoyloxy group.

A group of the formula:

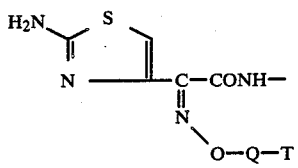

represented by $R_1$ when $R_4$ is an azido group, includes, among others, 2-[1-(1-carboxy-1-methylethoxyimino]-2-(2-aminothiazol-4-yl)acetyl, 2-(2-aminothiazol-4-yl)-2-[1-(2-trimethylsilylethoxycarbonyl)-1-methylethoxyimino]acetyl and 2-(2-aminothiazol-4-yl)-2-[(carboxy)-methoxyimino]acetyl.

The acyl moiety of the acylated amino group $R_1$ may be one of the acyl substituent on 6-amino group of known penicillin derivatives or on 7-amino group of known cephalosporin derivatives. As examples of such acyl groups, there may be mentioned.

(1) a group of the formula:

wherein $R_6$ is a lower alkyl, a phenyl which may optionally be substituted, a heterocyclic group which may optionally be substituted or a benzoyl which may optionally be substituted, (2) a group of the formula:

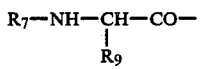

wherein $R_7$ is hydrogen, an amino acid residue which may optionally be substituted, an amino-protecting group, a group of the formula, $R_8$—$(CH_2)_{n1}$—CO— [where $R_8$ is hydrogen, a heterocyclic group which may optionally be substituted, phenyl which may optionally be substituted, a lower alkyl which may optionally be substituted, a phenylthio which may optionally be substituted, a lower alkylthio, carboxyl or carbamoyl, n1 is 0, or an integer of 1 to 4; and the —$(CH_2)_{n1}$— group may be substituted], a group of the formula,

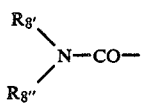

[where $R_{8'}$ and $R_{8''}$ may be the same or different and each is hydrogen, a lower alkyl, a lower alkylcarbamoyl, phenylcarbonyl which may optionally be substituted or sulfo] or a group of $R_{8'''}$—$SO_2$— [where $R_{8'''}$ is a lower alkyl which may optionally be substituted]; $R_9$ is hydrogen, a lower alkyl which may optionally be substituted, a phenyl which may optionally be substituted, a heterocyclic group which may optionally be substituted, a cycloalkenylene, a heterocycle-carbonylamino which may optionally be substituted or be interrupted by an alkylene group, (3) a group of the formula:

wherein $R_{10}$ is a group of the formula,

[where X is oxygen or sulfur, $R_{12}$ is a heterocyclic group which may optionally be substituted or a phenyl which may optionally be substituted, $R_{13}$ is hydrogen, a phenyl which may optionally be susbtituted, a lower acyl group which may optionally be substituted or a lower alkyl which may optionally be substituted, or a group of the formula, —$R_{14}$—$R_{15}$ (where $R_{14}$ is a lower alkylene or lower alkenylene $R_{15}$ is carboxyl, an ester thereof or a heterocyclic group)]: $R_{11}$ is a mere single bond or a group of the formula,

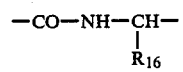

(where $R_{16}$ is a lower alkyl, a phenyl which may optionally be susbtituted or a heterocyclic group which may optionally be substituted), (4) a group of the formula:

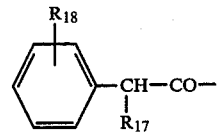

wherein $R_{17}$ is hydroxyl, hydroxysulfonyloxy, carboxyl, a sulfamoyl which may optionally be substituted, sulfo, a phenoxycarbonyl which may optionally be substituted, benzyloxycarbonyl, formyloxy, phthalimino, azido or a halogen; $R_{18}$ is hydrogen, a lower alkyl, a lower alkoxy, a halogen, azido, nitro or hydroxyl, or (5) a group of the formula:

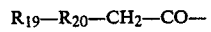

wherein $R_{19}$ is cyano, a phenyl which may optionally be substituted, a phenoxy which may optionally be substituted, a lower alkyl which may optionally be substituted, an alkenylene which may optionally be substituted, or a heterocyclic group which may optionally be substituted; $R_{20}$ is a mere single bond or —S—.

The lower alkyl group $R_6$ preferably contains 1 to 6 carbon atoms. The heterocyclic moiety of the optionally substituted heterocyclic group $R_6$ is a 5- or 6-membered heterocyclic group including 1 to 2 nitrogen atoms, which may optionally include one oxygen atom. Examples of such heterocyclic group include isoxazolyl, piperazinyl, imidazolinyl, etc. The substituents on such heterocyclic groups may for example be a lower alkyl group of 1 to 3 carbon atoms, a lower alkoxy group of 1 to 3 carbon atoms, a halogen, nitro, amino, oxo, thioxo, or a phenyl group which may optionally be substituted. The substituents on the optionally substituted benzoyl group and those on said optionally substituted phenyl group may for example be a lower alkyl group of 1 to 3 carbon atoms, a lower alkoxy group of 1 to 3 carbon atoms, a halogen, nitro, amino or the like.

The amino acid residue for the optionally substituted amino acid residue $R_7$ may for example be glycyl, alanyl, valyl, leucyl, isoleucyl, seryl, threonyl, cystinyl, cystyl, methionyl, α- or β-aspartyl, α- or γ-glutamyl, lysyl, arginyl, phenylalanyl, phenylglycyl, tyrosyl, histidyl, tryptophyl, prolyl, etc. The substituents that may be present on such amino acid residues may for example be amino, a lower alkylamino, an amino-protecting group, carbamoyl, methylcarbamoyl, sulfamoyl, benzyl, 4-ethyl-2,3-dioxo-1-piperazinecarbonyl, 4-ethyl-2,3-dioxo-1-piperazinecarbonylamino, etc. The lower alkyl moiety of said lower alkylamino preferably contains 1 to 3 carbon atoms. The protective group on this amino group may be one of those amino-protecting groups mentioned hereinafter.

The amino-protecting group $R_7$ may be one of those amino-protecting groups mentioned hereinafter.

The heterocyclic moiety of the optionally substituted heterocyclic group $R_8$ in a group of the formula, $R_8-(CH_2)_{n'}-CO-$ may for example be a 5- or 6-membered heterocyclic group including one sulfur, nitrogen or oxygen atom, a 5- to 6-membered heterocyclic group including 2 to 4 nitrogen atom, or a 5- to 6-membered heterocyclic group including 1 to 2 nitrogen and one sulfur or oxygen atom, and these heterocyclic groups may each be fused to a 6-membered cyclic group including not more than 2 nitrogen atoms, a benzene ring or a 5-membered cyclic group including one sulfur atom.

Examples of the heterocyclic group $R_8$ include 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthylidinyl, 1,5-naphthylidinyl, 1,6-naphthylidinyl, 1,7-naphthylidinyl, 2,7-naphthylidinyl, 2,6-naphthylidinyl, quinolyl, thieno[2,3-b]pyridinyl, tetrazolyl, thiadiazolyl, oxadiazolyl, triazinyl, thienyl, pyrrolyl, furyl, etc.

The substituents on the optionally substituted heterocyclic group $R_8$ may for example be a substituted or unsubstituted alkyl group of 1 to 12 carbon atoms, a lower alkoxy group of 1 to 3 carbon atoms, hydroxyl, oxo, thioxo, aldehyde, trifluoromethyl, amino, a halogen, a lower ($C_{1-3}$) alkylsulfonyl, 2,6-dichlorophenyl, coumarin-3-carbonyl, 4-formyl-1-piperazinyl, pyrrolaldoimino, furanaldoimino, 2-thiophenaldoimino, 3-thiophenaldoimino, mesyl, an amino-protecting group, a($C_{2-4}$) acylamino which may be substituted by a halogen. The amino-protecting groups may be those mentioned hereinafter. The substituents optionally present on said ($C_{1-12}$) alkyl groups may for example be phenyl, a halogen, hydroxyl, a dialkylamino, etc. The alkyl moiety of said dialkylamino is preferably a lower ($C_{1-3}$) alkyl.

The substituents on the optionally substituted phenyl $R_8$ may for example be a lower alkyl group of 1 to 3 carbon atoms, a lower alkoxy group of 1 to 3 carbon atoms, a halogen, hydroxyl, amino, etc.

As the lower alkyl which may be substituted $R_8$, there may be mentioned an alkyl whose carbon number ranges 1 to 3. The substituent in the optionally substituted lower alkyl includes carboxyl, amino, ureido, carbamoyl, etc.

The lower alkyl moiety of lower alkylthio $R_8$ preferably contains 1 to 3 carbon atoms. The substituents on an optionally substituted phenylthio $R_8$ may, for example be a lower ($C_{1-3}$) alkyl, a lower ($C_{1-3}$) alkoxy, a halogen, hydroxyl, amino, etc. The substituents which may be present on the group of the formula, $-(CH_2)_{n'}-$ may for example be amino, a group of the formula, $-NH-CO-R_8''''$ [wherein $R_8''''$ is amino or a substituted or unsubstituted piperazinyl group]. The substituents on the optionally substituted piperazinyl group $R_8''''$ may for example be a lower ($C_{1-3}$) alkyl, a lower ($C_{1-3}$) alkoxy, hydroxyl, oxo, thioxo, a halogen, etc.

The lower alkyl group $R_8'$ and/or $R_8''$ preferably contain 1 to 3 carbon atoms. The lower alkyl moiety of said lower alkylcarbamoyl is preferably a group of 1 to 3 carbon atoms. The substituents on the optionally substituted phenylcarbonyl group may for example be a lower ($C_{1-3}$) alkyl, a lower ($C_{1-3}$) alkoxy, a halogen, hydroxyl, hydroxysulfonyloxy, benzyloxy, etc.

The lower alkyl moiety of said optionally substituted lower alkyl group $R_8'''$ in a group of the formula, $R_8'''-SO_2-$ preferably contains 1 to 6 carbon atoms and the substituents may be present in one or two positions and may for example be amino, carboxyl, benzyloxycarbonyl, a protected amino, etc.

The lower alkyl moiety of the optionally substituted lower alkyl $R_9$ preferably contains 1 to 3 carbon atoms, the substituents being, for example, hydroxyl, formyloxy, phenyl, carbamoyl, methylcarbamoyl, methylthio, thienylacetamido, ethoxycarbonylmethylcarbamoyl, N-methyltetrazolylthio, a halogen, sulfamoyl, etc.

The substituents on optionally substituted phenyl $R_9$ may for example be a lower ($C_{1-3}$) alkyl, a lower ($C_{1-3}$) alkoxy, a halogen, hydroxyl, hydroxysulfonyloxy, benzyloxy, benzoyloxy, trimethylsilyl, a ($C_{2-10}$) alkylcarbonylamino etc.

The heterocyclic moiety of optionally substituted heterocyclic group $R_9$ includes among others a five-membered heterocyclic group containing one sulfur, nitrogen or oxygen atom, a five-membered heterocyclic group containing 1 to 2 nitrogen atoms and one sulfur or oxygen atom, and 5- or 6-membered hererocyclic groups containing 2 to 4 nitrogen atoms. Examples of such heterocyclic group are thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl, oxadiazolyl, etc. The substituents on said heterocyclic group include among others a lower ($C_{1-3}$) alkyl, a lower ($C_{1-3}$) alkoxy, a halogen, hydroxyl, nitro, hydroxysulfonyloxy, amino, and a ($C_{2-4}$) alkylcarbonylamino which may be substituted by a halogen.

The cycloalkenylene $R_9$ preferably has a 5- or 6-membered ring, and is, for example, cyclohexenyl or cyclohexadienyl.

The heterocyclic moiety of the heterocycle-carbonylamino group $R_9$ which may be substituted and/or interrupted by an alkylene chain may be a 6-membered heterocyclic group containing two nitrogen atoms and is, for example piperazinyl, which may have such a substituent as a ($C_{1-12}$) alkyl, a lower ($C_{1-3}$) alkoxy, oxo, thioxo or amino. The alkylene chain preferably contains 1 to 3 carbon atoms, and is, for example, methylene, ethylene or n-propylene.

The heterocyclic moiety of the optionally substituted heterocyclic group $R_{12}$ in the formula

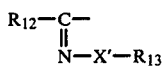

(or $R_{10}$) may be a 5-membered heterocyclic group containing one nitrogen, sulfur or oxygen atom with or without one nitrogen atom. Examples of such heterocyclic group are 2-thiazolyl, 4-thiazolyl, 5-thiazolyl, 2-thienyl, 3-thienyl, 2-furyl, 3-furyl, 2-pyrrolyl and 3-pyrrolyl. The substituents on these heterocyclic groups include among others a lower ($C_{1-3}$) alkyl, a lower ($C_{1-3}$) alkoxy, hydroxyl, mesyl, a halogen, imino, amino, mesylamino, and a ($C_{2-4}$) alkylcarbonylamino which may be substituted by a halogen.

The substituent moiety of the optionally substituted phenyl $R_{12}$ includes a lower ($C_{1-3}$) alkyl, a lower ($C_{1-3}$) alkoxy, a halogen, nitro, amino, hydroxyl, a substituted hydroxyl. The substituent in said substituted hydroxyl is, for example, benzyl, benzoyl, a ($C_{2-10}$) alkylcarbonyl, γ-D-glutamyl or 3-amino-3-carboxypropyl.

The lower alkyl moiety of the optionally substituted lower alkyl $R_{13}$ preferably contains 1 to 3 carbon atoms. The substituents on the optionally substituted lower alkyl $R_{13}$ includes carbamoyl, a halogen, etc.

The substituents on the optionally substituted phenyl $R_{13}$ includes a lower ($C_{1-3}$) alkyl, a lower ($C_{1-3}$) alkoxy, a halogen, etc.

With regard to the optionally substituted lower alkylcarbonyl $R_{13}$, the lower alkylcarbonyl preferably contains 2 to 4 carbon atoms, and the substituent is, for example, a halogen.

The lower alkylene $R_{14}$ in the formula, $-R_{14}-R_{15}$ (i.e. $R_{13}$) preferably contains 1 to 3 carbon atoms, and is for example methylene, dimethylmethylene, ethylmethylene, ethylene or methylethylene.

The lower alkenylene $R_{14}$ preferably contains 2 to 3 carbon atoms, and is for example vinylene or propenylene.

As examples of the carboxylate ester group $R_{15}$, there may be mentioned methyl, ethyl, propyl, t-butyl, p-nitrobenzyl, 2-trimethylsilylethyl and t-butyldiphenylsilyl, and diphenylmethyl esters.

The heterocyclic group $R_{15}$ may be a 6-membered one containing one nitrogen atom and one oxygen atom, or a 5-membered one containing 3-4 nitrogen atoms. Morpholino, tetrazolyl and triazolyl are the examples.

The lower alkyl $R_{16}$ in a group of the formula,

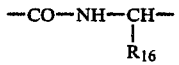

(or $R_{11}$) preferably contains 1 to 3 carbon atoms.

The substituent in the optionally substituted phenyl $R_{16}$ includes a lower ($C_{1-3}$) alkyl, a lower ($C_{1-3}$) alkoxy, a halogen, nitro, amino, a ($C_{2-10}$) alkylcarbonyloxy, etc.

The heterocyclic moiety of the optionally substituted heterocyclic group $R_{16}$ is, for example, a 5-membered heterocyclic group containing one sulfur, nitrogen or oxygen atom, a 5-membered heterocyclic group containing 1 to 2 nitrogen atoms and one sulfur or oxygen atom, or a 5-membered heterocyclic group containing 2 to 4 nitrogen atoms. Examples of such heterocyclic group are thiazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl. The substituents on these include a lower ($C_{1-3}$) alkyl, a lower ($C_{1-3}$) alkoxy, a halogen, hydroxyl, amino, hydroxyl, amino, a ($C_{2-4}$) alkylcarbonylamino which may be substituted by a halogen.

The substituents on the optionally substituted sulfamoyl $R_{17}$ may be, for example, a lower ($C_{1-3}$) alkyl.

The substituents on the optionally substituted phenoxycarbonyl $R_{17}$ may be, for example, a lower ($C_{1-3}$) alkyl or a lower ($C_{1-3}$) alkoxy.

The lower alkyl or lower alkoxy $R_{18}$ preferably contains 1 to 3 carbon atoms.

The substituents on the optionally substituted phenyl $R_{19}$ may be for example, a lower ($C_{1-3}$) alkyl, a lower ($C_{1-3}$) alkoxy, a halogen, nitro, amino, hydroxyl or a substituted aminomethyl. The substituents on said substituted aminomethyl include among others carbamoyl, (2-oxo-3-benzylideneaminoimidazolidin-1-yl)carbonyl and (2-oxo-imidazolidin-1-yl)carbonyl.

The substituents on the optionally substituted phenoxy $R_{19}$ may be, for example, a lower ($C_{1-3}$) alkyl, a lower ($C_{1-3}$) alkoxy, a halogen, nitro, amino, hydroxy or aminomethyl. The substituents are as mentioned above for the substituent on the optionally substituted phenyl $R_{19}$. The optionally substituted lower alkyl $R_{19}$ preferably contains 1 to 6 carbon atoms, and the substituents may be, for example, a halogen, hydroxyl, cyano or trifluoromethyl.

The alkenylene in the optionally substituted alkenylene $R_{19}$ is, for example, vinylene or propenylene, and the substituents may be, for example, carboxyl or cyano.

The heterocyclic moiety in the optionally substituted heterocyclic group $R_{19}$ may be a 5- or 6-membered one containing one sulfur atom or 1 to 4 nitrogen atoms, or a 5- or 6-membered one containing one suflur atom and one nitrogen or oxygen atom. Examples of the heterocyclic group are 2-thienyl, benzothienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiin.

The substituents of the optionally substituted heterocyclic group $R_{19}$ may be, for example, a lower ($C_{1-3}$) alkyl, a lower ($C_{1-3}$) alkoxy, a halogen, nitro, hydroxyl, an optionally protected amino, carboxyl, oxo, a ($C_{2-4}$) alkylcarbonylamino which may be substituted by a halogen, or ($C_{2-4}$) alkylcarbonyl.

Among the terms as used hereinabove in relation to the acyl groups or moieties, the ($C_{1-12}$) alkyl includes, among others, methyl, trifluoromethyl, ethyl, n-propyl, isopropyl, n-butyl, isobutyl, sec-butyl, tert-butyl, pentyl, isopentyl, hexyl, isohexyl, heptyl, 3-heptyl, octyl, nonyl, decyl, undecyl, dodecyl and cyclohexyl. The lower ($C_{1-6}$) alkyl includes, among others, methyl, trifluoromethyl, ethyl, n-propyl, isopropyl, n-butyl, isobutyl, sec-butyl, tert-butyl, pentyl, isopentyl, hexyl and isohexyl. The lower ($C_{1-3}$) alkyl includes, among others, methyl, trifluoromethyl, ethyl, n-propyl and isopropyl. The lower ($C_{1-3}$) alkoxy includes methoxy, ethoxy, n-propoxy and isopropoxy.

Examples of the halogen mentioned in relation to the above formulas are fluorine, chlorine, bromine and iodine. Examples of the lower ($C_{1-3}$) alkylsulfonyl are methylsulfonyl, ethylsulfonyl, n-propylsulfonyl and isopropylsulfonyl. Examples of the ($C_{2-4}$) alkylcarbonylamino are acetylamino, propionylamino, n-butyrylamino and isobutyrylamino. Examples of the ($C_{2-10}$) alkylcarbonyloxy are acetoxy, n-propionyloxy, n-butyryloxy, isobutyryloxy, n-pentanoyloxy, n-hexanoyloxy, n-heptanoyloxy, n-octanoyloxy, n-nonanoyloxy and n-decanoyloxy.

Relative to the above-mentioned acyl groups, examples of the acyl of the formula $R_6$—CO— ($R_6$ being as above defined) are 3-(2,6-dichlorophenyl)-5-methylisoxazol-4-ylcarbonyl, 4-ethyl-2,3-dioxo-1-piperazinecarbonyl and 2-oxomidazolidin-1-yl-carbonyl.

Examples of the acyl group of the formula

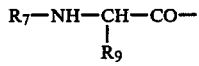

($R_7$ and $R_9$ being as above defined) are D-alanyl, D-phenylalanyl, α-benzyl-N-carbobenzoxy-γ-D-gultamyl-D-alanyl, D-phenylglycyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoyltryptophyl-D-phenylglycyl, N-[2-amino-3-(N-methylcarbamoyl)propionyl]-D-phenylglycyl, D-N-[2-carbobenzoxyamino-3-(N-methylcarbamoyl)propionyl]-D-phenylglycyl, N-carbobenzoxy-D-phenylglycyl-D-phenylglycyl, 2-(2,3-diaminopropionamideo)-2-phenylacetyl, D-alanyl-D-alanyl, 2-[2-amino-3-(N-methylcarbamoyl)propionamido]acetyl, 2-(2-amino-3-sulfamoylpropionamido)-2-phenylacetyl, 2-[2-amino-3-(4-ethyl-2,3-dioxo-1-piperazinecarboxamido)propionamido]-2-phenylacetyl, D-2-(4-ethyl-2,3-dioxo-1-piperazinecarboxamido)-2-(4-methoxyphenyl)acetyl, D-2-[2-(4-ethyl-2,3-dioxo-1-piperazinecarboxamido)-3-(N-methylcarbamoyl)propionamido]-2-phenylacetyl, D-2-[2-(4-ethyl-2,3-dioxo-1-piperazinecarboxamido)acetamido]-2-phenylacetyl, D-2-(3-sulfamoyl-2-benzyloxycarboxamidopropionamido)-2-phenylacetyl, D-2-[2-benzyloxycarboxamido-3-(4-methoxyphenyloxycarboxamido)propionamido]-2-phenylacetyl, 2-[2-benzyloxycarboxamido-3-(N-methylcaarbamoyl)propionamido]acetyl, 2-(N-carbobenzoxy-D-phenylglycylamino)-3-(N-methylcarbamoyl)propionyl)propionyl, N-carbobenzoxy-D-alanyl, 2-benzyloxy-carboxamido-3-(N-methylcarbamoyl)propionyl, D-2-(4-ethyl-2,3-dithioxo-1-piperazinecarboxamido)-2-phenylacetyl, 2-(2-aminothiazol-4-yl)-2-(4-ethyl-2,3-dioxo-1-piperazinecarboxamido)acetyl, 2-(2-phenylacetamido)propionyl, 2-(4-ethyl-2,3-dioxo-1-piperazinecarboxamido)-2-thienylacetyl, D-2-(4-n-dodecyl-2,3-dioxo-1-piperazinecarboxamido)-2-phenylacetyl, D-2-(4,6-dienyl-2,3-dioxo-1-piperazinecarboxamido)-2-phenylacetyl, D-2-(4-cyclohexyl-2,3-dioxo-1-piperazinecarboxamido)-2-phenylacetyl, D-2-(4-cyclohexyl-2,3-dioxo-1-piperazinecarboxamido)-2-thienylacetyl, D-2-(4-n-amyl-6(S)-methyl-2,3-dioxo-1-piperazinecarboxamido)-2-thienylacetyl, D-2-(4-ethyl-5(R)-methyl-2,3-dioxo-1-piperazinecarboxamido)-2-thienylacetyl, D-2-(4-ethyl-5(S)-methyl-2,3-dioxo-1-piperazinecarboxamido)-2-thienylacetyl, 2-(8-hydroxy-1,5-naphthyridine-7-carboxamido)-2-phenylacetyl, 2-(4-n-octyl-2,3-dioxo-1-piperazinecarboxamido)-2-phenylacetyl, 2-(4-ethyl-2,3-dioxo-1-piperazinecarboxamido)-2-(4-hydroxysulfonyloxyphenyl)acetyl, 2-(4-ethyl-2,3-dioxo-1-piperazinecarboxamido)-2-(4-chlorophenyl)acetyl, 2-(4-n-octyl-2,3-dioxo-1-piperazinecarboxamido)-2-(4-hydrosulfonyloxyphenyl)acetyl, 2-(4-ethyl-2,3-dioxo-1-piperazinecarboxamido)-2-(4-trimethylsilylphenyl)acetyl, 2-(4-ethyl-2,3-dioxo-1-piperazinecarboxamido)-2-(3-chloro-4-methoxyphenyl)acetyl, 2-(4-ethyl-2,3-diox-o-1-piperazinecarboxamido)-2-(3-chloro-4-hydroxysulfonyloxyphenyl)acetyl, 2-(4-ethyl-2,3-dioxo-1-piperazinecarboxamido)-2-(3-chloro-4-hydroxyphenyl)acetyl, 2-(4-ethyl-2,3-dioxo-1-piperazinecarbonyl)-2-(4-benzyloxyphenyl)acetyl, 2-(4-n-octyl-2,3-dioxo-1-piperazinecarboxamido)-2-(4-hydroxyphenyl)acetyl, α-[N-(4-ethyl-2,3-dioxo-1-piperazinecarbonyl]glutaminyl, N-(4-ethyl-2,3-dioxo-1-piperazinecarbonyl)-phenylalanyl, N-(4-ethyl-2,3-dioxo-1-piperazinecarbonyl)-D-alanyl, 2-(4-ethyl-2,3-dioxo-1-piperazinecarboxamido)-2-(4-hydroxyphenyl)acetyl, 2,2-bis(4-ethyl-2,3-dioxo-1-piperazinecarboxamido)acetyl, 2-(4-ethyl-2,3-dioxo-1-piperazinecarboxamido)-2-(1-cyclohexen-1-yl)acetyl, 2-(4-n-octyl-2,3-dioxo-1-piperazinecarboxamido)-2-thienylacetyl, 2-(4-ethyl-2,3-dioxo-1-piperazinecarboxamido)-2-(2-chloroacetamidothiazol-4-yl)acetyl, 2-(4-ethyl-2,3-dioxo-1-piperazinecarboxamido)-2-(2-methylthiazol-4-yl)acetyl, 2-(4-ethyl-2,3-dioxo-1-piperazinecarboxamido)-2-(2-acetamidothiazol-4-yl)acetyl, 2-(4-n-octyl-2,3-dioxo-1-piperazinecarboxamido)-2-(2-aminothiazol-4-yl)acetyl, 2-(4-ethyl-2,3-dioxo-1-piperazinecarboxamido)-2-furylacetyl, 2-(4-ethyl-2,3-dioxo-1-piperazinecarboxamido)-2-(2-pyrrolyl)acetyl, 2-(4-ethyl-2,3-dithioxo-1-piperazinecarboxamido)-2-(4-hydroxyphenyl)acetyl, 2-(4-n-octyl-2,3-dioxo-1-piperazinecarboxamido)-2-(2-chloroacetamidothiazol-4-yl)acetyl, N-(4-ethyl-2,3-dioxo-1-piperazinecarbonyl)-D-methionyl, D-2-[4-(2-phenylethyl)-2,3-dioxo-1-piperazinecarboxamido]phenylacetyl, D-2-(4-ethyl-2,3-dioxo-1-piperazinecarboxamido)-2-(4-benzoyloxyphenyl)acetyl, 2,5-bis(4-ethyl-2,3-dioxo-1-piperazinecarboxamido)pentanoyl, 2-(4-ethyl-2,3-dioxo-1-piperazinecarboxamido)-3-(N-methylcarbamoyl)-propionyl, 2,3-bis(4-ethyl-2,3-dioxo-1-piperazinecarboxamido)propionyl, 2-(4-ethyl-2,3-dioxo-1-piperazinecarboxamido)-3-chloropropionyl, 2-(4-ethyl-2,3-dioxo-1-piperazinecarboxamido)-2-(4-n-octanoyloxyphenyl)acetyl, 2-(4-ethyl-2,3-dioxo-1-piperazinecarboxamido)-3-sulfamoylpropionyl, 3-[2-(4-ethyl-2,3-dioxo-1-piperazinecarboxamido)]-3-[(1-methyl-1H-tetrazol-5-yl)thio]propionyl, 2-(4-ethyl-2,3-dioxo-1-piperazinecarboxamido)acetyl, D-2-[4-(2-hydoxyethyl)-2,3-dioxo-1-piperazinecarboxamido]-2-phenylacetyl, D-2-[4-(2-chloroethyl)-2,3-dioxo-1-piperazinecarboxamido]-2-phenylacetyl, 2-(4-ethyl-2,3-dioxo-1-piperadinecarboxamido)-3-(ethoxycarbonylmethylcarbamoyl)propionyl, 2-(4-ethyl-2,3-dioxo-1-piperazinecarboxamido)-3-(thienylacetamido)propionyl, 2-(4-ethyl-2,3-dioxo-1-piperazinecarboxamido)-3-[2-(1H-tetrazol-1-yl)acetamido]propionyl, 2-(4-ethyl-2,3-dioxo-1-piperazinecarboxamido)-2-(1H-tetrazol-1-yl)acetyl, 2-[(3-furfurlylideneamino-2-oxoimidazolidin-1-yl)carboxamiodo]-2-phenylacetyl, 2-[(3-furfurylideneamino-2-oxoimidazolidin-1-yl)carboxamido]-2-(4-hydroxphenyl)acetyl, 2-[(3-furfurylideneamino-2-oxoimidazolidin-1-yl)carboxamido]-2-(4-hydroxysulfonyloxyphenyl)acetyl, 2-[[2-oxo-3-(thiophene-2-aldoimino)-imidazolidin-1-yl]carboxamido]-2-phenylacetyl, 2-[(3-furfurylideneamino-2-oxoimidazolidin-1-yl)carboxamido]-2-thienylacetyl, D-2-[(3-methylsulfonyl-2-oxoimidazolidin-1-yl)carboxamido]-2-phenylacetyl, 2-[(3-furfurylideneamino-2-oxoimidazolidin-1-yl)carboxamido]-2-(2-aminothiazol-4-yl)acetyl, 2-[(3-furfurylideneamino-2-oxoimidazolidine-1-yl)carboxamido]-2-(2-chloroacetamidothiazol-4-yl)acetyl, 2-[(2-oxo-3-(thiophene-2-aldoimino)imidazolidin-1-yl]-carboxamido]-2-thienylaceytl, 2-[(3-mesyl-2-oxoimidazolidin-1-yl)carboxamido]-2-thienylacetyl, D-2-[(3-furfurylideneamino-2-oxoimidazolidin-1-yl)carboxamido]propionyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, D-3-[(2-oxo-3-sulfoimidazolidin-1-yl)carboxamido]-2-thienylacetyl, D-2-[(5-methoxycarbonyl-3-methyl-2-oxoimidazolidin-1-yl)carboxamido]-2-phenylacetyl, D-2-[(5-benzyloxycarbonyl-3-methyl-2-oxoimidazolidin-1-yl)carboxamido]-2-phenylacetyl, D-2-[(5-carboxyl-3-methyl-2-oxoimidazolidin-1-yl)carboxamido]-2-phenylacetyl, 2-(coumarin-3-carboxamido)-2-phenylacetyl, 2-(4-ethyl-2,3-dioxo-1-piperazinecarboxamido)-2-(2-chloro-1-cyclohexen-1-yl)acetyl, D-2-(4-n-amyl-2,3-dioxo-1-piperazinecarboxamido)-2-phenylacetyl, D-2-(4-n-amyl-6(R)-methyl-2,3-dioxo-1-piperazinecarboxamido)-2-thienylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-aminothiazol-4-yl)acetyl]-D-phenylglycyl, 2-(6-bromo-1-ethyl-1,4-dihydro-4-oxothieno[2,3-b]pyridine-3-carboxamido)-2-phenylacetyl, 2-[2-(2-chloroacetamidothiazol-4-yl)acetamido]-2-phenylacetyl, 2-(2,5-dioxo-1,2,4-triazino-6-carboxamido)-2-thienylacetyl, 2-(2,4-dioxopyrimidino-5-carboxamido)-2-thienylacetyl, 2-[2-(4-ethyl-2,3-dioxo-1-piperazinecarboxamido)-2-thienylacetamido]-2-phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxypropylamino)-2-furylacetyl, α-(thienylmethylcarbonyl)alanyl, 2-(4-chlorobenzoylureido)-2-thienylacetyl, 2-(2-thienylacetamido)acetyl, N-benzyloxycarboxamido-D-alanyl, N-(4-hydroxybenzoyl)-D-alanyl, 2-(4-chlorobenzamido)propionyl, 2-(4-aminobenzamido)acetyl, N-(4-ethyl-2,3-dioxo-1-piperazinecarbonyl)methionyl-D-phenylglycyl, D-2-[[3-(2,6-dichlorophenyl)-5-methylisoxazol-4-yl]carboxamido]-2-thienylacetyl, 2-ureido-2-thienylacetyl, N-carbamoyl-D-phenylglycyl, 2-(3-methylcarbamoyl-3-methyl-1-ureido)-2-phenylacetyl, 2-(3-methylcarbamoyl-3-methyl-1-ureido)-2-(4-hydroxyphenyl)acetyl, 2-(3-methylcarbamoyl-3-methyl-1-ureido)-2-thienylacetyl, 2-[3-(2-hydroxybenzoyl)-1-ureido]-2-phenylacetyl, 2-[3-(2-benzyloxybenzoyl)-1-ureido]-2-(4-hydroxysulfonyloxyphenyl)acetyl, 2-[3-(2-hydroxybenzoyl)-1-ureido]-2-(4-hydroxyphenyl)acetyl, 2-[3-(2-benzyloxybenzoyl)-1-ureido]-2-phenylacetyl, 2-[3-(2-benzyloxybenzoyl)-1-ureido]-2-(4-hydroxyphenyl)acetyl, D-2-[2-(benzyloxycarboxamido)-2-(benzyloxycarbonyl)ethanesulfonamido]-2-phenylacetyl, N-mesyl-D-phenylglycyl, 2-(2-aminothiazol-4-yl)-2-ureidoacetyl, 2-(2-aminothiazxol-4-yl)-2-formamidoacetyl, 2-(2-aminothiazol-4-yl)-2-acetamidoacetyl, 2-(2-aminothiazol-4-yl)-2-[(1-carboxy-1-methylethoxy)imino]acetyl, 2-(2-aminothiazol-4-yl)-2-pivalamidoacetyl, 2-(2-aminothiazol-4-yl)-2-(3-methyl-1-ureido)acetyl, 2-(2-aminothiazol-4-yl)-2-[(2-methoxycarbonyl-2-methylpropion)amido]acetyl, 2-(2-aminothiazol-4-yl)-2-[2-(methoxycarbonyl)acetamido]acetyl, 2-(2-aminothiazol-4-yl)-2-[[3-(3-thienylidene)amino-2-oxoimidazolidin-1-yl]carboxamido]acetyl, 2-thienyl-2-[[3-(3-thienylidene)amino-2-oxoimidazolidin-1-yl]carboxamido]acetyl, 2-(2-aminothiazol-4-yl)-2-(oxamoylamino)acetyl 2-(2-aminothiazol-4-yl)-2-(methoxyalylamino)acetyl, 2-(2-aminothiazol-4-yl)-2-(oxaloamino)acetyl, D-2-(4-ethyl-2,3-dioxo-1-piperazinecarboxamido)-3-(S)-formyloxybutyryl, D-2-(4-ethyl-2,3-dioxo-1-piprazinecarboxamido)-3-(S)-hydroxybutyryl etc.

Examples of the acyl group of the formula $R_{10}$—$R_{11}$—CO— ($R_{10}$ and $R_{11}$ being as above defined) are N-[2-(2-aminothiazol-4-yl)-2-methoxyiminoacetyl]-D-alanyl, N-[2-(2-aminothiazol-4-yl)-2-methoxyiminoacetyl]-D-phenylglycyl, 2-(2-aminothiazol-4-yl)-2-(2-aminothiazol-4-yl)-2-methoxyiminoacetamido]acetyl, 2-(2-chloroacetamidothiazol-4-yl)-2-[2-(2-chloracetamidothiazol-4-yl)-2-methoxyiminoacetamido]acetyl, 2-(2-chloroacetamidothiazol-4-yl)-2-methoxyiminoacetyl, 2-(2-aminothiazol-4-yl)-2-isopropoxyiminoacetyl, 2-(2-aminothiazol-4-yl)-2-methoxyiminoacetyl, 2-(2-aminothiazol-4-yl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-dichloroacetyloxyiminoacetyl, 2-[4-(γ-D-glutamyloxy)phenyl]-2-oxyiminoacetyl, 2-[4-(3-amino-3-carboxypropoxy)phenyl]-2-oxyiminoacetyl, 2-thienyl-2-(3-morpholinopropyloxyimino)acetyl, 2-(5-chloro-2-(5-chloroacetamidothiazol-4-yl)-2-methoxyiminoacetyl, 2-(5-chloro-2-aminothiazol-4-yl)-2-methoxyiminoacetyl, 2-(2-aminothiazol-4-yl)-2-(1-carboxy-1-methylethoxyimino)acetyl, 2-[1-(t-butoxycarbonyl)-1-methylethoxyimino]-2-(2-sulfoaminothiazol-4-yl)acetyl, 2-[1-(t-butoxycarbonyl)-1-methylethoxyimino]-2-(2-triphenylemthylaminothiazol-4-yl)acetyl, 2-(2-chloroacetamidothiazol-4-yl)-2-(1-methylethoxyimino)acetyl, 2-methoxyimino-2-(2-hydroxysulfonylaminothiazol-4-yl)acetyl, 2-[2-(2-chloroacetamidothiazol-4-yl)-2-methoxyiminoacetamido]-2-phenylacetyl, 2-[2-(2-aminothiazol-4-yl)-2-methoxyiminoacetamido]acetyl, 2-(2-mesylaminithiazol-4-yl)-2-(1-methylethoxyimino)acetyl, 2-(2-aminothiazol-4-yl)-2-[(carboxy)methoxyimino]acetyl, 2-(2-aminothiazol-4-yl)-2-[(1-carboxy)ethoxyimino]acetyl, 2-(2-chloroacetoamidothiazol-4-yl)-2-[1-(2-trimethylsilylethoxycarbonyl)-1-methylethoxyimino]acetyl, 2-[1-(2-trimethylsilylethoxycarbonyl)-1-methylethoxyimino]-2-(2-tritylaminothiazol-4-yl)acetyl, 2-(2-aminothiazol-4-yl)-2-[(1-carbamoyl-1-methyl)ethoxyimino]acetyl, 2-(2-aminothiazol-4-yl)-2-[(1-methoxycarbonyl-1-methyl)ethoxyimino]acetyl, 2-(2-aminothiazol-4-yl)-2-[(carbamoyl)methoxyimino]acetyl, 2-(2-aminothiazol-4-yl)-2-[(tetrazol-5-yl)methoxyimino]acetyl, 2-(2-aminothiazol-4-yl)-2-[(methoxycarbonyl)methoxyimino]acetyl, etc.

Examples of the acyl group of the formula

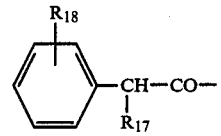

($R_{17}$ and $R_{18}$ beng as above defined) are α-sulfophenylacetyl, α-hydroxysulfonyloxyphenylacetyl, α-hydroxyphenylacetyl, α-sulfamoylphenylacetyl, α-(phenoxycarbonyl)phenylacetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl, 2-bromo-2- phenylacetyl, 2-azido-2-phenylacetyl, 2-phthalimido-2-thienylacetyl, 2-azido-2-(3-chlorophenyl)acetyl, etc.

Examples of the acyl group of the formula $R_{19}-R_{20}-CH_2-CO-$ ($R_{19}$ and $R_{20}$ being as above defined) are cyanoacetyl, phenylacetyl, phenoxyacetyl, trifluoromethylthioacetyl, cyanomethylthioacetyl, 1H-tetrazolyl-1-acetyl, 2-thienylacetyl, 2-(2-aminothiazol-4-yl)acetyl, 2-(2-chloroacetamidothiazol-4-yl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-[2-[(2-oxoimidazolidin-1-yl)carbonylaminomethyl]phenyl]acetyl, 2-[2-[(3-benzylideneamino-2-oxoimidazolidin-1-yl)carbonylaminomethyl]phenyl]acetyl, 2-(5,6-dihydro-1,4-oxathiin-2-yl)acetyl, 2-(2,5-dioxopyrrolidin-3-yl)acetyl, 2-succinimidoacetyl, 2-(1-acetyl-2,4-dioxoimidazolin-3-yl)acetyl, etc.

The amino and/or carboxyl group in the above acyl groups may be protected.

The protective groups for said amino groups are those "amino-protective groups" that are to be mentioned hereinafter.

The protective groups for said carboxyl group include all groups generally usable as carboxyl-protecting groups in the field of β-lactam compound and organic chemistry, their ester moieties being, for example, methyl, ethyl, propyl, isopropyl, t-butyl, t-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β, β, β-trichloroethyl, β-iodoethyl, t-butyldimethylsilyl, t-butyldiphenylsilyl, 2-trimethylsilylethyl, 2-cyanoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxido-2-methyl, methylsulfinylmethyl, bis(p-methoxyphenyl)methyl and 2-cyano-1,1-dimethylethyl.

The present invention is to provide novel 1-sulfo-2-oxoazetidine compounds [I] and the selection of said protective group is not critical, but particularly, benzyl, β, β, β-trichloroethyl, p-nitrobenzyl, p-methoxybenzyl, benzhydryl, 2-trimethylsilylethyl and tert-butyl are preferred.

As the protective group for the amino group in the above formulas, there may be adopted any of those used for the same purpose in the field of β-lactam and peptide synthesis. For example, there may be used an aromatic acyl or sulfonyl group, such as phthaloyl, p-nitrobenzoyl, p-tert-butylbenzoyl, p-tert-butylbenzenesulfonyl, benzenesulfonyl and toluenesulfonyl, an aliphatic acyl or sulfonyl group, such as formyl, acetyl, propionyl monochloroacetyl, dichloroacetyl, trichloroacetyl, methanesulfonyl, ethanesulfonyl, trifluoroacetyl, maloyl and succinyl, benzyloxycarbonyl, p-nitrobenzyloxycarbonyl, p-methoxybenzyloxycarbonyl, 2-trimethylsilylethoxycarbonyl, methoxycarbonyl, and further amino-protecting groups other than acyl groups, for example trityl, 2-nitrophenylthio, benzylidene, 4-nitrobenzylidene, di- or trialkylsilyl, tert-butyldimethylsilyl, tert-butyldiphenylsilyl, benzyl and p-nitrobenzyl. Like in the case of the carboxyl protecting group, the selection of said protective group is not critical, but particularly preferred are monochloroacetyl, benzyloxycarbonyl, p-methoxybenzyloxycarbonyl, p-nitrobenzyloxycarbonyl and 2-trimethylsilylethoxycarbonyl.

Referring to the above formula, from the viewpoint of excellent antimicrobial activity and β-lactamase inhibitory activity, an amino group which may be acylated or protected represented by $R_1$ includes among others a group of the formula,

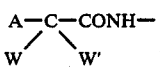

wherein A is hydrogen, a lower alkyl group such as methyl, ethyl and isobutyl, an alicyclic group such as cyclohexyl and cyclohexenyl, an aryl group such as phenyl, an aralkyl group such as phenoxybenzyl, or a heterocyclic group such as thienyl, benzothienyl, pyrrolyl, isoxazolyl, piperazinyl, thiazolyl, tetrazolyl or oxathiano, and it may have one or two substituents selected from amino, a lower alkyl, a lower alkoxy, phenoxy, oxo, hydroxyl, a halogen and chloroacetamido; when W' is hydrogen, W is a carboxyl group which may optionally be esterified, a sulfo group, a sulfamoyl group, a hydroxysulfonyloxy group, an amino group which may optionally be protected, an amido group such as an arylcarboxamido (e.g. phenylcarboxamido) and a lower alkylcarboxamido, or a heterocycle-carboxamido group such as 2,3-dioxo-1-piperazinecarboxamido, imidazolidinecarboxamido, oxoimidazolidinecarboxamido, (isoxazol-4-yl)carboxamido, (2-aminothiazol-4-yl)methylcarboxamido or 3-(2,3-dioxo-1-piperazinecarboxamido)-2-carbobenzoxyaminopropionamide, or W and W' may combinedly represent a group of the formula, $=N-X'-G$ wherein X' is an oxygen or sulfur atom or a sulfoxide group, and G is a lower ($C_{1-4}$) alkyl group, a carboxysubstituted lower ($C_{1-4}$) alkyl group such as α, α-dimethyl-α-carboxymethyl, an aryl group such as phenyl or an acyl group such as acetyl;

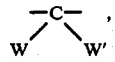

may further represent a mere single bond or

In the above formula, the lower alkyl group represented by A is preferably a straight chain or branched alkyl group containing 1 to 4 carbon atoms and may be substituted by a substituent other than those mentioned above, for example by N-methylcarbamoyl, carbobenzyloxyamino, an aryl group such as phenyl or a heterocyclic group such as tetrazolylacetamido, 4-ethyl-2,3-dioxo-1-piperazinecarboxamido, and 1,2-diazol which may be substituted by phenyl, methyl or ethyl at the 3-position thereof. The halogen by which A may be substituted is, for example, fluorine, chlorine and bromine, the lower alkyl group is, for example, methyl or ethyl, and the lower alkoxy group is, for example, methoxy or ethoxy. The optionally protected amino group represented by W includes chloroacetylamino, aralkylamino and aralkyloxycarbonylamino, among others. The heterocycle in the heterocycle-carboxamido group represented by W may be substituted by phenyl, a lower alkyl group containing 1 to 12 carbon atoms, a saturated alicyclic group, an alkenyl group containing 2 to 8 carbon atoms, an arylcarbonyl group which may be substituted by a lower alkoxy group such as methoxy and ethoxy, a furfurylideneamino group, a sulfo group, an alkoxycarbonyl group, an aralkyloxycarbonyl group or a carboxyl group. The lower alkyl moiety in the lower alkylcarboxamido group represented by W is preferably a straight chain or branched alkyl group containing 1 to 4 carbon atoms and may be substituted by a halogen such as chlorine, bromine and fluorine.

Among these, preferably A is a phenyl, phenoxy, thiazolyl, thienyl or piperazino group, which may be further substituted by an amino, lower alkyl, lower alkoxy group and has an unsubstituted or substituted-amino or methoxyimino substituent at the α-position thereof.

The optionally acylated or protected amino group represented by $R_1$ preferably includes among others, a group of the formula:

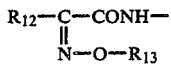

wherein $R_{12}$ is a thiazol-4-yl group having an amino substituent which may be protected at 2-position thereof and $R_{13}$ is a methyl group or a group of the formula, —$R_{14}$—$R_{15}$ where $R_{14}$ is a methylene or dimethylmethylene group and $R_{15}$ is a carboxyl group.

The compound [I], which has a sulfo substituent, can generally react with a base to form a salt thereof. Therefore, the compound [I] may be recovered in the form of a salt, and such salt may be converted into the free form or to another salt. And, the compound [I] obtained in the free form may be converted into a salt. The above-mentioned base includes an inorganic base such as lithium, potassium, sodium, calcium and ammonia, and an organic base such as pyridine, collidine, triethylamine, triethanolamine and tetra-tert-butylammonium hydroxide, among others.

The present invention also covers the compound [I] in a pharmaceutically acceptable salt form. For conversion of the compound obtained in the salt form into the free form, the method using an acid, for example, can be used. Usable acids depend on the kind of protective group and other factors. Frequently used are inorganic acids such as hydrochloric acid, sulfuric acid and phosphoric acid, and organic acids such as formic acid, acetic acid and p-toluenesulfonic acid, among others. Furthermore, acid ion exchange resins, for instance, are also used. Solvents usable in many cases are hydrophilic organic solvents such as acetone, tetrahydrofuran, methanol, ethanol and dioxane, water, and mixed solvents thereof.

For the compound [I], there may exist stereoisomers (e.g. D-isomer, L-isomer, 3R- or 3S-isomer, 4R- or 4S-isomer, (3R,4S)-isomer, (3R,4R)-isomer). In that case, such isomers as well as a mixture thereof are covered by the present invention.

These isomers can be used medicinally either individually or in the form of a mixture. When these isomers are obtained as a mixture thereof, they can be separated from each other by the conventional optical resolution techniques, if necessary or as desired.

The compound [I] may be in the form of a lower ($C_{1-4}$) alkyl ester, such as a methyl, ethyl, n-propyl, isopropyl, n-butyl, or isobutyl ester.

The compound [I] or a pharmaceutically acceptable salt or ester thereof (hereinafter referred to as "the compound of the present invention") shows an antimicrobial activity against certain gram-positive bacteria (e.g. *Staphylococcus aureus*) and gram-negative bacteria (e.g. *Enterobacter cloacae, Pseudomonas aeruginosa, Escherichia coli, Serratia marcescens, Klebsiella pneumoniae* etc.) and is useful as a medicine. The acute toxicity of the compound of the present invention in mice after intravenous administration is not less than 500 mg/kg in terms of $LD_{50}$.

The compound of the present invention is useful for the treatment of prevention of infectious diseases in mammals (e.g. mouse, rat, human) as induced by the above-mentioned bacteria.

The compound of the present invention can be used as an agent for treating bacterial infections, for example in the treatment of respiratory tract infection, urinary tract infection, suppurative diseases, biliary tract infection, enteric infection, gynecological infection and surgical infection, among others. The daily dose is about 20 to 200 mg/kg body weight as the compound [I], which is suitably administered in two or four divided doses, the single dose thus being about 5 to 100 mg/kg body weight. The compound of the present invention can be administered orally in the dosage form of tablet, capsule or lozenge, for instance, or parenterally in the form of an injection prepared by incorporating a preparation for injection made therefrom in the conventional manner into a sterile vehicle prepared by the conventional method, or in the like form.

The compound of the present invention also shows a β-lactamase inhibitory activity, thus being useful as a β-lactamase inhibitor.

The compound of the present invention is used in administering a β-lactam antibiotic for the treatment or prevention of bacterial infections in humans or domestic animals.

When the compound of the present invention alone is made into a preparation, such preparation is either used before or after administration of a β-lactam antibiotic or mixed with a β-lactam antibiotic for simultaneous administration. It is also possible to make the compound of the present invention into a preparation in a mixture with a β-lactam antibiotic. β-lactam antibiotics usable in such case are penicillins and cephalosporins such as benzylpenicillin, phenoxymethylpenicillin, sulbenicillin, carbenicillin, ampicillin, amoxicillin, mecillinam, cloxacillin, dicloxacillin, piperacillin, apalicillin, ticarcillin, cephaloridine, cephalothin, cefazolin, cephalexin, cefacetrile, cafamandole nafate, cefuroxime, cefotiam, cefoxitin, cefmetazole, cefsulodin, cefaclor, cefatrizine, cefotaxime, cefmenoxime, ceftazidine, ceftizoxime and other known penicillins and cephalosporins as well as hetacillin, metampicillin, talampicillin, carindacillin, carfecillin and pivmecillinam. They are used together with the compound of the present invention for the preparation of injection, dry syrup, granules, tablets, capsules and other dosage forms by the conventional methods. A preferred form is an injection in which the active ingredients are used in a pharmaceutically acceptable salt or hydrate form of compound [I]. In such mode of use, the compound of the present invention can be used in an amount of 1/10 to 10 parts by weight per part by weight of the β-lactam antibiotic, the proportion of from 1 to ⅛, for instance 1/5 or 1/6, being advantageous. The compound of the present invention is generally administered in a daily dose of 50 to 1000 mg, or furthermore normally in a daily dose of 20 to 150 mg/kg, for instance, in 1 to 6 divided doses, or normally in 2 to 4 divided doses.

The 1-sulfo-2-oxoazetidine derivative [I] or a pharmaceutically acceptable salt or ester thereof can be produced by subjecting a compound of the formula:

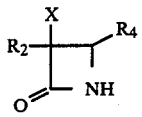 [II]

wherein $R_2$ is an amino group which is either acylated or protected, and X and $R_4$ are as defined above; to a sulfonation reaction, followed by, if desired, removal of protective group. Referring to the above formula, the acyl moiety of the acylated amino group $R_2$ or protective group of the protected amino group $R_2$ is as defined in $R_1$.

The sulfonation reaction means the introduction of a sulfo group and it can be carried out by reacting the compound [II] with sulfuric anhydride, or a reactive derivative of sulfuric anhydride.

The above-mentioned reactive derivative of sulfuric anhydride includes, among others, sulfuric anhydride-pyridine, sulfuric anhydride-dimethylformamide, sulfuric anhydride-dioxane, sulfuric anhydride-trimethylamine, sulfuric anhydride-chlorosulfonic acid, sulfuric anhydride-picoline and the like adducts.

In the sulfonation reaction, about 1 to 5 moles, preferably about 1 to 2 moles, of sulfuric anhydride or a reactive derivative thereof are used per each mole of compound [II]. The reaction temperature is about 0° to 80° C., preferably about 10° to 40° C. The reaction usually carried out in a solvent. As the solvent, organic solvents such as ethers (e.g. dioxane, tetrahydrofuran, diethyl ether), esters (e.g. ethyl acetate, ethyl formate), halogenated hydrocarbons (e.g. chloroform, methylene chloride), hydrocarbons (e.g. benzene, toluene, n-hexane) and amides (e.g. dimethylformamide, dimethylacetamide) and a mixture thereof are used.

The elimination of protective groups can be effected by selective application of a per se known method such as the method involving the use of an acid, one using a base, a reductive method, the method involving the use of hydrazine, the method involving the use of thiourea or sodium N-methyldithiocarbamate. The method involving the use of an acid employs, according to the type of protective group and other conditions such an inorganic acid as hydrochloric acid, sulfuric acid, phosphoric acid, etc., such an organic acid as formic acid, acetic acid, trifluoroacetic acid, propionic acid, benzenesulfonic acid, p-toluenesulfonic acid, etc., acidic ion exchange resins and so on. The method involving the use of a base employs, according to the type of protective group and other conditions, inorganic bases such as the hydroxides or carbonates of alkali metals (e.g. sodium, potassium, etc.) or of alkaline earth metals (e.g. calcium, magnesium, etc.), or organic bases such as metal alkoxides, organic amines, quartenary ammonium salts, or basic ion exchange resins, etc.

When the above method involving the use of an acid or a base is carried out in the presence of a solvent, the solvent is usually a hydrophilic organic solvent, water or a mixed solvent thereof.

The reductive method employs, according to the type of protective group and other conditions, a metal (e.g. tin, zinc, etc.) or a metal compound (e.g. chromous chloride, chromous acetate, etc.) together with an acid such as an organic or inorganic acid (e.g. acetic acid, propionic acid, hydrochloric acid), or involves the use of a metal catalyst for catalytic reduction. The catalyst used for such catalytic reduction may for example be platinum catalysts (e.g. platinum wire, platinum sponge, platinum black, platinum oxide, colloidal platinum, etc.), palladium catalysts (e.g. palladium sponge, palladium black, palladium oxide, palladium-barium sulfate, palladium-barium carbonate, palladium-carbon, palladium-silica gel, colloidal palladium, etc.), reduced nickel, nickel oxide, Raney nickel, Urushihara nickel, etc.

The reductive method involving the use of a metal and an acid employs a metal compound (e.g. of iron or chromium) and an inorganic acid (e.g. hydrochloric acid) or organic acid (e.g. formic acid, acetic acid, propionic acid, etc.). The reductive method is usually conducted in a solvent. In the catalytic reduction method, for instance, the reaction is conducted usually in the presence of an alcohol (e.g methanol, ethanol, propyl alcohol, isopropyl alcohol, etc.), ethyl acetate, etc. The method involving the use of a metal and an acid is usually carried out in the presence of water, acetone or the like, but when the acid is liquid, it may be utilized as the solvent as well.

The reaction is usually conducted in the range of from cooling to warming.

When the protective group is an organic carboxylic acid residue and there is such a substituent as free amino, hydroxyl, mercapto, carboxyl, sulfo, etc. on the carbon atom adjacent to its carbonyl group, it is advantageous to previously conduct a treatment for enhancing the adjacent group effect of such substituent group to render the carbonyl group more reactive and, then, remove the protective group. By way of illustration, when the substituent on the carbon atom adjacent to said carbonyl group is a free amino group, the free amino group is first transformed into a thioureido group before conducting the deacylation reaction. Thus, the protective group can be eliminated by the conventional procedure used for the cleavage of peptide bonds.

The reaction temperature is not critical, but is adequately selected depending on the kind of protective group and the method of elimination, among others. Generally, the reaction can advantageously be carried out under mild conditions, for example with cooling or warming.

When $R_1$ is carboxyl-containing group, there are cases in which the derivative at the carboxyl group is transformed into a free carboxyl group in the course of reaction and these cases are also subsumed in the ambit of this invention.

The compound [I] deprived of the protective group in this manner can be converted to a desired salt by the conventional method.

The starting compound [II] can be subjected to the reaction in the form of a salt or silyl derivative thereof.

Furthermore, a 1-sulfo-2-oxazetidine derivative of the formula:

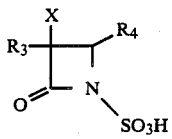

wherein R₃ is an acylated amino group; and X and R₄ are as defined above, or a pharmaceutically accpetable salt or ester thereof, can be produced by subjecting a compound of the formula:

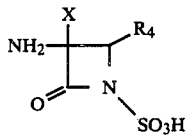

wherein X and R₄ are as defined above; to an acylation reaction.

Referring to the above formula, the acyl moiety of the acylated amino group represented by R₃ is as defined in R₁ above.

This acylation is performed by reacting the compound [III] with an acylating agent. The acylating agent usable in this reaction may be an organic carboxylic acid or a reactive derivative thereof, which contains the acyl moiety of the acylated amino group represented by R₃.

The reactive derivative of an organic carboxylic acid mentioned includes among others acid anhydrides, active amides, and active esters. To be concrete, such reactive derivatives of organic carboxylic acids are:

(1) Acid anhydrides:

The acid anhydrides include, among others, mixed anhydride with a hydrohaloic acid (e.g. hydrochloric acid, hydrobromic acid), mixed anhydrides with a monoalkyl carbonic acid, mixed anhydrides with an aliphatic carboxylic acid (e.g. acetic acid, pivalic acid, valeric acid, isopentanoic acid, trichloroacetic acid), mixed anhydrides with an aromatic carboxylic acid (e.g. benzoic acid), and the symmetric acid anhydride.

(2) Activated amides:

The activated amides include amides with pyrazole, imidazole, 4-substituted imidazole, dimethylpyrazole, benzotriazole, etc.

(3) Activated esters:

The activated esters include, among others, such esters as methyl, ethyl, methoxymethyl, propargyl, 4-nitrophenyl, 2,4-dinitrophenyl, trichlorophenyl, pentachlorophenyl and mesylphenyl esters as well as esters of such acids as the above-mentioned carboxylic acid with 1-hydroxy-1H-2-pyridone, N-hydroxysuccinimide, 1-hydroxybenzotriazole, N-hydroxy-5-norbornene-2,3-dicarboximide and N-hydroxyphthalamide.

Appropriate reactive derivatives of organic carboxylic acids are selected from among such ones as mentioned above depending on the type of the acid used. When a free acid is used as the acylating agent, the reaction is preferably carried out in the presence of a condensing agent. Examples of the condensing agent are N,N'-dicyclohexylcarbodiimide, N-cyclohexyl-N'-morpholinoethylcarbodiimide, N-cyclohexyl-N'-(4-diethylaminocyclohexyl)carbodiimide and N-ethyl-N'-(3-dimethylaminopropyl)carbodiimide.

In the acylation reaction, about 1 to 3 moles of the acylating agent are usually allowed to react with 1 mole of the compound [III].

The acylation reaction is usually carried out in a solvent. The solvent includes water, acetone, dioxane, acetonitrile, methylene chloride, chloroform, dichloroethane, tetrahydrofuran, ethyl acetate, dimethylformamide, pyridine and other common organic solvents inert to the reaction. Among these, hydrophilic solvents can be used as mixtures with water.

The acylation reaction can be carried out, for example, in the presence of an inorganic base such as sodium hydroxide, sodium carbonate, potassium carbonate or sodium hydrogen carbonate, or an organic base such as an organic teriary amine, for example trimethylamine, triethylamine, tributylamine, N-methymorpholine, N-methylpiperidine, N,N-dialkylaniline, N,N-dialkylbenzylamine, pyridine, picoline, lutidine, 1,5-diazabicyclo[4,3,0]non-5-ene, 1,4-diazabicyclo[2,2,2]octane, 1,8-diazabicyclo[5,4,4]undecene-7 or tetra-n-butylammonium hydroxide. The base or the avove-mentioned condensing agent, when it is a liquid, may serve also as a solvent. The reaction temperature is not critical. Generally, the reaction is conducted in many cases under cooling or at room temperature.

When the acylation reaction is conducted, in case where asymmetric carbons are contained in a reactive derivative of the starting compound [III] at its amino group or in a salt thereof or an acylating agent then employed, stereoisomers can be used as individual single isomer or as a mixture thereof. The reaction product is a mixture of stereoisomers, each isomer can be recovered separately by a conventional procedure, such as column chromatography, crystallization and/or recrystallization.

The starting compound [III] in the acylation reaction may also be in the form of a salt thereof or a silyl derivative thereof. Said salt may include those examples mentioned above for the salt of the compound [I].

When the starting compound used in sulfonation or acylation reaction is in a salt form, the product compounds [I], [IV] may in certain cases be obtained in the salt form. The product in the salt form may also be recovered in another salt form by the same procedure as mentioned above.

Furthermore, the compounds [I], [IV] obtained in the salt form may be recovered in the free form. The conversion of the salt to the free form is effected by the procedure as mentioned above.

The compound [I], when it has a protective group, is useful as an intermediate for the synthesis of medicine, and removal of the protective group, for instance, can convert the same to the protective group-free form of compound [I].

After completion of the reaction, the compounds [I], [IV] or a pharmaceutically acceptable salt or ester thereof can be recovered in a desired purity by a per se known purification/isolation procedure, such as solvent extraction, crystallization, recrystallization and/or chromatography.

The starting compounds [II] and [III] to be used in the practice of the present invention can be prepared, for example, by the method described in Annalen der Chemie, 1974, 539. They can also be produced, for instance, by the routes shown below:

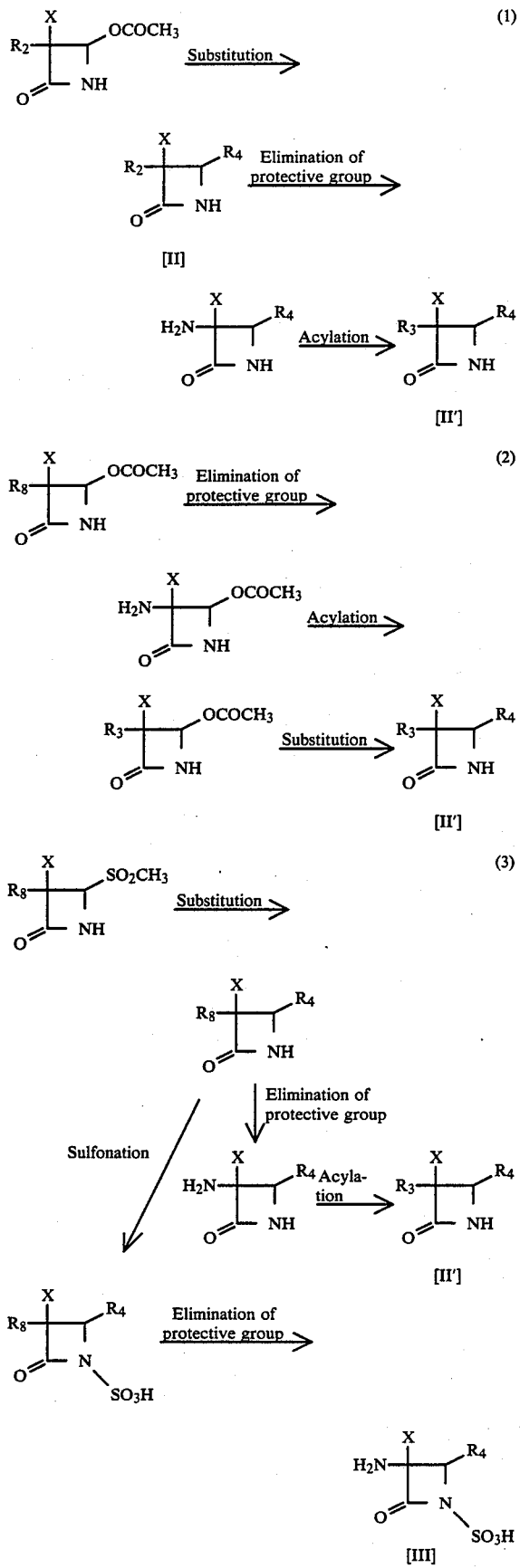

In each of the above reaction formulas, $R_2$, $R_3$, $R_4$ and X are as defined above; and $R_8$ is a protected amino group.

The compounds obtained can be isolated and purified by a procedure known per se such as solvent extraction, crystallization, recrystallization and/or chromatography.

The following Examples and Reference Examples are given to illustrate this invention in further detail. In these examples, NMR spectra were measured with Varian HA 100 (100 MHz), EM 390 (90 MHz) and T 60 (60 MHz) instruments, with tetramethylsilane as a reference standard, and the δ values are shown in ppm. In the chemical shift data, s means a singlet, br.s. a broad singlet, d a doublet, dd a double doublet, t a triplet, q a quartet, m a multiplet, ABq an AB pattern quartet, J a coupling constant, THF tetrahydrofuran, DMF dimethylformamide, DMSO dimethyl sulfoxide, br. a broad, and arom aromatic, DCC dicyclohexylcarbodiimide.

In silica gel column-chromatography, Kiesel Gel 60 (Art 9385, 230–400 Mesh, E. Merck, A. G., Germany) was employed and the elution in the chromatography was carried out with observation of TLC.

Fractions containing the desired compound, which show the same Rf value as that of main spot appearing on TLC plate at TLC for the reaction solution to be subjected to the column-chromatography were collected.

In the TLC were employed HPTLC Kiesel Gel 60 $F_{254}$ plate (Art 5642, E. Merck, A. G., West Germany), a developing solvent which is the same as the eluent employed in the column-chromatography and UV detector.

In XAD-II (produced by Rhom & Haas Co., U.S.A.) colum-chromatography were employed water—20% ethanol as an eluent. Fractions containing the desired compound, which show the absorbance at 254 nm in UV spectrum by use of UVICORD 2 (produced by LKB, Sweden) were collected, followed by lyophilizing to give the objective compound.

REFERENCE EXAMPLE 1

(1) To a solution of 0.114 g of sodium thioglycolate in 10 ml of tetrahydrofuran and 5 ml of water is added 1 ml of 1N sodium hydroxide at room temperature, and then 0.406 g of (3R,4R)-4-methylsulfonyl-3-tritylamino-2-azetidinone is added portionwise to the reaction mixture. After stirring for 15 minutes, the solvent is distilled off and to the residue are added ethyl acetate and diluted hydrochloric acid, followed by stirring. The ethyl acetate layer is separated, washed with water and dried ove anhydrous sodium sulfate. The solvent is then distilled off to give 0.400 g of a mixture of (3R,4R)- and (3R,4S)-4-[[(carboxy)methyl]thio]-3-tritylamino-2-azetidinones.

IR $\nu_{max}^{KBr}$ cm$^{-1}$: 3320, 1734, 1182, 700.

NMR (CDCl$_3$, ppm)δ: 2.88, 3.04 (m, —CH$_2$—) 4.00, 4.50 (m, C$_3$—H, C$_4$—H), 6.35 (br, s, NH, CO$_2$H), 6.8–7.6 (m, arom H).

(2) To a solution of 0.357 g of the 2-azetidinone compound prepared in (1) above in 3 ml of tetrahydrofuran is added diphenyldiazomethane, and the reaction mixture is allowed to stand at room temperature for an hour. The solvent is then distilled off and the residue is purified by silica gel column chromatography [ethyl acetate-n-hexane (1:5 to 1:3)] to give 0.254 g of a mixture of (3R,4R)- and (3R,4S)-4-[[(diphenylmethoxycarbonyl)methyl]thio]-3-tritylamino-2-azetidinones, in a 3:2 W/W ratio.

(3R,4R)-derivative; IR $v_{max}^{KBr}$ cm$^{-1}$: 3320, 1760 1728, 1488, 1443, 1260, 1143, 740, 693.

(3R,4S)-derivative; IR $v_{max}^{KBr}$ cm$^{-1}$: 3320, 1760, 1739, 1486, 1443, 1262, 1129, 970, 741, 693.

(3) To a solution of (3R,4R)-2-azetidinone derivative (1.05 g) prepared in (2) above in 8 ml of acetone is added 0.345 g of p-toluenesulfonic acid monohydrate, and the reaction mixture is stirred at room temperature for one hour. The solvent is distilled off and the residue is washed with diethyl ether and then dissolved in a mixture of tetrahydroguran (15 ml) and water (10 ml). To the solution is added portionwise 0.778 g of [(2-chloroacetylamino-4-thiazolyl)methoxyimino]acetyl chloride monohydrochloride, while maintaining the solution at pH 7.8 to 8.5 with aqueous sodium hydrogen carbonate. The mixture is stirred at room temperature for 30 minutes and ethyl acetate is added to the reaction mixture. The ethyl acetate layer is separated, washed with water and dried over anhydrous magnesium sulfate. The solvent is then distilled off to give 0.945 g of (3R,4R)-4-[[(diphenylmethoxycarbonyl)methyl]thio]-3-[[[(2-chloroacetylamino-4-thiazolyl)methoxyimino]acetyl]amino]-2-azetidinone.

IR $v_{max}^{KBr}$ cm$^{-1}$: 3240, 1773, 1730, 1545, 1272, 1051, 698.

REFERENCE EXAMPLE 2

From 4.808 g of (3R,4R)-4-methylsulfonyl-3-tritylamino-2-azetidinone and 3.034 g of (p-nitrobenzyloxycarbonylamino)ethylthiol in accordance with the procedure of Reference Example 1-(1), a mixture of (3R,4R)- and (3R,4S)-4-[[(p-nitrobenzyloxycarbonylamino)ethyl]thio]-3-tritylamino-2-azetidinones (4.788 g) is obtained. The mixture is purified by silica gel column chromatography using ethyl acetate-n-hexane (1:1). The first eluted fractions give the (3R,4R)-derivative.

To a solution of (3R,4R)-derivative in 15 ml of acetone is added 0.761 g of p-toluenesulfonic acid monohydrate. The mixture is stirred at room temperature for 2 hours, then the solvent is distilled off and the resulting residue is washed with diethyl ether to give 1.74 g of the corresponding sulfonate. This product is dissolved in 4 ml of DMF, followed by addition of 0.25 ml of pyridine (solution A). Separately, 0.25 ml of pyridine, 0.482 g of 1-hydroxybenzotriazole and 0.743 g of DCC (dicyclohexylcarbodiimide) are added to a solution of 1.96 g of [(2-tritylamino-4-thiazolyl)[1-(trimethylsilylethoxycarbonyl)]-1-methylethoxy]iminoacetic acid in 7 ml of DMF under ice-cooling, and the mixture is stirred at room temperature for 3 hours (solution B). The solution A is added to the solution B under ice-cooling, and the mixture is stirred at room temperature for 20 hours. An insoluble material is filtered off and the filtrate is concentrated. To the residue are added ethyl acetate and water, and the organic layer is separated, washed with water and concentrated under reduced pressure. The residue is purified by silica gel column chromatography using ethyl acetate-n-hexane (1:1 to 3:2) to give 0.965 g of (3R,4R)-4-[[(p-nitrobenzyloxycarbonylamino)ethyl]thio]-3-[[[(2-tritylamino-4-thiazolyl)-[[1-(trimethylsilylethoxycarbonyl)]-1-methylethoxy]imino]acetyl]amino]-2-azetidinone.

IR $v_{max}^{KBr}$ cm$^{-1}$: 3290, 2950, 1775, 1720, 1680, 1508, 1345, 1248, 1149, 839.

NMR (DMSO-d$_6$, ppm)δ: 0.02(s, CH$_3$), 0.84–1.10(m, —CH$_2$—), 1.42(br.s, CH$_3$), 2.64, 3.18(m, —CH$_2$—), 3.98–4.25 (m, —CH$_2$—), 5.01(d, J=4 Hz, C$_4$—H), 5.14(s, —CH$_2$—), 5.32(dd, J=4, 8 Hz, C$_3$—H), 6.79(s,

7.1–7.5(m, arom H), 7.58, 8.22(d, J=9 Hz, arom H), 8.74(br.s, NH), 9.02(d, J=8 Hz, NH).

REFERENCE EXAMPLE 3

(1) Methyl 3-methyl-2-(2-bromosulfinyl-4-oxo-3-phthalimido-1-azetidinyl)-3-butenoate (8 g), prepared from methyl 6-phthalimidopenicillanate 1-oxide and N-bromosuccinimide according to a known procedure, is dissolved in 500 ml of carbon tetrachloride and ammonia gas is bubbled into the solution for 30 minutes. The solvent is then distilled off and the residue is dissolved in 200 ml of dichloromethane. The solution is treated with 0.3 ml of triethylamine to give 4.8 g of methyl (3R,4R)-4-aminosulfinyl-3-phthalimido-2-azetidinone-1-(α-isopropylidene)acetate.

NMR(DMSO-d$_6$+CDCl$_3$, ppm)δ: 2.11(s, CH$_3$), 2.20(s, CH$_3$), 3.75(s, OCH$_3$), 4.92(d, J=5 Hz, C$_4$—H), 5.60(d, J=5 Hz, C$_3$—H), 5.88 (br.s, NH$_2$), 7.76(s, arom H).

(2) To a solution of (3R,4R)-4-aminosulfinyl compound (1.263 g) prepared in (1) above in 300 ml of dichloromethane is added 0.656 g of metachloroperbenzoic acid. After stirring at room temperature for 8 hours, the reaction mixture is washed with water, aqueous sodium thiosulfate, water and saturated aqueous sodium chloride, successively, and dried over anhydrous magnesium sulfate. The solvent is then distilled off to give 1.06 g of methyl (3R,4R)-4-sulfamoyl-3-phthalimido-2-azetidinone-1-(α-isopropylidene)acetate as colorless needles.

mp. 229° to 240° C. (decomp.).

Elemental analysis, for C$_{17}$H$_{17}$N$_3$O$_7$S: Calcd. (%): C, 50.12; H, 4.21; N, 10.31; S, 7.87. Found (%): C, 50.03; H, 4.21; N, 10.49; S, 7.95.

IR $v_{max}^{KBr}$ cm$^{-1}$: 3350, 3250, 1784, 1767, 1720, 1385, 1355, 1220, 1170, 755.

NMR(CDCl$_3$, ppm)δ: 2.23(s, CH$_3$), 3.72(s, OCH$_3$), 5.27(br.s, NH$_2$), 5.37, 5.63(d, J=5 Hz, C$_3$—H, C$_4$—H), 7.73(br.s, arom H).

(3) The (3R,4R)-4-sulfamoyl compound (5.5 g) prepared in (2) above is dissolved in 800 ml of dichloromethane and ozone gas is bubbled into the solution under cooling at −70° C. for 45 minutes. The reaction mixture is treated with aqueous sodium hydrogen sulfite and the solvent is distilled off. To a suspension of the residue in 600 ml of methanol is added a catalytic amount (about 100 mg) of sodium methoxide under ice-cooling, and the mixture is stirred for one hour. After addition of 0.5 ml of acetic acid, the methanol is distilled off. To the residue are added ethyl acetate and water, and the ethyl acetate layer is separated and washed with water. The solvent is then distilled off to give 2.7 g of (3R,4R)-3-phthalimido-4-sulfamyol-2-azetidinone.

IR $v_{max}^{KBr}$ cm$^{-1}$: 3370, 3250, 1780, 1768, 1720, 1385, 1352, 1182, 1139, 710.

NMR(DMSO-d$_6$, ppm)δ: 4.93(d, J=5 Hz, C$_4$—H), 5.59(dd, J=2, 5 Hz, C$_3$—H), 7.17(br.s, NH$_2$), 7.92(s, arom H), 9.26(br.d, J=2 Hz, NH).

(4) To a solution of 0.295 g of (3R,4R)-3-phthalimido-4-sulfamoyl-2-azetidinone prepared in (3) above in 5 ml of DMF is added 0.452 g of tert-butyldimethylchlorosilane, and then is added dropwise a solution of 0.203 g of triethylamine in 0.5 ml of DMF under ice-cooling. The reaction mixture is allowed to stand at room temperature overnight and the mixture is concentrated under reduced pressure. The residue is purified by silica gel column chromatography using ethyl acetate-dichloromethane (2:1) to give 0.295 g of the corresponding monosilyl compound.

NMR(DMSO-d6, ppm)δ: 0.10, 0.12, 0.83(s, CH3), 4.91(d, J=5 Hz, C4—H), 5.58(dd, J=2, 5 Hz, C3—H), 7.20(br.s, NH), 7.90 s, arom H), 9.25(d, J=2 Hz, NH).

To a solution of the above monosilyl compound (0.150 g) in 5 ml of DMF are added 0.165 g of tert-butyldimethylchlorosilane and 0.065 g of triethylamine. Then reaction mixture is stirred at room temperature for 6 hours and then concentrated under reduced pressure. The residue is purified by silica gel column chromatography using ethyl acetate-n-hexane (1:3) to give 0.155 g of the corresponding disilyl compound.

IR $\nu_{max}^{KBr}$ cm$^{-1}$: 3420, 3260, 2960, 2940, 1790, 1770, 1724, 1388, 1367, 1260, 1160.

NMR(CDCl3, ppm)δ: 0.26, 0.27, 0.39, 0.42, 0.91, 1.06(s, CH3), 4.44(br.s, NH), 4.86(d, J=5 Hz, C4—H), 5.63(d, J=5 Hz, C3—H), 7.7–8.0(m, arom H).

(5) To a solution of the disilyl compound (1.27 g) prepared in (4) above in 50 ml of dichloromethane is added 9.5 ml of 1M methylhydrazine solution in dimethoxyethane and the reaction mixture is stirred at room temperature for 20 minutes. The solvent is then distilled off and the residue is dissolved in 100 ml of dichloroethane and the solution is refluxed for 6 hours. After evaporation of the solvent, the residue is dissolved in a mixture of tetrahydrofuran (20 ml) and water (20 ml), and to the solution is added 1.2 g of [(2-chloroacetylamino-4-thiazolyl)methoxyimino]acetyl chloride monohydrochloride, with the solution being maintained at pH 7.5 to 8.5 with aqueous sodium hydrogen carbonate. After stirring at room temperature for 30 minutes, the reaction mixture is extracted with ethyl acetate. The ethyl acetate layer is separated, washed with water and the solvent is distilled off. The residue is purified by silica gel column chromatography using ethyl acetate-n-hexane (1:2) to give 1.183 g of the disilyl derivative of (3R,4R)-3-[[[(2-chloroacetylamino-4-thiazolyl)methoxyimino]acetyl]amino]-4-sulfamoyl-2-azetidinone.

IR $\nu_{max}^{KBr}$ cm$^{-1}$: 3280, 2955, 2940, 1765, 1680, 1545, 1360, 1257, 1156, 937, 845, 825, 797.

NMR(CDCl3, ppm)δ: 0.23, 0.33, 0.36, 0,90, 1.01(s, CH3), 4.07(s, OCH3), 4.24(s, ClCH2—), 4.73(d, J=5 Hz, C4—H), 5.12(br.s, NH), 5.78(dd, J=5, 9 Hz, C3—H), 7.29(s,

8.07(d, J=9 Hz, NH), 10.68(br. s, NH).

(6) To a solution of the disilyl derivative of (3R,4R)-3-[[[(2-chloroacetylamino-4-thiazolyl)methoxyimino]acetyl]amino]-4-sulfamoyl-2-azetidinone 0.111 g) prepared in (5) above in 2 ml of methanol is added to 0.02 g of potassium fluoride under ice-cooling. After the reaction mixture is stirred for 20 minutes, the solvent is distilled off and the residue is purified by silica gel column chromatography using ethyl acetate-chloroform-methanol (4:6:1 to 3:3:1) to give 0.064 g of (3R,4R)-3-[[[(2-chloroacetylamino-4-thiazolyl)methoxyimino]acetyl]amino]-4-sulfamoyl-2-azetidinone.

IR $\nu_{max}^{KBr}$ cm$^{-1}$: 3325, 3250, 1785, 1680, 1662, 1543, 1130, 1152, 1041.

NMR(DMSO-d6, ppm)δ: 3.89(s, OCH3), 4.35(s, ClCH2—), 4.88(d, J=5 Hz, C4—H), 5.66(dd, J=5, 9 Hz, C3—H), 6.84(br.s, NH2), 7.52(s,

9.26(br.s, NH), 9.30(d, J=9 Hz, NH), 12.9(br. s, NH).

REFERENCE EXAMPLE 4

A solution of sodium E-(2-ethoxycarbonyl)ethenylthiolate (1.78 g) in 20 ml of water is added to a solution of 3.49 g of (3R,4R)-4-methanesulfonyl-3-tritylamino-2-azetidinone in 100 ml of tetrahydrofuran under ice-cooling, and the reaction mixture is stirred at room temperature for 30 minutes. The solvent is then distilled off under reduced pressure and 100 ml of ethyl acetate is added to the residue. The ethyl acetate layer is separated, washed with saturated aqueous sodium chloride, dried over anhydrous magnesium sulfate, and concentrated under reduced pressure. The residue is purified by silica gel column chromatography using n-hexane-ethyl acetate (2:1). The earlier eluate fractions are combined and concentrated to give 0.488 g of (3R,4R)-4-[[E-2-(ethoxycarbonyl)ethenyl]thio]-3-tritylamino-2-azetidinone.

IR $\nu_{max}^{KBr}$ cm$^{-1}$: 3330, 1768, 1702, 1580, 1248, 1162.

NMR(DMSO-d6, ppm)δ: 1.21(t, J=7 Hz, CH3), 3.64(d, J=8 Hz, NH), 4.12(q, J=7 Hz, —CH2—), 4.48(dd, J=5, 8 Hz, C3—H), 4.89(d, J=5 Hz, C4—H), 5.80(d, J=16 Hz,

7.10–7.50(m, arom H), 7.59(d, J=16 Hz,

8.78(s, NH).

The later eluate fractions give 0.478 g of (3R,4S)-4-[[E-2-(ethoxycarbonyl)ethenyl]thio]-3-tritylamino-2-azetidinone.

IR $\nu_{max}^{KBr}$ cm$^{-1}$: 3310, 1762, 1702, 1580, 1250, 1162.

NMR(DMSO-d6, ppm)δ: 1.19(t, J=7 Hz, CH3), 3.80(dd, J=2, 8 Hz, C3—H), 4.08(q, J=7 Hz, —CH2—), 4.46(d, J=8 Hz, NH), 4.47(d, J=2 Hz, C4—H), 5.60(d, J=16 Hz,

7.10–7.56(m, arom H

8.73(s, NH).

REFERENCE EXAMPLE 5

To a solution of 2.0 g of (3S,4S)-4-azido-3-tritylamino-2-azetidinone in 40 ml of toluene is added 1.33 g of ethyl propionate, and the mixture is refluxed for one hour and then cooled. The resulting crystalline is collected by filtration and dried to give 1.3 g of (3S,4S)-4-[4-(ethoxycarbonyl)-1,2,3-triazol-1-yl]-3-tritylamino-2-azetidinone.

IR $\nu_{max}^{KBr}$ cm$^{-1}$: 3370, 3350, 1785, 1710, 1245, 1230, 1212, 1140.

NMR(DMSO-d$_6$+D$_2$O, ppm)$\delta$: 1.33(t, J=7 Hz, CH$_3$), 4.33(q, J=7 Hz, —CH$_2$—), 4.61(d, J=2 Hz, C$_3$—H), 5.41(d, J=2 Hz, C$_4$—H), 7.04–7.46(m, arom H), 8.15(s,

Further, the filtrate obtained above is concentrated and the residue is purified by silica gel column chromatography using n-hexane-ethyl acetate (3:2) to give 0.73 g of (3S,4S)-4-[5-(ethoxycarbonyl)-1,2,3-triazol-1-yl]-3-tritylamino-2-azetidinone.

IR $\nu_{max}^{KBr}$ cm$^{-1}$: 3325, 1782, 1730, 1312, 1255, 1136.

NMR(DMSO-d$_6$+D$_2$O, ppm)$\delta$: 1.33(t, J=7 Hz, CH$_3$), 4.32(q, J=7 Hz), —CH$_2$—), 4.93(d, J=2 Hz, C$_3$—H), 5.74(d, J=2 Hz, C$_4$—H), 7.04–7.46(m, arom H), 8.05(s,

REFERENCE EXAMPLE 6

To a solution of 2.0 g of (3S,4R)-4-azido-3-tritylamino-2-azetidinone in 35 ml of toluene is added 1.14 g of methyl propionate and the mixture is refluxed for 2 hours. The solvent is then distilled off under reduced pressure and the residue is purified by silica gel column chromatography using n-hexane-ethyl acetate (2:1). The earlier eluate fractions are combined and concentrated under reduced pressure to give 0.818 g of (3S,4R)-[5-methoxycarbonyl)-1,2,3-triazol-1-yl]-3-tritylamino-2-azetidinone (compound A).

Compound A; IR $\nu_{max}^{KBr}$ cm$^{-1}$: 3330, 1780, 1730, 1256.

NMR(DMSO-d$_6$, ppm)$\delta$: 3.87(s, CH$_3$), 3.90(d, J=12 Hz, NH), 4.97(dd, J=4, 12 Hz, C$_3$—H), 6.36(d, J=4 Hz, C$_4$—H), 7.21(s, arom H), 8.13(s,

8.80 (s, NH).

The later eluate fractions give 1.258 g of (3S,4R)-[4-(methoxycarbonyl)-1,2,3-triazol-1-yl]-3-tritylamino-2-azetidinone (compound B).

Compound B; IR $\nu_{max}^{KBr}$ cm$^{-1}$: 3340, 3275, 1785, 1712, 1237.

NMR(DMSO-d$_6$, ppm)$\delta$: 3.87(s, CH$_3$), 4.07 (d, J=10 Hz, NH), 4.89(dd, J=4, 10 Hz, C$_3$—H), 5.84(d, J=4 Hz, C$_4$—H), 7.20(s, arom H), 8.57(s,

8.86 (s, NH).

REFERENCE EXAMPLE 7

To a solution of 10 g of (3R,4R)-4-methylsulfonyl-3-tritylamino-2-azetidinone in 250 ml of methanol is added 100 ml of tetrahydrofuran, followed by addition of 3.45 g of methyl thioglycollate and 32.5 ml of 1N sodium hydroxide under ice-cooling, and the mixture is stirred at room temperature for 30 minutes. The solvent is then distilled off under reduced pressure and 100 ml of ethyl acetate is added. The ethyl acetate layer is separated, washed with saturated aqueous sodium chloride, dried over anhydrous magnesium sulfate and concentrated under reduced pressure. The residue is purified by silica gel column chromatography using n-hexane-ethyl acetate (3:2). The earlier eluate fractions are combined and concentrated under reduced pressure to give 4.35 g of (3R,4R)-4-[[(methoxycarbonyl)methyl]thio]-3-tritylamino-2-azetidinone.

IR $\nu_{max}^{KBr}$ cm$^{-1}$: 3300, 1760–1725, 1275, 1152.

NMR(CDCl$_3$, ppm)$\delta$: 2.96(ABq, J=15 Hz, —CH$_2$—), 2.98(d, J=9 Hz, NH), 3.61(s, —CH$_3$), 4.42(dd, J=6, 9 Hz, C$_3$—H), 4.43(d, J=6 Hz, C$_4$—H), 6.67(s, NH), 6.80–7.50(m, arom H).

The later eluate fractions give 4.60 g of (3R,4S)-4-[[(methoxycarbonyl)methyl]thio]-3-tritylamino-2-azetidinone.

IR $\nu_{max}^{KBr}$ cm$^{-1}$: 3315, 1760–1725, 1275, 1153.

NMR(CDCl$_3$, ppm)$\delta$: 2.93(s, —CH$_2$—), 3.57 (s, CH$_3$), 3.90–4.20(m, C$_3$—H, C$_4$—H), 6.55(br.s, NH), 6.80–7.50(m, arom H).

REFERENCE EXAMPLE 8

To a solution of 0.477 g of (3R,4S)-4-[[(methoxycarbonyl)methyl]thio]-3-tritylamino-2-azetidinone in 5 ml of ethanol is added 1 ml of 25 to 28% aqueous ammonia and the reaction mixture is allowed to stand at room temperature for 2 days. The solvent is then distilled off under reduced pressure and 20 ml of ethyl acetate is added to the residue. The mixture is washed with saturated aqueous sodium chloride, dried over anhydrous magnesium sulfate and concentrated under reduced pressure. The residue is purified by silica gel column chromatography using ethyl acetate-chloroform-methanol (8:8:1) to give 0.173 g of (3R,4S)-4-[[(aminocarbonyl)methyl]thio]-3-tritylamino-2-azetidinone.

IR $\nu_{max}^{KBr}$ cm$^{-1}$: 3415, 3310, 3180, 1740, 1670.

NMR (DMSO-d$_6$, ppm)$\delta$: 2,81(s, —CH$_2$—), 3.71 (dd, J=2, 10 Hz, C$_3$—H), 4.22(d, J=10 Hz, NH), 4.27(d, J=2 Hz, C$_4$—H), 6.99(br. s, NH$_2$), 7.10–7.57(m, arom H), 8.29(s, NH).

REFERENCE EXAMPLE 9

To a solution of 4.35 g of (3R,4R)-4-[[(methoxycarbonyl)methyl]thio]-3-tritylamino-2-azetidinone in 45 ml of ethanol is added 11 ml of 25 to 28% aqueous ammonia and the reaction mixture is allowed to stand at room temperature for 2 days. The mixture is further treated in the same manner as described in Reference Example 8 to give 1.804 g of (3R,4R)-4-[[(aminocarbonyl)methyl]thio]-3-tritylamino-2-azetidinone.

IR $\nu_{max}^{KBr}$ cm$^{-1}$: 3420, 3285, 3150–3075, 1745, 1666.

NMR(DMSO-d$_6$, ppm)δ: 2.89(ABq, J=14 Hz, 4.28(dd, J=5, 9 Hz, C$_3$—H), 4.48(d, J=5 Hz, C$_4$—H), 7.15–7.57(m, arom H), 8.37(s, NH).

REFERENCE EXAMPLE 10

Under ice-cooling, 2.58 g of 2-mercaptoethanol and 33 ml of 1N sodium hydroxide are added to a solution of 12.2 g of (3R,4R)-4-methylsulfonyl-3-tritylamino-2-azetidinone in 150 ml of tetrahydrofuran, and the mixture is stirred for 30 minutes. The solvent is then distilled off under reduced pressure and 150 ml of ethyl acetate is added. The ethyl acetate layer is separated, washed with saturated aqueous sodium chloride, dried over anhydrous magnesium sulfate and concentrated under reduced pressure. The residue is purified by silica gel column chromatography using ethyl acetate-n-hexane (1:2). The earlier eluate fractions are combined and concentrated under reduced pressure to give 5.6 g of (3R,4R)-4-[[2-(hydroxy)ethyl]thio]-3-tritylamino-2-azetidinone.

IR $\nu_{max}^{KBr}$ cm$^{-1}$: 3350, 1750.

NMR(DMSO-d$_6$, ppm)δ: 2.34(m, —CH$_2$—), 3.45(m, —CH$_2$—), 4.18–4.43(m, C$_3$—H, C$_4$—H, NH), 4.68(m, OH), 7.10–7.66(m, arom H), 8.40(s, NH).

The later eluate fractions give 4.1 g of (3R,4S)-4-[[2-(hydroxy)ethyl]thio]-3-tritylamino-2-azetidinone.

IR $\nu_{max}^{KBr}$ cm$^{-1}$: 3380, 1750, 1728.

NMR(DMSO-d$_6$, ppm)δ: 2.24(t, J=7 Hz, —CH$_2$—), 3.32(t, J=7 Hz, —CH$_2$—), 3.63(dd, J=2,9 Hz, C$_3$—H), 4.15(d, J=9 Hz, NH), 4.17(d, J=2 Hz, C$_4$—H), 4.54(m, —OH), 7.10–7.60(m, arom H), 8.29(s, NH).

REFERENCE EXAMPLE 11

To a solution of (3R,4S)-4-[[2-(hydroxy)ethyl]thio]-3-tritylamino-2-azetidinone (1.12 g) obtained in Reference Example 10, in 20 ml of methylene chloride are added 0.401 g of triethylamine and 0.328 g acetyl chloride under ice-cooling. The mixture is stirred at room temperature for 1.5 hours, washed with water and saturated aqueous sodium chloride, successively, dried over anhydrous magnesium sulfate and concentrated under reduced pressure. The residue is purified by silica gel column chromatography using ethyl acetate-n-hexane (1:1) to give 0.96 g of (3R,4S)-4-[[2-(acetoxy)ethyl]thio]-3-tritylamino-2-azetidinone.

IR $\nu_{max}^{KBr}$ cm$^{-1}$: 3270, 1750, 1485, 1445, 1210, 1180.

NMR(CDCl$_3$, ppm)δ: 2.00(s, CH$_3$), 2.42 (t, J=7 Hz, —CH$_2$—), 2.85(d, J=8 Hz, NH), 3.82–4.28(m, C$_3$—H, C$_4$—H, —CH$_2$—), 6.42(s, NH), 7.05–7.60(m, arom H).

REFERENCE EXAMPLE 12

To a solution of (3R,4S)-4-[[2-(hydroxy)ethyl]thio]-3-tritylamino-2-azetidinone (2.6 g) obtained in Reference Example 10 in 20 ml of methylene chloride is added dropwise a solution of 1.0 g of monochloroacetyl isocyanate in 5 ml of methylene chloride over 5 minutes under ice-cooling. The mixture is stirred for 10 minutes and concentrated under reduced pressure. The residue is purified by silica gel column chromatography using n-hexane-ethyl acetate (1:1) to give 3.3 g of (3R,4S)-4-[[2-[(chloroacetylamino)carboxy]ethyl]thio]-3-tritylamino-2-azetidinone.

IR $\nu_{max}^{KBr}$ cm$^{-1}$: 3260, 1755–1720, 1485, 1200.

NMR(DMSO-d$_6$, ppm)δ: 2.48(m, —CH$_2$—), 3.70 (d, J=10 Hz, NH), 4.00(t, J=7 Hz, —CH$_2$—), 4.30(d, J=2 Hz, C$_4$—H), 4.43(dd, J=2, 10 Hz, C$_3$—H), 6.90–7.60(m. arom H), 8.34(s, NH).

REFERENCE EXAMPLE 13

From 2.6 g of (3R,4R)-4-[[2-(hydroxy)ethyl]thio]-3-tritylamino-2-azetidinone obtained in Reference Example 10 and 1.0 g of monochloroacetyl isocyanate, 3.06 g of (3R,4R)-4-[[[2-(chloroacetylamino)carboxy]ethyl]thio]-3-tritylamino-2-azetidinone is obtained in accordance with the same manner as in Reference Example 12.

IR $\nu_{max}^{KBr}$ cm$^{-1}$: 3270, 1755, 1490, 1205.

NMR(DMSO-d$_6$, ppm)δ: 2.50(m, —CH$_2$—), 3.24 (d, J=9 Hz, NH), 4.12(t, J=7 Hz, —CH$_2$—), 4.33(dd, J=5, 9 Hz, C$_3$—H), 4.47(s, —CH$_2$—), 4.54(d, J=5 Hz, C$_4$—H), 7.15–7.56(m, arom H), 8.51(s, NH), 10.97(s, NH).

REFERENCE EXAMPLE 14

To a solution of 1.0 g (2.2 mmol) of (3S,4R)-[4-(methoxycarbonyl)-1,2,3-triazol-1-yl]-3-tritylamino-2-azetidinone (compound B) obtained in Reference Example 6 in 15 ml of acetone is added 0.503 g (2.65 mmol) of p-toluenesulfonic acid monohydrate, and the mixture is stirred at room temperature for 40 minutes. The acetone is distilled off under reduced pressure, the residue is triturated with diethyl ether, and the resulting powder is collected by filtration. To a suspension of 0.90 g (2.7 mmol) of [(2-chloroacetylamino-4-thiazolyl) (methoxyimino)]acetyl chloride hydrochloride in 20 ml of methylene chloride is added dropwise 0.95 g (9.4 mmol) of triethylamine under cooling at −70° C. and then are added the above obtained powder and 1 ml of propylene oxide. The temperature of the reaction mixture is then raised to room temperature over one hour to separate crystals. The crystals are collected by filtration, washed thoroughly with methylene chloride and dried to give 0.899 g (1.9 mmol) of (3S,4R)-3-[[[(2-chloroacetylamino-4-thiazolyl) (methoxyimino)] acetyl]amino]-4-[4-)methoxycarbonyl)-1,2,3-triazol-1-yl]-2-azetidinone.

IR $\nu_{max}^{KBr}$ cm$^{-1}$: 3270, 1785, 1728, 1672, 1540, 1220, 1043.

NMR(DMSO-d$_6$, ppm)δ: 3.64(s, CH$_3$), 3.86(s, CH$_3$), 4.34(s, —CH$_2$—), 5.70(m, C$_3$—H), 6.55(d, J=4 Hz, C$_4$—H), 7.07(s,

H), 8.75 (s,

), 9.40(s, NH), 9.45(d, J=9 Hz, NH).

The following compounds are obtained according to the similar manner as described above:

(3S,4R)-3-[[[(2-Chloroacetylamino-4-thiazolyl) (methoxyimino)]acetyl]amino]-4-[5-(methoxycarbonyl)-1,2,3-triazol-1-yl]-2-azetidinone IR $\nu_{max}^{KBr}$ cm$^{-1}$: 3400, 1785, 1725, 1672, 1615, 1525, 1265, 1053.

NMR (DMSO-d$_6$, ppm)δ: 3.61(s, CH$_3$), 3.89(s, CH$_3$), 5.65(dd, J=5,8 Hz, C$_3$—H), 6.30(s,

7.06(d, J=5 Hz, C$_4$—H), 7.09(s, NH$_2$), 8.32(s,

9.24(d, J=8 Hz, NH).

(3R,4R)-3-[[[(2-Chloroacetylamino-4-thiazolyl) (methoxyimino)]acetyl]amino]-4-[[E-2-(ethoxycarbonyl)ethenyl]thio]-2-azetidinone IR $\nu_{max}^{KBr}$ cm$^{-1}$: 3250, 1765, 1705, 1660, 1585, 1542, 1170.

NMR (DMSO-d$_6$, ppm)δ: 1.19(t, J=7 Hz, CH$_3$), 3.85(s, CH$_3$), 4.10(q, J=7 Hz, —CH$_2$—), 4.31(s, —CH—), 5.33-5.70 (m, C$_3$—H, C$_4$—H), 5.88(d, J=15 Hz,

7.33(s,

7.72(d, J=15Hz,

9.04(s, NH), 9.57(m, NH).

REFERENCE EXAMPLE 15

To a solution of 0.92 g (2 mmol) of (3R,4S)-4-[[2-(acetoxy)ethyl]thio]-3-tritylamino-2-azetidinone obtained in Reference Example 11 in 15 ml of acetone is added 0.50 g (2.6 mmol) of p-toluenesulfonic acid monohydrate and the mixture is stirred at room temperature for 30 minutes. The acetone is then distilled off under reduced pressure, the residue is triturated with diethyl ether, and the resulting powder is collected by filtration.

To a suspension of 0.71 g (2.14 mmol) of [(2-chloroacetylamino-4-thiazolyl) (methoxyimino]acetyl chloride monohydrochloride in 20 ml of methylene chloride is added dropwise 0.75 g (7.42 mmol) of triethylamine under cooling at −70° C. over 5 minutes, and then are added the above powder and 2 ml of propylene oxide. The temperature of the reaction mixture is raised to room temperature over one hour. The reaction mixture is concentrated under reduced pressure and the residue is purified by silica gel column chromatography using ethyl acetate-chloroform-methanol (10:10:1) to give 0.752 g (1.62 mmol) of (3R,4S)-4-[[(2-acetoxy)ethyl]thio]-3-[[[2-(chloroacetylamino-4-thiazolyl) (methoxyimino)]acetyl]amino]-2-azetidinone.

IR $\nu_{max}^{KBr}$ cm$^{-1}$: 3270, 1760, 1740, 1663, 1545, 1265, 1230, 1040.

NMR(DMSO-d$_6$, ppm)δ: 2.00(s, CH$_3$), 2.88(t, J=7 Hz, —CH$_2$—), 3.90(s, CH$_3$), 4.17(t, J=7 Hz, —CH$_2$—), 4.33(s, —CH$_2$—), 4.68(dd, J=2, 8 Hz, C$_3$—H), 4.75(d, J=2 Hz, C$_4$—H), 7.40(s,

8.83(s, NH), 9.38(d, J=8 Hz, NH), 12.87(s, NH).

The following compounds are obtained according to the same manner as described above:

(3R,4S)-3-[[[(2-Chloroacetylamino-4-thiazolyl) (methoxyimino)]acetyl]amino]-4-[[E-2-(ethoxycarbonyl)ethenyl]thio]-2-azetidinone IR $\nu_{max}^{KBr}$ cm$^{-1}$: 3250, 1765, 1675, 1542, 1260, 1038.

NMR(DMSO-d$_6$, ppm)δ: 1.21(t, J=7 Hz, CH$_3$), 3.92(s, CH$_3$), 4.12(q, J=7 Hz, —CH$_2$—), 4.36 (s, —CH$_2$—), 4.81(dd, J=2, 8 Hz, C$_3$—H), 5.15 (d, J=2 Hz, C$_4$—H), 5.94(d, J=16 Hz,

7.42(s,

7.76(d, J=16 Hz,

9.12(s, NH), 9.47(d, J=8 Hz, NH).

(3R,4S)-3-[[[(2-Chloroacetylamino-4-thiazolyl) (methoxyimino)]acetyl]amino]-4-[5-(ethoxycarbonyl)-1,2,3-triazol-1-yl]-2-azetidinone IR $\nu_{max}^{KBr}$ cm$^{-1}$: 3395, 3190, 3125, 3070, 2980, 1802, 1727, 1660, 1550, 1310, 1260.

NMR (DMSO-d$_6$, ppm)δ: 1.39(t, J=7 Hz, CH$_3$), 3.93(s, CH$_3$), 4.34(s, —CH$_2$—), 4.40(q, J=7 Hz, —CH$_2$—), 5.52(dd, J=2, 8Hz, C$_3$—H), 6.69 (d, J=2 Hz, C$_4$—H), 7.48(s,

8.37(s,

9.41(s, NH), 9.55(d, J=8 Hz, NH).

(3S,4S)-3-[[[(2-Chloroacetylamino-4-thiazolyl] (methoxyimino)]acetyl]amino]-4-[4-ethoxycarbonyl)-1,2,3-triazol-1-yl]-2-azetidinone IR $\nu_{max}^{KBr}$ cm$^{-1}$: 3250, 1792, 1730, 1690, 1675, 1545, 1210, 1040.

NMR(DMSO-d$_6$, ppm)δ: 1.32(t, J=7Hz, CH$_3$), 3.92(s, CH$_3$), 4.35(q, J=7 Hz, —CH$_2$—), 4.38 (s, —CH$_2$—), 5.34(dd, J=2, 8 Hz, C$_3$—H), 6.29(d, J=2 Hz, C$_4$—H), 7.47(s,

9.17(s,

9.42(s, NH), 9.56(d, J=8 Hz, NH).

REFERENCE EXAMPLE 16

(1) To a solution of 0.75 g (1.74 mmol) of (3R,4S)-4-[[(aminocarbonyl)methyl]thio]-3-tritylamino-2-azetidinone obtained in Reference Example 8 in 30 ml of acetone is added 0.40 g (2.09 mmol) of p-toluenesulfonic acid monohydrate, and the mixture is stirred at room temperature for 30 minutes. The acetone is then distilled off under reduced pressure and the residue is triturated with diethyl ether and collected by filtration. To a solution of the powder obtained above in 5 ml of DMF is added 0.512 g (1.91 mmol) of pyridine under ice-cooling, and the mixture is stirred for 15 minutes.

Separately, 0.431 g (2.09 mmol) of DCC (dicyclohexylcarbodiimide) is added to a solution of 0.532 g (1.91 mmol) of [(2-chloroacetylamino-4-thiazolyl) (methoxyimino)]acetic acid and 0.294 g (1.91 mmol) of 1-hydroxybenzotriazole in 10 ml of DMF under ice-cooling, and the mixture is stirred at room temperature for one hour. To the mixture is added the previously prepared solution, and the whole mixture is stirred at room temperature for 5 hours. An insoluble material is filtered off and the filtrate is concentrated under reduced pressure. The residue is solidified by addition of methylene chloride and the solid product is collected by filtration, washed thoroughly with methylene chloride and dried to give 0.602 g (1.38 mmol) of (3R,4S)-4-[[(aminocarbonyl)methyl]thio]-3-[[[(2-chloroacetylamino4-thiazolyl) (methoxyimino)]acetyl]amino]-2-azetidinone.

IR $\nu_{max}^{KBr}$ cm$^{-1}$: 3265, 3170, 1756, 1655, 1545–1520.

NMR(DMSO-d$_6$, ppm)δ: 3,30(s, —CH$_2$—), 3.90 (s, CH$_3$), 4.33(s, —CH$_2$—), 4.74(dd, J=2, 8 Hz, C$_3$—H), 4.84(d, J=2 Hz, C$_4$—H), 7.43(s,

8.74(s, NH), 9.36(d, J=8 Hz, NH), 11.87(s, NH).

The following compounds are obtained according to the same manner as described above:

(3R,4R)-4-[[(Aminocarbonyl)methyl]thio]-3-[[[(2-chloroacetylamino-4-thiazolyl) (methoxyimino)-]acetyl]amino]-2-azetidinone IR $\nu_{max}^{KBr}$ cm$^{-1}$: 3225, 1763, 1658, 1545.

NMR (DMSO-d$_6$, ppm)δ: 3.19(s, —CH$_2$—), 3,88(s, CH$_3$), 4.34(s, —CH$_2$—), 5.11(d, J=5 Hz, C$_4$—H), 5.38(dd, J=5, 8 Hz, C$_3$—H); 7.50(s,

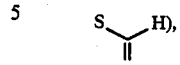

8.76(s, NH), 9.55(d, J=8 Hz, NH), 12.88(s, NH).

(3R,4R)-3-[[[(2-Chloroacetylamino-4-thiazolyl) (methoxyimino)]acetyl]amino]-4-[[2-(hydroxy)ethyl]thio]-2-azetidinone IR $\nu_{max}^{KBr}$ cm$^{-1}$: 3250, 1765, 1670, 1545, 1055.

NMR (DMSO-d$_6$, ppm)δ: 2.65(t, J=7 Hz, —CH$_2$—), 3.57(t, J=7 Hz, —CH$_2$—), 3.91(s, CH$_3$), 4.33(s, —CH$_2$—), 5.04(d, J=5 Hz, C$_4$—H), 5.37(dd, J=5, 8 Hz, C$_3$—H), 7.50(s,

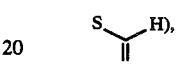

8.74(s, NH), 9.45(d, J=8 Hz, NH), 12.91(s, NH).

(3R,4S)-4-[[2-[(Chloroacetylamino)carboxy]ethyl]thio]-3-[[[(2-chloroacetylamino-4-thiazole)(methoxyimino)]acetyl]amino]-2-azetidinone IR $\nu_{max}^{KBr}$ cm$^{-1}$: 3270, 1778, 1756, 1662, 1540, 1205.

NMR (DMSO-d$_6$, ppm)δ: 2.93(t, J=7 Hz, —CH$_2$—), 3.90(s, CH$_3$), 4.27(t, J=7 Hz, —CH$_2$—), 4.33(s, —CH$_2$—), 4.44(s, —CH$_2$—), 4.73(dd, J=2, 8 Hz, C$_3$—H), 4.77(d, J=2 Hz, C$_4$—H), 7.37 (s,

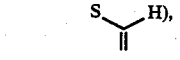

8.79(s, NH), 9.36(d, J=8 Hz, NH), 10.99(s, NH).

(3R,4R)-4-[[2-[(Chloroacetylamino)carboxy]ethyl]thio]-3-[[[(2-chloroacetylamino-4-thiazolyl)(methoxyimino)]acetyl]amino]-2-azetidinone IR $\nu_{max}^{KBr}$ cm$^{-1}$: 3260, 1763, 1695, 1665, 1540, 1208.

NMR (DMSO-d$_6$, ppm) δ: 2.81(m, —CH$_2$—), 3.87(s, CH$_3$), 4.22(t, J=7 Hz, —CH$_2$—), 4.32(s, —CH$_2$—), 4.45(s, —CH$_2$—), 5.11(d, J=5 Hz, C$_4$—H), 5.35(dd, J=5, 9 Hz, C$_3$—H), 7.45 (s,

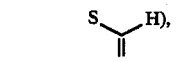

8.80(s, NH), 9.48(d, J=9 Hz, NH), 10.95(s, NH), 12.90(s, NH).

REFERENCE EXAMPLE 17

To a solution of 0.65 g of (3R,4R)-3-[[[(2-chloroacetylamino-4-thiazolyl)(methoxyimino)]acetyl]amino]-4-[[2-(hydroxy)ethyl]thio]-2-azetidinone in 5 ml of dimethylacetamide are added 1 ml of propylene oxide and 0.36 g of acetyl chloride, and the mixture is stirred at 0° C. for 3 hours. After further addition of 0.36 g of acetyl chloride, the mixture is stirred for additional 3 hours. The solvent is then distilled off under reduced pressure to give crystals, which are collected by filtration and washed with methylene chloride. The above procedure gives 0.558 g of (3R,4R)-4-[[2-(acetoxy)ethyl]thio]-3-[[[(2-chloroacetylamino-4-thiazolyl)(methoxyimino)]acetyl]amino]-2-azetidinone.

IR $\nu_{max}^{KBr}$ cm$^{-1}$: 3260, 1765, 1736, 1668, 1546, 1260, 1226, 1052.

NMR(DMSO-d₆,ppm) δ: 2.00(s, CH₃), 2.79(t, J=7 Hz, —CH₂—), 3.89(s, CH₃), 4.14(t, J=7 Hz, —CH₂—), 4.32(s, —CH₂—), 5.06(d, J=5 Hz, C₄—H), 5.37(dd, J=5,8 Hz, C₃—H), 7.46(s,

8.80(s, NH), 9.47(d, J=8 Hz, NH), 12.92(s, NH).

REFERENCE EXAMPLE 18

To a solution of 1.07 g (2.55 mmol) of (3R,4R)-4-[[(aminocarbonyl)methyl]thio]-3-tritylamino-2-azetidinone obtained in Reference Example 9 in 20 ml of acetone is added 0.606 g (3.19 mmol) of p-toluenesulfonic acid monohydrate, and the mixture is stirred at room temperature for 40 minutes. The acetone is then distilled off under reduced pressure and the residue is triturated with diethyl ether and the resulting powder is collected by filtration. To a solution of the obtained powder in 6 ml of DMF is added 0.238 g (3 mmol) of pyridine under ice-cooling, and the mixture is stirred for 15 minutes.

To a solution of 2.28 g (3.5 mmol) of [[[1-(2-trimethylsilylethoxycarbonyl)-1-methylethoxy]imino](2-tritylamino-4-thiazolyl)]acetic acid hydrochloride in 15 ml of DMF is added 0.238 g (3 mmol) of pyridine under ice-cooling, and the mixture is stirred for 20 minutes. After addition of 0.536 g (3.5 mmol) of N-hydroxybenzotriazole and 0.877 g (4.25 mmol) of DCC (dicyclohexylcarbodiimide), the mixture is stirred at room temperature for one hour. The previously prepared solution is added to this solution, and the whole mixture is further stirred at room temperature for 5 hours. An insoluble material is filtered off and the filtrate is concentrated under reduced pressure. To the residue is added 50 ml of ethyl acetate and the mixture is washed with saturated aqueous sodium hydrogen carbonate and saturated aqueous sodium chloride, dried over anhydrous magnesium sulfate. The solvent is then distilled off under reduced pressure and the residue is purified by silica gel column chromatography using ethyl acetate-chloroform-methanol (10:10:1) to give 1.23 g (1.59 mmol) of (3R,4R)-4-[[(aminocarbonyl)methyl]thio]-3-[[[[1-(2-trimethylsilylethoxycarbonyl)-1-methylethoxy]imino](2-tritylamino-4-thiazolyl)]acetyl]amino]-2-azetidinone.

IR $\nu_{max}^{KBr}$ cm⁻¹: 3280, 2955, 1772, 1735, 1675, 1528.
NMR (DMSO-d₆, ppm) δ: 0.03(s, (CH₃)₃), 0.95(m, —CH₂—), 1.41(s, CH₃, CH₃), 3.15(s, —CH₂—), 4.13(m, —CH₂—), 5.11(d, J=5 Hz, C₄—H), 5.33(dd, J=5, 8 Hz, C₃—H), 6.79 (s,

7.16-7.50(m, arom H), 8.73(s, NH), 9.12(d, J=8 Hz, NH).

The following compounds are obtained according to the same manner as described above:
(3R,4R)-4-[[2-[(Chloroacetylamino)carboxy]ethyl]thio]-3-[[[[1-(2-trimethylsilylethoxycarbonyl)-1-methylethoxy]imino](2-tritylamino-4-thiazolyl)]acetyl]amino]-2-azetidinone.

IR $\nu_{max}^{KBr}$ cm⁻¹: 3275, 1775-1755, 1725, 1518, 1200.
NMR (DMSO-d₆, ppm) δ: 0.03(s, (CH₃)₃), 0.93(m, —CH₂—), 1.40(s, CH₃, CH₃), 2.80(m, —CH₂—), 3.99-4.30(m, —CH₂—, —CH₂—), 4.45(s, —CH₂—), 5.11(d, J=5 Hz, C₄—H), 5.30(dd, J=5, 9 Hz, C₃—H), 6.75(s,

7.13-7.50 (m, arom H), 8.73(s, NH), 8.77(s, NH), 9.05(d, J=9 Hz, NH), 10.93(br.s, NH).

(3S,4R)-4-Azido-3-[[[[1-(2-trimethylsilylethoxycarbonyl)-1-methylethoxy]imino](2-tritylamino-4-thiazolyl)]acetyl]amino]-2-azetidinone
IR $\nu_{max}^{KBr}$ cm⁻¹: 3350, 3280, 2112, 1780, 1730, 1675, 1520.
NMR (CDCl₃, ppm) δ: 0.03(s, (CH₃)₃), 1.95(s, CH₃), 1.97(s, CH₃), 4.21(t, J=9 Hz, —CH₂—), 5.33(d, J=4 Hz, C₄—H), 5.56(dd, J=4, 8 Hz, C₃—H), 6.75(s,

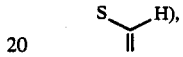

6.83(s, NH), 6.93(s, NH), 7.31(s, arom H), 8.15 (d, J=8 Hz, NH).

(3R,4S)-4-Azido-3-[[[[1-(2-trimethylsilylethoxycarbonyl)-1-methylethoxy]imino](2-tritylamino-4-thiazolyl)]acetyl]amino]-2-azetidinone
IR $\nu_{max}^{KBr}$ cm⁻¹: 3290, 2105, 1785, 1730, 1678, 1522, 1150.
NMR (DMSO-d₆, ppm) δ: 0.03(s, (CH₃)₃), 0.94(t, J=8 Hz, —CH₂—), 1.40(s, CH₃, CH₃), 4.13(t, J=8 Hz, —CH₂—) 4.57(dd, J=2, 8 Hz, C₃—H), 4.92(d, J=2 Hz, C₄—H), 6.70 (s,

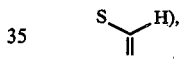

7.10-7.50(m, arom H), 8.74(s, NH), 8.98 (d, J=8 Hz, NH), 9.00 (s, NH).

(3R,4R)-4-Azido-3-[[[[(2-trimethylsilylethoxycarbonyl)methoxyimino](2-tritylamino-4-thiazolyl)-]acetyl]amino]-2-azetidinone
IR $\nu_{max}^{KBr}$ cm⁻¹: 3275, 2950, 2110, 1785, 1735, 1680, 1515, 1250.
NMR (DMSO-d₆, ppm) δ: 0.05(s, (CH₃)₃), 0.98(t, J=8 Hz, —CH₂—), 4.19(t, J=8 Hz, —CH₂—), 4.60(s, —CH₂—), 5.28(dd, J=4, 8 Hz, C₃—H), 5.33(d, J=4 Hz, C₄—H), 6.76(s,

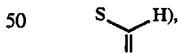

7.18-7.43(m, arom H), 8.74(s, NH), 8.98(s, NH), 9.31(d, J=8 Hz, NH).

(3R,4S)-4-Azido-3-[[[[(2-trimethylsilylethoxycarbonyl)methoxyimino](2-tritylamino-4-thiazolyl)]acetyl]amino]-2-azetidinone
IR $\nu_{max}^{KBr}$ cm⁻¹: 3270, 2955, 2110, 1782, 1740, 1680, 1527, 1250, 1228
NMR (DMSO-d₆, ppm) δ: 0.04(s, (CH₃)₃), 0.97(t, J=8 Hz, —CH₂—), 4.18(t, J=8 Hz, —CH₂—), 4.55(dd, J=2, 8 Hz, C₃—H), 4.60(s, —CH₂—), 4.91(d, J=2 Hz, C₄—H), 6.87(s, NH), 7.17-7.40(m, arom H), 8.74(s, NH), 8.99(s, NH), 9.12(d, J=8 Hz, NH).

REFERENCE EXAMPLE 19

To a solution of 4 g of (3R,4R)-4-[[(acetylamino)ethyl]thio]-3-tritylamino-2-azetidinone obtained in Reference Example 1 in 25 ml of acetone is added 1.71 g of p-toluenesulfonic acid monohydrate, and the mixture is stirred for one hour. The solvent is distilled off and the residue is washed with diethyl ether. The resulting powder is dissolved in a mixture of tetrahydrofuran (30 ml) and water (50 ml) and, under ice-cooling, a solution of 2.323 g of p-nitrobenzyloxycarbonyl chloride in 30 ml of tetrahydrofuran is added dropwise, with the solution being maintained at pH 8.5 with aqueous sodium hydrogen carbonate. The mixture is stirred at room temperature for one hour and treated with ethyl acetate and water. The organic layer is separated, wahsed with water and concentrated. The residue is purified by silica gel column chromatography using chloroform-ethyl acetate-methanol (3:3:1). The earlier eluate fractions are combined and concentrated under reduced pressure to give 1.169 g of (3R,4S)-4-[[(acetylamino)ethyl]thio]-3-(p-nitrobenzyloxy)carboxamido-2-azetidinone. The later eluate fractions are combined and concentrated under reduced pressure to give 0.877 g of (3R,4R)-4-[[(acetylamino)ethyl]thio]-3-(p-nitrobenzyloxy)carboxamido-2-azetidinone.

(3R,4S) derivative; IR $\nu_{max}^{KBr}$ cm$^{-1}$: 3280, 1760 1710, 1650, 1510, 1343, 1250.

(3R,4R) derivative; IR $\nu_{max}^{KBr}$ cm$^{-1}$: 3300, 1738, 1698, 1638, 1543, 1503, 1350, 1260, 1061.

EXAMPLE 1

(1) A solution of 0.450 g of sulfuric anhydride-DMF complex in 1.76 ml of DMF is added to a solution of 0.920 g of (3R,4R)-4-[[[(p-nitrobenzyloxy)carbonylamino]ethyl]thio]-3-[[[[(2-trimethylsilylethoxycarbonyl-1-methylethoxy)imino](2-tritylamino-4-thiazolyl)]acetyl]amino]-2-azetidinone in 5 ml of DMF at −70° C., and the reaction mixture is allowed to stand at −4° C. for 3 days. Pyridine (0.232 g) and then diethyl ether are added to the mixture and the oily product, which separates out, is collected by decantation and washed with diethyl ether. The oily product is dissolved in water and to the solution is added Dowex 50W resin (Na+-form, produced by Dow Chemical Co., U.S.A.), followed by stirring. After removal of the resin by filtration, the filtrate is further purified on an XAD-II resin column. The fractions containing the desired compound are combined, concentrated and lyophilized to give 0.870 g of sodium (3R,4R)-4-[-[[(p-nitrobenzyloxy)carbonylamino]ethyl]thio]-3-[[[[(2-trimethylsilylethoxycarbonyl-1-methylethoxy)imino](2-tritylamino-4-thiazolyl)]acetyl]amino]-2-azetidinone-1-sulfonate.

IR $\nu_{max}^{KBr}$ cm$^{-1}$: 3300, 2950, 1780, 1723, 1680, 1594, 1570, 1517, 1347, 840, 755.

NMR (DMSO-d$_6$, ppm) δ: 0.04(s, CH$_3$), 0.96(dd, J=7 Hz, —CH$_2$—), 2.7–3.0, 3.1–3.4(m, —CH$_2$—), 5.16(s, —CH$_2$—) 5.20(d, J=4 Hz, C$_4$—H), 5.34(dd, J=4, 8 Hz, C$_3$—H), 6.96 (s,

7.1–7.5(m, arom H), 7.58, 8.20(d, J=9 Hz, arom H), 9.24(m, NH), 9.42(d, J=8 Hz, NH).

(2) To a solution of 0.850 g of the above sodium (3R,4R)-4-[[[(p-nitrobenzyloxy)carbonylamino]ethyl]thio]-3-[[[[(2-trimethylsilylethoxycarbonyl-1-methylethoxy)imino](2-tritylamino-4-thiazolyl]acetyl]amino]-2-azetidinone-1-sulfonate in 10 ml of DMF is added 1.031 g of tetra-n-butylammonium fluoride trihydrate. The reaction mixture is stirred at room temperature for 7 minutes and treated with ethyl acetate and water, and the organic layer is separated and washed with water. The solvent is then distilled off and the residue is dissolved in a mixture of 25 ml of methanol and 3 ml of water. To the solution is added 4.9 ml of 1N hydrochloric acid and the mixture is stirred at room temperature for 8 hours, followed by addition of 0.412 g of sodium hydrogen carbonate. The methanol is distilled off and the residue is chromatographed on an XAD-II column to give 0.140 g of sodium (3R,4R)-3-[[[(2-amino-4-thiazolyl)[(1-carboxy-1-methylethoxy)imino]]acetyl]amino]-4-[[[(p-nitrobenzyloxy)carbonylamino]ethyl]-thio]-2-azetidinone-1-sulfonate.

IR $\nu_{max}^{KBr}$ cm$^{-1}$: 3350, 1760, 1700, 1670, 1600, 1518, 1250, 1048.

NMR (DMSO-d$_6$, ppm) δ: 1.40, 1.48(s, CH$_3$), 2.6–3.0 (m, —CH$_2$—), 3.1–3.5(m, —CH$_2$—), 5.16(s, —CH$_2$—), 5.20(d, J=5 Hz, C$_4$—H), 5.35(dd, J=5, 8 Hz, C$_3$—H), 6.77 (s,

7.11(br.s, NH$_2$), 7.47(br.s, NH), 7.60, 8.22(d, J=9 Hz, arom H), 11.18(d, J=8 Hz, NH).

(3) To a solution of 0.300 g of the above sodium (3R,4R)-3-[[[(2-amino-4-thiazolyl)[(1-carboxy-1-methylethoxy)imino]]acetyl]amino]-4-[[[(p-nitrobenzyloxy)carbonylamino]ethyl]thio]-2-azetidinone-1-sulfonate in a mixture of THF (15 ml) and H$_2$O (15 ml) is added 6 ml of Dowex 50W resin (H+-form, produced by Dow Chemical Co., U.S.A.), followed by stirring at room temperature for 20 minutes. After removal of the resin by filtration, 300 mg of 10% palladium-carbon is added to the filtrate, and the mixture is stirred vigorously in a hydrogen gas stream for an hour. The organic solvent is then distilled off and the aqueous residue is chromatographed on an XAD-II column to give 0.065 g of (3R,4R)-4-[(aminoethyl)thio]-3-[[[(2-amino-4-thiazolyl)[(1-carboxy-1-methylethoxy)imino]]acetyl]amino]-2-azetidinone-1-sulfonic acid.

IR $\nu_{max}^{KBr}$ cm$^{-1}$: 3380, 1772, 1670, 1630, 1525, 1255, 1048.

NMR (DMSO-d$_6$, ppm)δ: 1.45(s, CH$_3$), 5.26(d, J=6 Hz, C$_4$—H), 5.36(dd, J=6, 8 Hz, C$_3$—H), 6.82(s,

9.20(d, J=8 Hz, HN).

EXAMPLE 2

A solution of 0.231 g of sulfuric anhydride-DMF complex in 0.9 ml of DMF is added to a solution of 0.230 g of (3R,4R)-3-[[[(2-chloroacetylamino-4-thiazolyl)methoxyimino]acetyl]amino]-4-(sulfamoyl)-2-azetidinone in 3 ml of DMF at −70° C., and the reaction mixture is allowed to stand at −2° C. for 30 hours. After addition of 0.119 g of pyridine, the mixture is further treated in the same manner as described in Example 1-(1). The first eluate fractions give 0.035 g of disodium (3R,4R)-3-[[[(2-chloroacetylamino-4-thiazolyl)methoxyimino]acetyl]amino]-4-[(N-sulfonato)sulfamoyl]-2-azetidinone-1-sulfonate.

IR $\nu_{max}^{KBr}$ cm$^{-1}$: 3220, 1783, 1720, 1670, 1540, 1380, 1325, 1250, 1160, 1050, 890.

NMR (DMSO-d$_6$, ppm) δ: 3.88(s, OCH$_3$), 4.37(s, ClCH$_2$—), 5.03(d, J=5 Hz, C$_4$—H), 5.70(dd, J=5, 9 Hz, C$_3$—H), 7.55(s,

H), 9.30(d, J=9 Hz, NH).

The subsequent eluate fractions give 0.090 g of sodium (3R,4R)-3-[[[(2-chloroacetylamino-4-thiazolyl)-methoxyimino]acetyl]amino]-4-[(N-sulfonato)sulfamoyl]-2-azetidinone.

IR $\nu_{max}^{KBr}$ cm$^{-1}$: 3220, 1780, 1674, 1542, 1322, 1257, 1155, 1043.

NMR (DMSO-d$_6$, ppm) δ: 3.88(s, OCH$_3$), 4.37(s, ClCH$_2$—), 5.26(d, J=5 Hz, C$_4$—H), 5.60(dd, J=5, 9 Hz, C$_3$—H), 7.58 (s, arom H), 8.92(br.s, NH), 9.28(d, J=9 Hz, NH).

The further eluate fractions give 0.022 g of sodium (3R,4R)-3-[[[(2-chloroacetylamino-4-thiazolyl)methoxyimino]acetyl]amino]-4-sulfamyoyl-2-azetidinone-1-sulfonate.

IR $\nu_{max}^{KBr}$ cm$^{-1}$: 3220, 1783, 1674, 1540, 1340, 1280, 1247, 1152, 1043.

NMR(DMSO-d$_6$, ppm)δ: 3.87(s, OCH$_3$), 4.36(s, ClCH$_2$—), 5.03(d, J=5 Hz, C$_4$—H), 5.70(dd, J=5, 9 Hz, C$_3$—H), 7.54(s,

H), 9.30(d, J=9 Hz, NH).

EXAMPLE 3

(1) To a solution of (3R,4R)-4-[[2-(acetoxy)ethyl]thio]-3-[[[(2-chloroacetylamino-4-thiazolyl)(methoxyimino)]acetyl]amino]-2-azetidinone (0.64 g) obtained in Reference Example 14 in 4 ml of DMF is added 2.48 ml of a DMF solution containing 0.634 g of sulfuric anhydride-DMF complex at −70° C., and the reaction mixture is allowed to stand at 0° C. for 4 days. After addition of 0.328 g of pyridine, the mixture is concentrated to 2 ml under reduced pressure. After addion of diethyl ether, the resulting oil is collected by decantation and washed with diethyl ether. The residue is dissolved in 20 ml of 50% ethanol, followed by addition of 12 ml of Dowex 50W resin (Na$^+$-form) and the mixture is stirred at room temperature for 30 minutes. The resin is then filtered off and the filtrate is subjected to distillation to remove ethanol. The residue is chromatographed on a column of XAD-II resin to give 0.694 g (1.22 mol) of sodium (3R,4R)-4-[[2-(acetoxy)ethyl]thio]-3-[[[(2-chloroacetylamino-4-thiazolyl)(methoxyimino)-]acetyl]amino]-2-azetidinone-1-sulfonate.

IR$\nu_{max}^{KBr}$ cm$^{-1}$: 3405, 3265, 1770, 1730, 1665, 1540, 1255-1230, 1050, 1035.

NMR (DMSO-d$_6$, ppm)δ: 2.02(s, CH$_3$), 3.00(m, —CH$_2$—), 3.88(s, CH$_3$), 4.18(t, —CH$_2$—), 4.36(s, —CH$_2$), 5.25(d, J=5 Hz, C$_4$—H), 5.38(dd, J=5, 8 Hz, C$_3$—H), 7.48(s,

H), 9.50(d, J=8 Hz, NH).

The following compounds are obtained according to the same manner as described above:

(2) Sodium (3R,4S)-4-[[2-(acetoxy)ethyl]thio]-3-[[[(2-chloroacetylamino-4-thiazolyl)(methoxyimino)-]acetyl]amino]-2-azetidinone-1-sulfonate IR$\nu_{max}^{KBr}$ cm$^{-1}$: 3440, 3240, 1768, 1728, 1665, 1540, 1250-1230, 1040.

NMR (DMSO-d$_6$, ppm)δ: 2.01(s, CH$_3$), 3.03(m, —CH$_2$—), 4.20(t. J=7 Hz, —CH$_2$—), 4.35(s, —CH$_2$—), 4.69 (dd, J=2, 8 Hz, C$_3$—H), 4.92(d, J=2 Hz, C$_4$—H), 7.40(s,

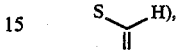

H), 9.50(d, J=8 Hz, NH), 12.95(br.s, NH).

(3) Sodium (3R,4R)-3-[[[(2-chloroacetylamino-4-thiazolyl)(methoxyimino)]acetyl]amino]-4-[[E-2-(ethoxycarbonyl)ethenyl]thio]-2-azetidinone-1-sulfonate IR$\nu_{max}^{KBr}$ cm$^{-1}$: 3430, 3250, 1775, 1692, 1580, 1540, 1255, 1044.

NMR (DMSO-d$_6$, ppm)δ: 1.20(t, J=7 Hz, CH$_3$), 3.88(s, CH$_3$), 4.10(q, J=7 Hz, —CH$_2$—), 4.26(s, —CH$_2$—), 5.40-5.62 (m, C$_3$—H, C$_4$—H), 5.93(d, J=16 Hz,

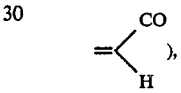

), 7.35(s,

H), 7.82(d, J=16 Hz,

), 9.54(d, J=8 Hz,, NH) 12.95 (br.s, NH).

(4) Sodium (3R,4S)-3-[[[(2-chloroacetylamino-4-thiazolyl)(methoxyimino)]acetyl]amino]-4-[[E-2-(ethoxycarbonyl)ethenyl]thio]-2-azetidinone-1-sulfonate IR$\nu_{max}^{KBr}$ cm$^{-1}$: 3440, 3250, 1780, 1690, 1678, 1546, 1255, 1045.

NMR (DMSO-d$_6$, ppm)δ: 1.20(t, J=7 Hz, CH$_3$), 3.92(s, CH$_3$), 4.11(q, J=7 Hz, —CH$_2$—), 4.37(s, —CH$_2$—), .4.81 (dd, J=2, 8 Hz, C$_3$—H), 5.16(d, J=2 Hz, C$_3$—H), 5.96 (d, J=16 Hz,

), 7.43(s,

H), 7.83 (d, J=16 Hz,

9.58(d, J=8 Hz, NH).

(5) Sodium (3S,4R)-3-[[[(2-chloroacetylamino-4-thiazolyl)(methoxyimino)]acetyl]amino]-4-[4-(ethoxycarbonyl)-1,2,3-triazol-1-yl]-2-azetidinone-1-sulfonate IR$\nu_{max}^{KBr}$ cm$^{-1}$: 3450, 3210, 3104, 2990, 1795, 1725, 1665, 1550, 1270–1245, 1055, 1040.

NMR (DMSO-d$_6$, ppm)δ: 1.35(t, J=7 Hz, CH$_3$), 3.94(s, CH$_3$), 4.33(s, —CH$_2$—), 4.33(q, J=7 Hz, —CH$_2$—), 5.42(dd, J=2, 8 Hz, C$_3$—H), 6.28(d, J=2 Hz, C$_4$—H), 7.45 (s,

9.09(s,

9.65(d, J=8 Hz, NH).

(6) Sodium (3S,4R)-3-[[[(2-chloroacetylamino-4-thiazolyl)(methoxyimino)]acetyl]amino]-4-]5-(ethoxycarbonyl)-1,2,3-triazol-1-yl]-2-azetidinone-1-sulfonate IR$\nu_{max}^{KBr}$ cm$^{-1}$: 3440, 3230, 2980, 1790, 1725, 1670, 1543, 1260, 1145.

NMR (DMSO-d$_6$, ppm)δ: 1.34(t, J=7 Hz, CH$_3$), 3.92(s, CH$_3$), 4.33(s, —CH$_2$—), 4.37(q, J=7 Hz, —CH$_2$—), 5.85(dd, J=2, 8 Hz, C$_3$—H), 6.86(d, J=2 Hz, C$_4$—H), 7.42 (s,

8.27(s,

9.74(d, J=8 Hz, NH), 12.90(br.s, NH).

(7) Sodium (3S,4S)-3-[[[(2-chloroacetylamino-4-thiazolyl)(methoxyimino)]acetyl]amino]-4-[5-(methoxycarbonyl)-1,2,3-triazol-1-yl]-2-azetidinone-1-sulfonate IR$\nu_{max}^{KBr}$ cm$^{-1}$: 3450–3440, 3250, 1790, 1725, 1665, 1545, 1280, 1265, 1050.

NMR (DMSO-d$_6$, ppm)δ: 3.66(s, CH$_3$), 3.91(s, CH$_3$), 4.33(s, —CH$_2$—), 5.72(dd, J=5, 8 Hz, C$_3$—H), 7.11 (d, J=5 Hz, C$_4$—H), 7.14(s,

8.35(s,

9.38(d, J=8 Hz, NH).

(8) Sodium (3R,4S)-4-[[(2-[(chloroacetylamino)carboxy]ethyl]thio]-3-[[[(2-chloroacetylamino-4-thiazolyl)-(methoxyimino)]acetyl]amino]-2-azetidinone-1-sulfonate IR$\nu_{max}^{KBr}$ cm$^{-1}$: 3475, 3250, 1773, 1668, 1545–1525, 1255, 1206, 1042.

NMR(DMSO-d$_6$, ppm)δ: 3.05(m, —CH$_2$—), 4.27(t, J=7 Hz, —CH$_2$—), 4.33(s, —CH$_2$—), 4.42(s, —CH$_2$—), 4.65 (dd, J=3, 9 Hz, C$_3$—H), 4.90(d, J=3 Hz, C$_4$—H), 7.39 (s,

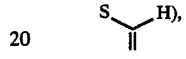

9.47(d, J=9 Hz, NH), 10.93(s, NH), 12.99(br.s, NH).

(9) Sodium (3R,4R)-4-[[2-[(chloroacetylamino)carboxy]ethyl]thio]-3-[[[(2-chloroacetylamino-4-thiazolyl)-(methoxyimino)]acetyl]amino]-2-azetidinone-1-sulfonate IR$\nu_{max}^{KBr}$ cm$^{-1}$: 3450, 3250, 1775, 1675, 1645–1620, 1255, 1042.

NMR(DMSO-d$_6$, ppm)δ: 3.08(m, —CH$_2$—), 3.88(s, CH$_3$), 4.28(t, J=7 Hz, —CH$_2$—), 4.33 (s, —CH$_2$—), 4.45(s, —CH$_2$—), 5.25–5.50(m, C$_3$—H, C$_4$—H), 7.47(s,

9.52(d, J=8 Hz, NH), 11.00(s, NH), 12.90(br.s, NH).

EXAMPLE 4

(1) To a solution of 0.57 g of (3R,4S)-4-[[(aminocarbonyl)methyl]thio]-3-[[[(2-chloroacetylamino-4-thiazolyl)(methoxyimino)]acetyl]amino]-2-azetidinone obtained in Reference Example 16-(1) in 4 ml of DMF is added 1.70 ml of a DMF solution containing 0.435 g of sulfuric anhydride-DMF complex at −70° C., and the reaction mixture is allowed to stand at 0° C. for 2 days. Pyridine (0.225 g) is added to the reaction mixture and the mixture is further treated in the same manner as described in Example 1-(1). The earlier eluate fractions give 0.199 g of disodium (3R,4S)-3-[[[(2-chloroacetylamino-4-thiazolyl)(methoxyimino)]acetyl]amino]-4-[[(sulfonatoaminocarbonyl)methyl]thio]-2-azetidinone-1-sulfonate.

IR$\nu_{max}^{KBr}$ cm$^{-1}$: 3470, 3200, 1773, 1660, 1545, 1270–1220, 1040.

NMR (DMSO-d$_6$+D$_2$O, ppm)δ: 3.28(ABq, J=15 Hz, —CH$_2$—), 4.10(s, CH$_3$), 4.55, 4.60(each s, —CH$_2$—), 4.93(d, J=2 Hz, C$_3$—H), 5.24(d, J=2 Hz, C$_4$—H), 7.65(s,

The later eluate fractions give 0.286 g of a mixture of sodium (3R,4S)-4-[[(aminocarbonyl)methyl]thio]-3-[[[(2-chloroacetylamino-4-thiazolyl)(methoxyimino)-]acetyl]amino]-2-azetidinone-1-sulfonate and sodium (3R,4S)-3-[[[(2-chloroacetylamino-4-thiazolyl)(methoxyimino)]acetyl]amino]-4-[[(sulfonatoaminocarbonyl)methyl]thio]-2-azetidinone.

IR$\nu_{max}^{KBr}$ cm$^{-1}$: 3245, 1762, 1668, 1546, 1260–1240, 1041,

NMR (DMSO-d$_6$+D$_2$O, ppm)δ: 3.55(m, —CH$_2$—), 4.12(s, CH$_3$), 4.54, 4.58(each s, —CH$_2$—), 4.85, 4.92(each d, J=2 Hz, C$_3$—H), 5.08, 5.25(each d, J=2 Hz, C$_4$—H), 7.65(s,

The following compounds are obtained according to the same manner as described above:

(2) Disodium (3R,4R)-3-[[[(2-chloroacetylamino-4-thiazolyl)(methoxyimino)]acetyl]amino]-4-[[(sulfonatoaminocarbonyl)methyl]thio]-2-azetidinone-1-sulfonate (compound A)

Compound A; IR$\nu_{max}^{KBr}$ cm$^{-1}$: 3450, 3260, 1773, 1660, 1546, 1232, 1185, 1045.

NMR (DMSO-d$_6$, ppm)δ: 3.50(m, —CH$_2$—), 3.87(s, —CH$_3$), 4.36(s, —CH$_2$—), 5.30–5.50(m. C$_3$—H, C$_4$—H), 7.49 (s,

9.60(m, NH), 10.07(br.s, NH) and sodium (3R,4R)-4-[[(aminocarbonyl)methyl]thio]-3-[[[(2-chloroacetylamino-4-thiazolyl)(methoxyimino)]acetyl]amino]-2-azetidinone-1-sulfonate (compound B).

Compound B: IR$\nu_{max}^{KBr}$ cm$^{-1}$: 3400, 3275, 1765, 1660, 1540, 1260, 1050.

NMR (DMSO-d$_6$, ppm)δ: 3.38(ABq, J=14 Hz, —CH$_2$—), 3.89(s, CH$_3$), 4.35(s, —CH$_2$—), 5.18(d, J=5 Hz, C$_4$—H), 5.41(dd, J=5, 8 Hz, C$_3$—H), 7.07(br.s, NH), 7.43(br.s, NH), 7.54(s,

9.63(d, J=8 Hz, NH), 12.85(br.s, NH).

EXAMPLE 5

(1) To a solution of 0.60 g (1.06 mmol) of sodium (3R,4R)-4-[[2-acetoxy)ethyl]thio]-3-[[[(2-chloroacetylamino-4-thiazolyl)(methoxyimino)]acetyl]amino]-2-azetidinone-1-sulfonate obtained in Example 3-(1) in 15 ml of 50% aqueous methanol is added 0.172 g of sodium monomethylaminodithiocarbamate under ice-cooling, and the mixture is stirred at room temperature for 1.5 hours. The methanol is then distilled off under reduced pressure and the insoluble material is filtered off. The filtrate is chromatographed on a column of XAD-II resin to give 0.383 g of sodium (3R,4R)-4-[[2-(acetoxy)ethyl]thio]-3-[[[(2-amino-4-thiazolyl)(methoxyimino]acetyl]amino]-2-azetidinone-1-sulfonate.

IR$\nu_{max}^{KBr}$ cm$^{-1}$: 3410, 3330, 1770, 1725, 1665, 1615, 1530, 1250, 1050.

NMR (DMSO-d$_6$, ppm)δ: 2.00(s, CH$_3$), 3.00(m, —CH$_2$—), 3.83(s, CH$_3$), 4.17(t, J=7 Hz, —CH$_2$—), 5.23 (d, J=5 Hz, C$_4$—H), 5.33(dd, J=5, 8 Hz, C$_3$—H), 6.87 (s,

7.16(s, NH$_2$), 9.45(d, J=8 Hz, NH).

The following compounds are obtained according to the same manner as described above:

(2) Sodium (3R, 4S)-4-[[2-(acetoxy)ethyl]thio]-3-[[[(2-amino-4-thiazolyl)(methoxyimino)]acetyl]amino]-2-azetidinone-1-sulfonate.

IR$\nu_{max}^{KBr}$ cm$^{-1}$: 3410, 3315, 1765, 1726, 1665, 1612, 1526, 1250, 1046.

NMR (DMSO-d$_6$, ppm)δ: 2.00(s, CH$_3$), 2.70–3.20 (m, —CH$_2$—), 3.85(s, CH$_3$), 4.19(t, J=7 Hz, —CH$_2$—), 4.64(dd, J=3, 9 Hz, C$_3$—H), 4.92(d, J=3 Hz, C$_4$—H), 6.70 (s,

7.18(s, NH$_2$), 9.38(d, J=9 Hz, NH).

(3) Sodium (3R, 4R)-3-[[[(2-amino-4-thiazolyl)(methoxyimino)]acetyl]amino]-4-[[E-2-(ethoxycarbonyl)ethenyl]thio]-2-azetidinone-1-sulfonate IR$\nu_{max}^{KBr}$ cm$^{-1}$: 3410, 3330, 1780, 1690, 1660, 1585, 1520, 1250, 1050.

NMR (DMSO-d$_6$, ppm)δ: 1.21(t, J=7 Hz, CH$_3$), 3.82(s, CH$_3$), 4.10(q, J=7 Hz, —CH$_2$—), 5.44(dd, J=5, 8 Hz, C$_3$—H), 5.56 (d, J=5 Hz, C$_4$—H), 5.92(d, J=16 Hz,

6.68(s,

7.16(s, NH$_2$), 7.81(d, J=16 Hz,

9.43 (d, J=8 Hz, NH).

(4) Sodium (3S, 4R)-3-[[[(2-amino-4-thiazolyl)(methoxyimino)]acetyl]amino]-4-[4-(ethoxycarbonyl)-1,2,3-triazol-1-yl]-2-azetidinone-1-sulfonate IR$\nu_{max}^{KBr}$ cm$^{-1}$: 3420, 3350, 1795, 1725, 1665, 1620, 1530, 1255, 1052.

NMR (DMSO-d$_6$, ppm)δ: 1.34(t, J=7 Hz, CH$_3$), 3.88(s, CH$_3$) 4.34(q, J=7 Hz, —CH$_2$—), 5.36(dd, J=2, 8 Hz, C$_3$—H), 6.27 (d, J=2 Hz, C$_4$—H), 6.77(s,

7.20(br.s, NH$_2$), 9.10(s,

9.57 (d, J=8 Hz, NH).

(5) Sodium (3S, 4R)-3-[[[(2-amino-4-thiazolyl)(methoxyimino)]acetyl]amino]-4-[5-(ethoxycarbonyl)-1,2,3-triazol-1-yl]-2-azetidinone-1-sulfonate IR$\nu_{max}^{KBr}$ cm$^{-1}$: 3420, 1788, 1725, 1660, 1610, 1530, 1270, 1050.

NMR (DMSO-d$_6$, ppm)δ: 1.33(t, J=7 Hz, CH$_3$), 3.86(s, CH$_3$), 4.36(q, J=7 Hz, —CH$_2$—), 5.57(dd, J=2, 8 Hz, C$_3$—H), 6.73 (s,

6.86(d, J=2 Hz, C$_4$—H), 7.15(br.s, NH$_2$), 8.27(s,

9.63(d, J=8 Hz, NH).

(6) Sodium (3S, 4S)-3-[[[(2-amino-4-thiazolyl)(methoxyimino)]acetyl]imino]-4-[5-(methoxycarbonyl)-1,2,3-triazol-1-yl]-2-azetidinone-1-sulfonate IR$\nu_{max}^{KBr}$ cm$^{-1}$: 3400, 1785, 1725, 1672, 1615, 1525, 1265, 1053.

NMR (DMSO-d$_6$, ppm)δ: 3.61(s, CH$_3$), 3.89(s, CH$_3$), 5.65 (dd, J=5, 8 Hz, C$_3$—H), 6.30(s,

7.06(d, J=5 Hz, C$_4$—H), 7.09(s, NH$_2$), 8.32(s,

9.24 (d, J=8 Hz, NH).

(7) A mixture of sodium (3R, 4S)-4-[[(aminocarbonyl)methyl]thio]-3-[[[(2-amino-4-thiazolyl)(methoxyimino)]acetyl]amino]-2-azetidinone-1-sulfonate and sodium (3R, 4S)-3-[[[(2-amino-4-thiazolyl)(methoxyimino)]acetyl]amino]-4-[[(sulfonatoaminocarbonyl)methyl]thio]-2-azetidinone IR$\nu_{max}^{KBr}$ cm$^{-1}$: 3500, 3275, 3200, 1757, 1660, 1525, 1235, 1040.

NMR (DMSO-d$_6$+D$_2$O, ppm)δ: 3.53(m, —CH$_2$—), 4,81, 4.88(each d, J=2 Hz, C$_3$—H), 5.10, 5.22(each d, J=2 Hz, C$_4$—H), 6.97(s,

(8) Disodium (3R, 4S)-3-[[[(2-amino-4-thiazolyl)(methoxyimino)]acetyl]amino]-4-[[(sulfonatoaminocarbonyl)methyl]thio]-2-azetidinone-1-sulfonate IR$\nu_{max}^{KBr}$ cm$^{-1}$: 3500–3180, 1770, 1665, 1626, 1240, 1045.

NMR (DMSO-d$_6$, ppm)δ: 3.49(m, —CH$_2$—), 3.93(s, CH$_3$), 4.77(dd, J=3, 9 Hz, C$_3$—H), 5.07(d, J=3 Hz, C$_4$—H), 7.03(s,

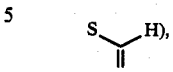

9.55(d, J=9 Hz, NH), 10.10(br. s, NH).

(9) Sodium (3R, 4R)-4-[[(aminocarbonyl)methyl]thio]-3-[[[(2-amino-4-thiazolyl)(methoxyimino)]acetyl]amino]-2-azetidinone-1-sulfonate IR$\nu_{max}^{KBr}$ cm$^{-1}$: 3425–3280, 1765, 1662, 1615, 1525, 1245, 1045.

NMR (DMSO-d$_6$, ppm)δ: 3.38(ABq, J=14 Hz, —CH$_2$—), 3.84(s, CH$_3$), 5.24–5.50(m, C$_3$—H, C$_4$—H), 6.88 (s,

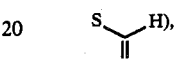

7.10(br.s, NH), 7.19(s, NH$_2$), 7.42(br.s, NH) 9.54(d, J=8 Hz, NH).

EXAMPLE 6

To a solution of 0.70 g of (3S, 4R)-3-[[[(2-chloroacetylamino-4-thiazolyl)(methoxyimino)]acetyl]amino]-4-[4-(methoxycarbonyl)-1,2,3-triazol-1-yl]-2-azetidinone obtained in Reference Example 14-(1) in 4 ml of DMF is added 5.86 ml of a DMF solution containing 1.49 g of sulfuric anhydride-DMF complex under cooling at −70° C., and the reaction mixture is allowed to stand at 0° C. for 18 days. After addition of 0.78 g of pyridine, the mixture is concentrated under reduced pressure. The resulting solid is collected by filtration, and washed with ethanol. The solid is dissolved in 4 ml of DMF, and after addition of 10 ml of Dowex 50W resin (Na$^+$-form), the mixture is stirred at room temperature for 30 minutes. The resin is then filtered off, 0.21 g of sodium monomthyldithiocarbamate is added to the filtrate under ice-cooling, and the mixture is stirred at room temperature for 1.5 hours and concentrated to 1.5 ml under reduced pressure. After addition of 6 ml of water, the insoluble material is filtered off. The filtrate is chromatographed on a column of XAD-II resin to give 0.366 g (0.73 mmol) of sodium (3S, 4S)-[[[(2-amino-4-thiazolyl)(methoxyimino)]acetyl]amino]-4-[4-(methoxycarbonyl)-1,2,3-triazol-1-yl]-2-azetidinone-2-azetidinone-1-sulfonate.

IR$\nu_{max}^{KBr}$ cm$^{-1}$: 3415, 3325, 1795, 1725, 1662, 1615, 1528, 1275, 1255, 1055, 1040.

NMR (DMSO-d$_6$, ppm)δ: 3.60(s, CH$_3$), 3.85(s, CH$_3$), 5.67(m, C$_4$—H), 6.13(s,

6.57(d, J=5 Hz, C$_4$—H), 7.12(s, NH$_2$), 8.62(s,

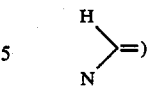

9.26 (m, NH).

EXAMPLE 7

(1) To a solution of 0.32 g of sodium (3R, 4S)-4-[[2-[(chloroacetylamino)carboxylethyl]thio]-3-[[[(2-chloroacetylamino-4-thiazolyl)(methoxyimino)]acetyl]amino]-2-azetidinone-1-sulfonate obtained in Example 3-(8) in 10 ml of 50% aqueous methanol is added 0.161 g of sodium monomethyldithiocarbamate under ice-cooling, and the reaction mixture is stirred at room temperature for 2 hours. The reaction mixture is further treated in the same manner as described in Example 5-(1) to obtain 0.133 g of (0.27 mmol) of sodium (3R, 4S)-4-[[2-(aminocarboxy)ethyl]thio]-3-[[[(2-amino-4-thiazolyl)(methoxyimino)]acetyl]amino]-2-azetidinone-1-sulfonate.

IR$\nu_{max}^{KBr}$ cm$^{-1}$: 3430-3300, 1760, 1705, 1660, 1605, 1522, 1270, 1245, 1042.

NMR (DMSO-d$_6$, ppm)$\delta$: 2.97(m, —CH$_2$—), 3.84(s, CH$_3$), 4.07(t, J=7 Hz, —CH$_2$—), 4.65(dd, J=3, 8 Hz, C$_3$—H), 4.89(d, J=3 Hz, C$_4$—H), 6.41(s, NH$_2$), 6.69(s,

H), 7.15(s, NH$_2$), 9.35(d, J=8 Hz, NH).

(2) By the same manner as described above, sodium (3R, 4R)-4-[[2-aminocarboxy)ethyl]thio]-3-[[[(2-amino-4-thiazolyl)(methoxyimino)]acetyl]amino]-2-azetidinone-1-sulfonate is obtained.

IR$\nu_{max}^{KBr}$ cm$^{-1}$: 3430, 3325, 1776, 1692, 1655, 1612, 1525, 1270, 1253, 1045.

NMR (DMSO-d$_6$, ppm)$\delta$: 2.95(m, —CH$_2$—), 3.85(s, CH$_3$), 4.07(t, J=7 Hz, —CH$_2$—), 5.22(d, J=5 Hz, C$_4$—H), 5.33(dd, J=5, 8 Hz, C$_3$—H), 6.39(s, NH$_2$), 6.85(s,

H), 7.13(s, NH$_2$), 9.42(d, J=8 Hz, NH).

EXAMPLE 8

(1) To a solution of 0.80 g of (3S, 4R)-4-azido-3-[[[[[1-(2-trimethylsilylethoxycarbonyl)-1-methylethoxy]imino](2-tritylamino-4-thiazolyl)]acetyl]amino]-2-azetidinone obtained in Reference Example 18-(3) in 4 ml of DMF is added 1.98 ml of a DMF solution containing 0.505 g of sulfuric anhydride-DMF complex is added under cooling at −70° C., and the reaction mixture is allowed to stand at 0° C. for 2 days. After addition of pyridine (0.26 g), the mixture is stirred at room temperature for 20 minutes, followed by concentration under reduced pressure. The resulting residue is washed with diethyl ether and dissolved in 20 ml of 50% aqueous ethanol. To the solution is added 0.508 g of sodium hydrogen carbonate under ice-cooling, and the mixture is stirred for 30 minutes. The ethanol is then distilled off and the residue is chromatographed on a column of XAD-II resin to obtain 0.673 g of sodium (3S, 4S)-4-azido3-[[[[[1-(2-trimethylsilylethoxycarbonyl)-1-methylethoxy]imino](2-tritylamino-4-thiazolyl)]acetyl]amino]-2-azetidinone-1-sulfonate.

IR$\nu_{max}^{KBr}$ cm$^{-1}$: 3380, 2115, 1778, 1728, 1676, 1512, 1282, 1245, 1050.

NMR (DMSO-d$_6$, ppm)$\delta$: 0.05(s, CH$_3$), 0.95(t, J=8 Hz, —CH$_2$—), 1.40(s, CH$_3$), 1.42(s, CH$_3$), 4.13(t, J=8 Hz, —CH$_2$—), 5.14(dd, J=5, 8 Hz, C$_3$—H), 5.44(d, J=5 Hz, C$_4$—H), 6.70(s,

H), 7.15-7.53 (m. arom H), 8.73(s, NH), 9.08(d, J=8 Hz, NH).

The following compounds are obtained according to the same manner as described above:

(2) Sodium (3S, 4R)-4-azido-3-[[[[[1-(2-trimethylsilylethoxycarbonyl)-1-methylethoxy]imino](2-tritylamino-4-thiazolyl)]acetyl]amino]-2-azetidinone-1-sulfonate IR$\nu_{max}^{KBr}$ cm$^{-1}$: 3360, 2110, 1782, 1730, 1662, 1522, 1182, 1250, 1150, 1050.

NMR (DMSO-d$_6$, ppm)$\delta$: 0.03(s, CH$_3$), 0.95(t, J=8 Hz, —CH$_2$—), 1.41(s, CH$_3$, CH$_3$), 4.14(t, J=8 Hz, —CH$_2$—), 4.48(dd, J=2, 8 Hz, C$_3$—H), 5.15(d, J=2 Hz, C$_4$—H), 6.70(s,

H), 7.15-7.50 (m, arom H), 8.40 (s, NH), 9.08(d, J=8 Hz, NH).

(3) Sodium (3S, 4S)-4-azido-3[[[[(2-trimethylsilylethoxycarbonyl)methoxyimino] (2-tritylamino-4-thiazolyl)]acetyl]amino]-2-azetidinone-1-sulfonate IR $\nu_{max}^{KBr}$ cm$^{-1}$: 3375, 2125, 1775, 1690, 1525, 1285, 1250, 1052.

NMR (DMSO-d$_6$, ppm)$\delta$: 0.06 (s, CH$_3$), 1.00 (t, J=8 Hz, —CH$_2$—), 4.20 (t, J=8 Hz, —CH$_2$—), 4.62 (s, —CH$_2$—), 5.14 (dd, J=5,8 Hz, C$_3$—H), 5.45 (d, J=8 Hz, C$_4$—H), 6.81 (s,

H), 7.20-7.46 (m, arom H), 8.85 (s, NH), 9.28 (d, J=8 Hz, NH).

(4) Sodium (3S, 4R)-4-azido-3-[[[[(2-trimethylsilylethoxycarbonyl)methoxyimino](2-tritylamino-4-thiazolyl)]acetyl]amino]-2-azetidinone-1-sulfonate IR $\nu_{max}^{KBr}$ cm$^{-1}$: 3410, 2115, 1780, 1735, 1675, 1528, 1270, 1250, 1052.

NMR (DMSO-d$_6$, ppm)$\delta$: 0.05 (s, CH$_3$), 0.98 (t, J=8 Hz, —CH$_2$—), 4.19 (t, J=8 Hz, —CH$_2$—), 4.46 (dd, J=2,8 Hz, C$_3$—H), 4.62 (s, —CH$_2$—), 5.18 (d, J=2 Hz, C$_4$—H), 6.78 (s,

H), 7.19-7.46 (m, arom H), 8.78 (s, NH), 9.28 (d, J=8 Hz, NH).

EXAMPLE 9

To a solution of (3R, 4R)-4-[[(aminocarbonyl)methyl]thio]-3-[[[[1-(2-trimethylsilylethoxycarbonyl)-1-methylethoxy]imino](2-tritylamino-4-thiazolyl)]acetyl]amino]-2-azetidinone obtained in Reference Example 18-(1) in 5 ml of DMF is added 2.14 ml of a DMF solution containing 0.547 g of sulfuric anhydride-DMF complex under cooling at −70° C., and the reaction mixture is allowed to stand at 0° C. for 2 days. After addition of 0.282 g of pyridine, the mixture is stirred at room temperature for 30 minutes. The solvent is then distilled off and the residue is washed with diethyl ether and dissolved in 20 ml of 50% aqueous ethanol. To the solution is added 0.547 g of sodium hydrogen carbonate under ice-cooling and the mixture is further treated in the same manner as described in Example 8-(1). The first eluate fractions give 0.385 g of disodium (3R, 4R)-3-[[[[[1-(2-trimethylsilylethoxycarbonyl)-1-methylethoxy]imino](2-tritylamino-4-thiazolyl)acetyl]amino]-4-[[(sulfonatoaminocarbonyl)methyl]thio]-2-azetidinone-1-sulfonate.

IR $\nu_{max}^{KBr}$ cm $-1$: 3470–3415, 1770, 1720, 1670, 1520, 1248, 1050.

NMR (DMSO-$d_6$, ppm)δ: 0.03 (s, $CH_3$), 0.96 (m, —$CH_2$—), 1.41 (s, $CH_3$), 3.20 (m, —$CH_2$—), 4.13 (m, —$CH_2$), 5.20–5.50 (m, $C_3$—H, $C_4$—H), 6.77 (s,

7.15–7.50 (m, arom H), 8.75 (s, NH), 9.18 (d, J=8 Hz, NH), 9.93 (br. s, NH).

The later eluate fractions give 0.222 g of sodium (3R, 4R)-4-[[(aminocarbonyl)methyl]thio]-3-[[[[[1-(2-trimethylsilylethoxycarbonyl)-1-methylethoxy]imino](2-tritylamino-4-thiazolyl)acetyl]amino]-2-azetidinone-1-sulfonate.

IR$\nu_{max}^{KBr}$ cm$^{-1}$: 3440–3380, 1765, 1725, 1670, 1520, 1275, 1248, 1045.

NMR (DMSO-$d_6$, ppm)δ: 0.03 (s, $CH_3$), 0.95 (m, —$CH_2$—), 1.74 (s, $CH_3$), 3.40 (ABq, J=11 Hz, —$CH_2$—), 4.14 (m, —$CH_2$—), 5.17–5.43 (m, $C_3$—H, $C_4$—H), 6.78 (s,

7.15–7.50 (m, arom H), 8.74 (s, NH), 9.23 (m, NH).

EXAMPLE 10

(1) To a solution of 0.30 g of sodium (3S, 4S)-4-azido-3-[[[[[1-(2-tritylmethylsilylethoxycarbonyl)-1-methylethoxy]imino](2-tritylamino-4-thiazolyl)acetyl]amino]-2-azetidinone-1-sulfonate obtained in Example 8-(1) in 3 ml of DMF is added 0.76 g of tetra-n-butylammonium fluoride trihydrate, and the reaction mixture is stirred at room temperature for 30 minutes. The DMF is distilled off under reduced pressure and the residue is treated with 20 ml of ethyl acetate and 20 ml of water. The organic layer is separated, concentrated under reduced pressure, and the residue is dissolved in 4 ml of methanol. To the solution is added 2.67 ml of 1N hydrochloric acid under ice-cooling, and the mixture is stirred at room temperature for 4 hours. After addition of 20 ml of methanol and 20 ml of Dowex 50W resin ($Na^+$-form), the mixture is stirred for one hour and then to the mixture is added 15 ml of Dowex 50W resin ($Na^+$-form), and the mixture is stirred for 2 hours. The resin is filtered off and the filtrate is concentrated under reduced pressure. The insoluble material is filtered off and the filtrate is chromatographed on a column of XAD-II resin to give 0.089 g of sodium (3S, 4S)-3-[[(2-amino-4-thiazolyl)[(1-carboxy-1-methylethoxyimino]acetyl]amino]-4-azido-2-azetidinone-1-sulfonate.

IR$\nu_{max}^{KBr}$ cm$^{-1}$: 3400, 2120, 1780, 1662, 1585, 1530, 1276, 1260, 1055.

NMR (DMSO-$d_6$, ppm)δ: 1.43 (s, $CH_3$), 1.46 (s, $CH_3$), 5.27 (dd, J=5,8 Hz, $C_3$—H), 5.56 (d, J=5 Hz, $C_4$—H), 6.74 (s,

7.14 (s, $NH_2$), 10.99 (d, J=8 Hz, NH).

(2) According to the same manner as described above sodium (3S, 4R)-3-[[(2-amino-4-thiazolyl)[(1-carboxy-1-methylethoxy)imino]acetyl]amino]-4-azido-2-azetidinone-1-sulfonate is obtained.

IR$\nu_{max}^{KBr}$ cm$^{-1}$: 3390, 2115, 1775, 1655, 1585, 1525, 1270, 1245, 1052.

NMR (DMSO-$d_6$, ppm)δ: 1.43 (s, $CH_3$), 4.61 (dd, J=2, 8 Hz, $C_3$—H), 5.18 (d, J=2 Hz, $C_4$—H), 6.76 (s,

7.14 (s, $NH_2$), 11.42 (d, J=8 Hz).

EXAMPLE 11

To a solution of 0.10 g of sodium (3S, 4S)-4-azido-3-[[[[[1-(2-trimethylsilylethoxycarbonyl)-1-methylethoxy]imino](2-tritylamino-4-thiazolyl)]acetyl]amino]-2-azetidinone-1-sulfonate obtained in Example 8-(1) in 15 ml of 50% aqueous methanol is added Dowex 50W resin ($H^+$-form) and stirred at room temperature for 8 hours. The methanol is distilled off under reduced pressure and the residual aqueous solution is chromatographed on a column of XAD-II resin to give 0.058 g of (3S, 4S)-3-[[(2-amino-4-thiazolyl)[[1-(2-trimethylsilylethoxycarbonyl)-1-methylethoxy]imino]acetyl]amino]-4-azido-2-azetidinone-1-sulfonic acid.

IR$\nu_{max}^{KBr}$ cm$^{-1}$: 3400–3300, 2115, 1777, 1722, 1680, 1530, 1275, 1250, 1045.

NMR (DMSO-$d_6$, ppm)δ: 0.05 (s, $CH_3$), 0.95 (t, J=8 Hz, —$CH_2$—), 4.15 (t, J=8 Hz, —$CH_2$—), 5.21 (dd, J=5, 8 Hz, $C_3$—H), 5.46 (d, J=5 Hz, $C_4$—H), 6.73 (s,

7.20 (s, $NH_2$), 9.10 (d, J=8 Hz, NH).

EXAMPLE 12

To a solution of 0.192 g of sodium (3R, 4R)-4-[[(aminocarbonyl)methyl]thio]-3-[[[[[1-(2-trimethylsilylethoxycarbonyl)-1-methylethoxy]imino](2-tritylamino-4-thiazolyl)acetyl]amino]-2-azetidinone-1-sulfonate obtained in Example 9 in 5 ml of DMF is added 0.207 g of tetra-n-butylammonium fluoride trihydrate and the mixture is stirred at room temperature for 30 minutes. The DMF is distilled off under reduced pressure and to the resulting residue are added 20 ml of ethyl acetate and 5 ml of tetrahydrofuran, and the mixture is washed with saturated aqueous sodium chloride. The aqueous layer is extracted with 10 ml of ethyl acetate and the combined organic layers are concentrated under reduced pressure. The residue is dissolved in 20 ml of methanol, followed by addition of 15 ml of Dowex 50W resin (Na-form), and is stirred for 3.5 hours. The resin is filtered off and the methanol is distilled off under reduced pressure. The insoluble material is filtered off and the filtrate is chromatographed on a column of XAD-II resin to give 0.074 g of (3R, 4R)-4-[[(aminocarbonyl)methyl]thio]-3-[[(2-amino-4-thiazolyl)[(1-carboxy-1-methylethoxy)imino]acetyl]amino]-2-azetidinone-1-sulfonic acid.

IR$\nu_{max}^{KBr}$ cm$^{-1}$: 3440–3300, 1770, 1660, 1280–1240, 1155, 1050.

NMR (DMSO-d$_6$, ppm)δ: 1.43 (s, CH$_3$), 1.45 (s, CH$_3$), 3.41 (ABq, J=13 Hz, —CH$_2$—), 5.27–5.55 (m, C$_3$—H, C$_4$—H), 6.82 (s,

7.05 (s, NH), 7.18 (s, NH$_2$), 7.46 (s, NH), 9.83 (d, J=8 Hz, NH).

According to the same manner as described above, the following compounds are obtained.

(2) (3R, 4R)-3-[[(2-Amino-4-thiazolyl)[(1-carboxy-1-methylethoxy)imino]acetyl]amino]-4-[[(sulfoaminocarbonyl)methyl]thio]-2-azetidinone-1-sulfonic acid IR$\nu_{max}^{KBr}$ cm$^{-1}$: 3300–3000, 1760, 1660, 1625, 1268–1220, 1160, 1045.

NMR (DMSO-d$_6$, ppm)δ: 1.49 (s, CH$_3$), 3.38 (ABq, J=16 Hz, —CH$_2$—), 5.26–5.50 (m, C$_3$—H, C$_4$—H), 7.16 (s,

9.58 (d, J=8 Hz, NH).

(3) (3S, 4S)-3-[[(2-Amino-4-thiazolyl)[(carboxy)methoxyimino]acetyl]amino]-4-azido-2-azetidinone-1-sulfonic acid IR$\nu_{max}^{KBr}$ cm$^{-1}$: 3280, 3110, 2115, 1771, 1670, 1635, 1275–1250, 1042.

NMR (DMSO-d$_6$, ppm)δ: 4.70 (s, —CH$_2$—), 5.20 (dd, J=5, 8 Hz, C$_3$—H), 5.54 (d, J=5 Hz, C$_4$—H), 7.07 (s,

9.56 (d, J=8 Hz, NH).

(4) (3S, 4R)-3-[[(2-Amino-4-thiazolyl)[(carboxy)methoxyimino]acetyl]amino]-4-azido-2-azetidinone-1-sulfonic acid IR$\nu_{max}^{KBr}$ cm$^{-1}$: 3300, 3120, 2120, 1778, 1660, 1630, 1250, 1045.

NMR (DMSO-d$_6$, ppm)δ: 4.56 (dd, J=2, 8 Hz, C$_3$—H), 4.70 (s, —CH$_2$—), 5.29 (d, J=2 Hz, C$_4$—H), 7.04 (s,

9.53 (d, J=8 Hz, NH).

EXAMPLE 13

To a solution of 0.64 g of (3R, 4S)-4-[[(acetylamino)ethyl]thio]-3-[(p-nitro-benzyloxy)carboxamido]-2-azetidinone obtained in Reference Example 19 in 2 ml of DMF is added 3 ml of a DMF solution containing 0.766 g of sulfuric anhydride-DMF complex under cooling at −70° C., and the reaction mixture is allowed to stand at 0° C. for 24 hours. The reaction mixture is further treated in the same manner as described in Example 1 to give 0.619 g of sodium (3R, 4S)-4-[[(acetylamino)ethyl]thio]-3-[(p-nitrobenzyloxy)carboxamido]-2-azetidinone-1-sulfonate.

IR$\nu_{max}^{KBr}$ cm$^{-1}$: 3300, 1763, 1720, 1650, 1510, 1341, 1270, 1230, 1040.

NMR (DMSO-d$_6$, ppm)δ: 1.80 (s, CH$_3$), 2.85, 3.26(m, —CH$_2$—), 4.35 (dd, J=3.9 Hz, C$_3$—H), 4.86 (d, J=3 Hz, C$_4$—H), 5.22 (s, —CH$_2$—), 7.62, 8.23 (d, J=9 Hz, arom H), 7.90, 8.9 (br. s, NH).

(2) To a solution of 0.103 g of sodium (3R, 4S)-4-[[(acetylamino)ethyl]thio]-3-[(p-nitrobenzyloxy)carboxamido]-2-acetidinone-1-sulfonate obtained above in 3 ml of DMF is added 0.15 g of 10% palladium carbon, and the reaction mixture is stirred vigorously in a hydrogen gas stream for an hour. The catalyst is filtered off, and 0.136 g of D(−)-α-(4-ethyl-2,3-dioxo-1-piperazinecarboxamido)phenylacetic acid and 0.088 g of dicyclohexylcarbodiimide are added to the filtrate, and the mixture is stirred at room temperature for 2 hours. The reaction mixture is further treated in the same manner as described in Example 1 to give 0.048 g of sodium (3R, 4S)-3-[D(−)-α-(4-ethyl-2,3-dioxo-1-piperazinecarboxamido)phenylacetamido]-4-[[(acetylamino)ethyl]thio]-2-azetidinone-1-sulfonate.

IR$\nu_{max}^{KBr}$ cm$^{-1}$: 3290, 1765, 1710, 1670, 1503, 1250, 1185, 1043.

NMR (DMSO-d$_6$, ppm)δ: 1.09 (t, J=7 Hz, CH$_3$), 1.78 (s, CH$_3$), 3.40 (q, J=7 Hz, —CH$_2$—), 4.57 (dd, J=3, 8 Hz, C$_3$—H), 4.70 (d, J=3 Hz, C$_4$—H), 5.43 (d, J=8 Hz,

—CH—, 9.32 (d, J=8 Hz, NH), 9.77 (d, J=8 Hz, NH).

(3) According to the same manner as described in (2) above, from sodium (3R, 4R)-4-[[(acetylamino)ethyl]thio]-3-[(p-nitrobenzyloxy)carboxamido]-2-azetidinone-1-sulfonate, sodium (3R, 4R)-3-[D(−)-α-(4-ethyl-2,3-dioxo-1-piperazinecarboxamido)phenylacetamido]-4-[[(acetylamino)ethyl]thio]-2-azetidinone-1-sulfonate is obtained.

IR$\nu_{max}^{KBr}$ cm$^{-1}$: 3280, 1768, 1712, 1670, 1505, 1272, 1243, 1042.

NMR (DMSO-d$_6$, ppm)δ: 1.08 (t, J=7 Hz, CH$_3$), 1.78 (s, CH$_3$), 3.40 (q, J=7 Hz, —CH$_2$—), 5.05 (d, J=5 Hz, C$_4$—H), 5.26 (dd, J=5, 8 Hz, C$_3$—H), 5.58 (d, J=8 Hz,

—CH—, 9.27 (d, J=8 Hz, NH), 9.79 (d, J=8 Hz, NH).

Example 14

To a solution of 0.446 g of (3R, 4RS)-4-[[(acetylamino)ethyl]thio]-3-tritylamino-2-azetidinone obtained in Reference Example 19 in 3 ml of DMF is added 2 ml of a DMF solution containing 0.191 g of sulfuric anhydride-pyridine complex, and the reaction mixture is allowed to stand at room temperature for 3 days. After addition of diethyl ether, the resulting oily product is separated and suspended in a mixture of methanol (5 ml) and water (3 ml), followed by addition of Dowex 50W resin (Na$^-$-form), and the mixture is stirred for an hour. The resin is filtered off and the methanol is distilled off. The residual aqueous solution is lyophilized to give 0.202 g of sodium (3R, 4RS)-3-amino-4-[[(acetylamino)ethyl]thio]-2-azetidinone-1-sulfonate. The NMR spectrum shows this product is a mixture of the (3R, 4R)- and (3R, 4S)-derivatives (about 2:1 w/w).

IR$\nu_{max}^{KBr}$ cm$^{-1}$: 3290, 1775, 1640, 1540, 1270, 1042, 748.

NMR (DMSO-d$_6$, ppm)δ: The chemical shifts assignable to the (3R, 4R)-derivative; 1.83(s, CH$_3$), 2.82, 3.27(m, —CH$_2$—), 4.77(d, J=6Hz, C$_4$—H), 5.17(d, J=6Hz, C$_3$—H), 7.95(br.s, NH). The chemical shifts assignable to the (3R, 4S)-derivative; 1.82(s, CH$_3$), 2.82, 3.27(m, —CH$_2$—), 4.30(d, J=8Hz, C$_4$—H), 4.94(d, J=3Hz, C$_3$—H), 7.95(br.s, NH).

(2) A solution of 0.150 g of the above (3R, 4RS)-derivative, 0.156 g of D(—)-α-(4-ethyl-2,3-dioxo-1-piperazinecarboxamido)phenylacetic acid and 0.101 g of dicyclohexylcarbodiimide in 2 ml of DMF is stirred at room temperature for 2 hours. The reaction mixture is further treated in the same manner as described in Example 1 to give (3R, 4S)- and (3R, 4R)-derivatives of sodium 3-[D(—)-α-(4-ethyl-2,3-dioxo-1-piperazinecarboxamido)phenylacetamido]-4-[[(acetylamino)ethyl]thio]-2-azetidinone-1-sulfonate.

Example 15

To a solution of 0.761 g of (3R, 4R)-4-[[(diphenylmethoxycarbonyl)methyl]thio]-3-[[[(2-chloroacetylamino-4-thiazolyl)methoxyimino]acetyl]amino]-2-azetidinone in 4 ml of DMF is added a solution of 0.579 g of sulfuric anhydride-DMF complex in 2.26 ml of DMF at −70° C. and the reaction mixture is allowed to stand at −4° C. for 24 hours. After addition of 0.299 g of pyridine, diethyl ether is added to the mixture and the resulting oily product is separated, washed with diethyl ether and dissolved in water. The aqueous solution is treated with Dowex 50W residue (Na$^+$-form) and chromatographed on a column of XAD-II resin to give 0.792 g of sodium (3R, 4R)-4-[[(diphenylmethoxycarbonyl)methyl]thio]-3-[[[(2-chloroacetylamino-4-thiazolyl)methoxyimino]acetyl]amino]-2-azetidinone-1-sulfonate.

IR$\nu_{max}^{KBr}$ cm$^{-1}$: 3280, 1789, 1723, 1660, 1540, 1250, 1148, 1042.

NMR (DMSO-d$_6$, ppm): 3.84(s, OCH$_3$), 3.94(ABq, J=16Hz, SCH$_2$), 4.39(s, —CH$_2$—), 5.38(d, J=5Hz, C$_4$—H), 5.44 (dd, J=5, 8Hz, C$_3$—H), 6.83(s,

7.2–7.6(m, arom H), 10.63(d, J=8Hz, NH).

(2) To a suspension of 0.410 g of sodium (3R, 4R)-4-[[(diphenylmethoxycarbonyl)methyl]thio]-3-]]](2-chloroacetylamino-4-thiazolyl)methoxyimino]acetyl]amino]-2-azetidinone-1-sulfonate obtained in (1) above in 10 ml of anisole, is added 4.5 ml of trifluoroacetic acid and the reaction mixture is stirred for 1.5 hours. The reaction mixture, is added 50 ml of diethyl ether and the resulting precipitate is collected and dissolved in aqueous sodium hydrogen carbonate (pH 7–8). The aqueous solution is chromatographed on an XAD-II column to give 0.219 g of disodium (3R, 4R)-4-[[(carboxylato)methyl]thio]-3-[[[(2-chloroacetylamino-4-thiazolyl)methoxyimino]acetyl]amino]-2-azetidinone-1-sulfonate.

IR$\nu_{max}^{KBr}$ cm$^{-1}$: 3400, 1769, 1670, 1591, 1550, 1260, 1045.

NMR (DMSO-d$_6$, ppm)δ: 3.41(br.s, SCH$_2$), 3.89(s, OCH$_3$), 5.12(d, J=5Hz, C$_4$—H), 5.36(dd, J=5, 8Hz, C$_3$—H), 7.53(s,

9.90(d, J=8Hz, NH).

Example 16

To a solution of 0.176 g of disodium (3R, 4R)-4-[[(carboxylato)methyl]thio]-3-[[[(2-chloroacetylamino-4-thiazolyl)methoxyimino]acetyl]amino]-2-azetidinone-1-sulfonate obtained above in 2 ml of water, is added 0.047 g of sodium monomethyldithiocarbamate with stirring under ice-cooling, and the reaction mixture is then stirred at room temperature for an hour. The insoluble material is filtered off and the filtrate is treated with Dowex 50W resin (H$^+$-form) and then chromatographed on an XAD-II column to give 0.066 g of (3R, 4R)-4-[[(carboxy)methyl]thio]-3-[[[(2-amino-4-thiazolyl)methoxyimino]acetyl]amino]-2-azetidinone-1-sulfonic acid.

Elemental analysis, for C$_{11}$H$_{13}$N$_5$O$_8$S$_3$.3H$_2$O Calcd.: C, 28.02; H, 3.21; N, 14.85; S, 20.40. Found: C, 28.00; H, 2.92; N, 14.76; S, 19.81.

IR$\nu_{max}^{KBr}$ cm$^{-1}$: 3295, 3150, 1779, 1730, 1660, 1635, 1270, 1242, 1045.

NMR (DMSO-d$_6$, ppm)δ: 3.65(ABq, J=16Hz, SH$_2$), 3.97(s, OCH$_3$), 5.32(d, J=5Hz, C$_4$—H), 5.37(dd, J=5, 8Hz, C$_3$—H), 7.10(s,

9.64(d, J=8Hz, NH).

Example 17

A mixture of (3R, 4R)-4-[[[2-(chlorocetylamino)carboxyl]ethyl]thio]-3-tritylamino-2-azetidinone (0.524 g) obtained in Reference example 13 and sulfuric anhydride-pyridine complex (0.192 g) in DMF (4 ml) is stirred for 3 days at room temperature. To the reaction mixture is added diethyl ether to separate an oily product, which is suspended in a mixture of methanol (5 ml)-water (3 ml). This suspended solution is stirred with Dowex 50W (Na$^+$-form) including a small amount of Dowex 50W (H$^+$-form) for 2 hours at room temperature. After removal of the resin and methanol, the resulting aqueous solution is lyophilized to give a powder (0.252 g).

A mixture of the obtained powder (0.252 g), [(2-chloroacetylamino-4-thiazolyl)methoxyimino]acetic acid (0.285 g) and DCC (0.222 g) in DMF (5 ml) is stirred for 2 hours at room temperature. The reaction mixture is further treated in the same manner as described in Example 1 to give sodium (3R, 4R)-4-[[[2-(chloroacetylamino)carboxy]ethyl]thio]-3-[[[(2-chloroacetylamino-4-thiazolyl)(methoxyimino)]acetyl]amino]-2-azetidinone-1-sulfonate (0.326 g).

IR$\nu_{max}^{KBr}$ cm$^{-1}$: 3450, 3250, 1775, 1675, 1645-1620, 1255, 1042.

NMR (DMSO-d$_6$, ppm)δ: 3.08(m, —CH$_2$—), 3.88(s, CH$_3$), 4.28(t, J=7Hz, —CH$_2$—), 4.33(s, —CH$_2$—), 4.45(s, —CH$_2$—), 5.25–5.50(m, C$_3$—H, C$_4$—H), 7.47(s,

9.52(d, J=8Hz, NH), 11.00(s, NH), 12.90(br.s, NH).

Example 18

(3S, 4S)-3-[[(2-amino-4-thiazolyl)[(carboxy)methoxyimino]acetyl]amino-4-azido-2-azetidinone-1-sulfonic acid is placed in a sterile 12 ml vial in an amount of 250 mg (potency). The vial is then stoppered under reduced pressure (50 mm Hg).

Example 19

4-[[(aminocarbonyl)methyl]thio]-3-[[(2-amino-4-thiazolyl)[(1-carboxy-1-methylethoxy)imino]acetyl]amino]-2-azetidinone-1-sulfonic acid (250 g) and cefotiam (250 g) are mixed under aspetic conditions, and the mixture is placed in sterile 17 ml vials in an amount of 250 mg (potency) per vial. The vials are then stoppered under reduced pressure (50 mm Hg).

What is claimed is:

1. A compound of the formula

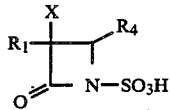

wherein
X is hydrogen or methoxy;
$R_1$ is
(1) amino;
(2) amino mono-substituted by an acyl group selected from the group consisting of
(A) a group of the formula $R_6$—CO— wherein $R_6$ is
(i) $C_{1-6}$ alkyl
(ii) phenyl which is unsubstituted or mono-substituted by
(1) $C_{1-3}$ alkyl, (2) $C_{1-3}$ alkoxy, (3) halogen, (4) nitro or (5) amino
(iii) a heterocyclic group selected from the group consisting of isoxazolyl, piperazinyl and imidazolinyl, said heterocyclic group being unsubstituted or mono- to tri-substituted by (1) $C_{1-3}$ alkyl, (2) $C_{1-3}$ alkoxy, (3) halogen, (4) nitro, (5) amino, (6) oxo, (7) thioxo, (8) phenyl or (9) phenyl mono-to-di-substituted by $C_{1-3}$ alkyl, $C_{1-3}$ alkoxy, halogen, nitro or amino,
(iv) benzoyl which is unsubstituted or mono-substituted by (1) $C_{1-3}$ alkyl, (2) $C_{1-3}$ alkoxy, (3) halogen, (4) nitro or (5) amino
(B) a group of the formula:

wherein $R_7$ is
(i) hydrogen,
(ii) an amino acid residue selected from the group consisting of seryl, threonyl, cysteinyl, cystyl, methionyl, lysyl, arginyl, phenylglycyl, tyrosyl, histidyl, tryptophyl or prolyl, the said amino acid residue being unsubstituted or mono-to di-substituted by amino, $C_{1-3}$ alkyl amino, amino protecting group, carbamoyl, methylcarbamoyl, sulfamoyl, benzyl, 4-ethyl-2,3-dioxo-1-piperazinecarbonyl or 4-ethyl-2,3-dioxo-1-piperazinecarbonylamino, with the proviso that (1) phenylglycyl which is unsubstituted or mono-substituted by amino, and (2) unsubstituted lysyl are excluded,
(iii) an amino-protecting group selected from the group consisting of phthaloyl, p-nitrobenzoyl, p-tert-butylbenzoyl, p-tert-butylbenzenesulfonyl, benzenesulfonyl, toluenesulfonyl, monochloroacetyl, dichloroacetyl, trichloroacetyl, trifluoroacetyl, maloyl, succinyl, benzyloxycarbonyl, p-nitrobenzyloxycarbonyl, p-methoxybenzyloxycarbonyl, 2-trimethylsilylethoxycarbonyl, methoxycarbonyl, trityl, 2-nitrophenylthio, benzylidene, 4-nitrobenzylidene, di- or trialkylsilyl, t-butyldimethylsilyl, t-butyldiphenylsilyl and p-nitrobenzyl,
(iv) a group of the formula $R_8$—$(CH_2)_{nl}$—CO— in which $R_8$ is
(a) hydrogen
(b) a heterocyclic group selected from the group consisting of 2-pyridyl, 3-pyridyl, 4-pyridyl, primidinyl, pyrazinyl, pyridazinyl, piperazinyl, pyrazolinyl, imidazolidinyl, thiazolyl, isothiazolyl, oxazolyl, isoxazolyl, pyrido[2,3-d]pyrimidinyl, benzopyranyl, 1,8-naphthylidinyl, 1,5-naphthylidinyl, 1,6-naphthylidinyl, 1,7-naphthylidinyl, 2,7-naphthylidinyl, 2,6-naphthylidinyl, quinonyl, thienopyridinyl, tetrazolyl, thiadiazolyl, oxadiazolyl, triazinyl, thienyl, pyrrolyl and furyl, said heterocyclic group being unsubstituted or mono- to tetra-substituted by (1) $C_{1-12}$ alkyl, (2) $C_{1-12}$ alkyl mono-substituted by phenyl, halogen, hydroxy or $C_{1-3}$ dialkylamino, (3) $C_{1-3}$ alkoxy, (4) hydroxy, (5) oxo, (6) thioxo, (7) formyl, (8) trifluoromethyl, (9) amino, (10) halogen, (11) $C_{1-3}$ alkylsulfonyl (12) 2,6-dichlorophenyl (13) coumarin-3-carbonyl, (14) 4-formyl-1-piperazinyl, (15) pyrroladoimino, (16) furanaldoimido, (17) 2-thiophenaldoimino, (18) 3-thiophenaldoimino, (19) mesyl, (20) amino-protecting group, (21) $C_{2-4}$ alkanoylamino or $C_{2-4}$ alkanoylamino mono-substituted by halogen
(c) phenyl which is unsubstituted or mono-substituted by $C_{1-3}$ alkyl, $C_{1-3}$ alkoxy, halogen, hydroxy, or amino,
(d) $C_{1-3}$ alkyl which is unsubstituted mono- to di-substituted by carboxyl, amino, ureido or carbamoyl,
(e) phenylthio which is unsubstituted or mono-substituted by $C_{1-3}$ alkyl, $C_{1-3}$ alkoxy, halogen, hydroxy or amino,
(f) $C_{1-3}$ alkylthio, (g) carboxyl, or (h) carbamoyl; nl is 0 or an integer of 1 to 4; and the group —$(CH_2)_{nl}$— is unsubstituted or mono- to di substituted by (1) amino or (2) a group of the formula —NH—$COR_8''''$ wherein $R_8''''$ is amino, piperazinyl or piperazinyl mono- to tri-substituted by $C_{1-3}$ alkyl, $C_{1-3}$ alkoxy, hydroxy, oxo, thioxo or halogen,
(v) a group of the formula

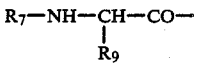

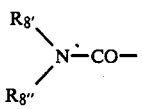

wherein R$_8'$ and R$_8''$ are independently (a) hydrogen, (b) C$_{1-3}$ alkyl, (c) C$_{1-3}$ alkyl-carbamoyl, (d) sulfo, (e) phenylcarbonyl or (f) phenylcarbonyl mono-substituted by C$_{1-3}$ alkyl, C$_{1-3}$ alkoxy, halogen, hydroxy, hydroxysulfonyloxy or benzyloxy; with the proviso that the case where R$_8'$ and R$_8''$ are both hydrogen is excluded, or (vi) a group of the formula R$_8'''$ —SO$_2$— wherein R$_8'''$ is C$_{1-6}$ alkyl or C$_{1-6}$ alkyl mono- to di-substituted by amino, carboxyl, benzyloxycarbonyl or protected amino, R$_9$ is (i) hydrogen, (ii) C$_{1-3}$ alkyl which is unsubstituted or mono-substituted by hydroxyl, formyloxy, phenyl, carbamoyl, methylcarbamoyl, methylthio, thienylacetamide, ethoxycarbonylmethylcarbamoyl, N-methyltetrazolylthio, halogen or sulfamoyl, (iii) phenyl which is unsubstituted or mono- to di-substituted by C$_{1-3}$ alkyl, C$_{1-3}$ alkoxy, halogen, hydroxy, hydroxysulfonyloxy, benzyloxy, benzoyloxy, trimethylsilyl or C$_{2-10}$ alkanoyamino, (iv) a heterocyclic group selected from the group consisting of thiazolyl, isothiazolyl, oxazolyl, isoxazolyl, thienyl, furyl, pyrrolyl, imidazolyl, pyrazinyl, pyrimidinyl, pyridazinyl, piperazinyl, triazinyl, tetrazolyl, thiadiazolyl and oxadiazolyl, said heterocyclic group being unsubstituted or mono-substituted by (1) C$_{1-3}$ alkyl, (2) C$_{1-3}$ alkoxy, (3) halogen, (4) hydroxy, (5) nitro, (6) hydroxysulfonyloxy (7) amino, (8) C$_{2-4}$ alkanoylamino or (9) C$_{2-4}$ alkanoylamino mono-substituted by halogen (v) cycloalkenyl selected from the group consisting of cyclohexenyl and cyclohexadienyl, or (vi) piperazinylcarbonylamino which is unsubstituted or mono- to tri-substituted by C$_{1-12}$ alkyl, C$_{1-3}$ alkoxy, oxo, thioxo or amino and which may have a C$_{1-3}$ alkylene chain between the piperazinyl and carbonylamino moieties;

(C) a group of the formula:

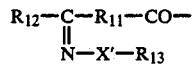

wherein X' is oxygen or sulfur, R$_{11}$ is a chemical bond or a group of the formula:

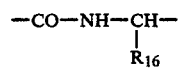

wherein

R$_{16}$ is (a) C$_{1-3}$ alkyl, (b) phenyl, (c) phenyl mono-substituted by C$_{1-3}$ alkyl, C$_{1-3}$ alkoxy, halogen, nitro, amino or C$_{2-10}$ alkanoyloxy, or (d) a heterocyclic group selected from the group consisting of thiazolyl, isothiazolyl, oxazolyl, isoxazolyl, thienyl, furyl, pyrrolyl, thiadiazolyl, oxadiazolyl, triazinyl, tetrazolyl, imidazolyl, pyrazinyl, pyrimidinyl, pyridazinyl and piperazinyl, said heterocyclic group being unsubstituted or mono-substituted by (1) C$_{1-3}$ alkyl, (2) C$_{1-3}$ alkoxy, (3) halogen, (4) hydroxyl, (5) amino, (6) C$_{2-4}$ alkanoylamino or (7) C$_{2-4}$ alkanoylamino mono-substituted by halogen; R$_{12}$ is (a) a heterocyclic group selected from the group consisting of 2-thiazolyl, 4-thiazolyl, 5-thiazolyl, 2-thienyl, 3-thienyl, 2-furyl, 3-furyl, 2-pyrrolyl and 3-pyrrolyl, said heterocyclic group being unsubstituted or mono- to di-substituted by C$_{1-3}$ alkyl, C$_{1-3}$ alkoxy, hydroxyl, mesyl, halogen, imino, amino, mesylamino, C$_{2-4}$ alkanoylamino or C$_{2-4}$ alkanoylamino mono-substituted by halogen, or (b) phenyl which is unsubstituted or mono-substituted by (1) C$_{1-3}$ alkyl (2) C$_{1-3}$ alkoxy, (3) halogen, (4) nitro, (5) amino, (6) hydroxyl (7) benzyloxy, (8) benzoyloxy, (9) C$_{2-10}$ alkanoyloxy, (10) γ-D-glutamyloxy or (11) 3-amino-3-carboxypropyloxy;

R$_{13}$ is (a) hydrogen, (b) phenyl which is unsubstituted or mono-substituted by C$_{1-3}$ alkyl, C$_{1-3}$ alkoxy or halogen, (c) C$_{2-4}$ alkanoyl (d) C$_{2-4}$ alkanoyl mono- to di-substituted by halogen, (e) C$_{1-3}$ alkyl which is unsubstituted or mono-substituted by carbamoyl or halogen, (f) a group of the formula —R$_{14}$—R$_{15}$ wherein R$_{14}$ is C$_{1-3}$ alkylene or C$_{2-3}$ alkenylene, and R$_{15}$ is carboxy, methyl ester of carboxyl, ethyl ester of carboxyl, propyl ester of carboxyl, t-butyl ester of carboxyl, p-nitrobenzyl ester of carboxyl, 2-trimethylsilylethyl ester of carboxyl, t-butyldiphenylsilyl ester of carboxyl, diphenylmethyl ester of carboxyl, or a heterocyclic group selected from the group consisting of morpholino, tetrazolyl and triazolyl, (D) a group of the formula:

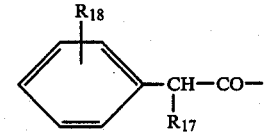

wherein

R$_{17}$ is (a) hydroxy, (b) hydroxysulfonyloxy, (c) carboxyl, (d) sulfamoyl, (e) sulfamoyl substituted by C$_{1-3}$ alkyl, (f) sulfo, (g) phenoxycarbonyl, (h) phenoxycarbonyl mono-substituted by C$_{1-3}$ alkyl or C$_{1-3}$ alkoxy, (i) benzyloxycarbonyl (j) formyloxy (k) phthalimido (l) azido or (m) halogen;

R$_{18}$ is (a) hydrogen, (b) C$_{1-3}$ alkyl, (c) C$_{1-3}$ alkoxy, (d) halogen, (e) azido, (f) nitro or (g) hydroxyl; and (E) a group of the formula:

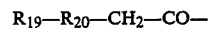

wherein

R$_{19}$ is (a) cyano, (b) phenyl, (c) phenyl mono-substituted by C$_{1-3}$ alkyl, C$_{1-3}$ alkoxy, halogen, nitro, amino, hydroxyl, aminomethyl or aminomethyl mono-substituted by carbamoyl, (2-oxo-3-benzylideneaminoimidazolidin-1-yl)carbonyl or (2-oxoimidazolidin-1-yl)carbonyl, (d) phenoxy, (e) phenoxy mono-substituted by C$_{1-3}$ alkyl, C$_{1-3}$ alkoxy, halogen, nitro, amino, hydroxy or aminomethyl, (f) C$_6$ alkyl (g) C$_{1-6}$ alkyl mono- to tri-substituted by halogen hydroxyl, cyano or trifluoromethyl, (h) alkenyl selected from the group consisting of vinyl and propenyl, said alkenyl being unsubstituted or mono-substituted by carboxyl or cyano, or (i) a heterocyclic group selected from the group consisting of 2-thienyl, benzothienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl and 1,4-oxathiinyl, said heterocyclic group being unsubstituted or mono- to tri-substituted by $C_{1-3}$ alkyl, $C_{1-3}$ alkoxy, halogen, nitro, hydroxyl, amino, amino-protective group, carboxyl, oxo, $C_{2-4}$ alkanoylamino, $C_{2-4}$ alkanoylamino mono-substituted by halogen or $C_{2-4}$ alkanoyl;

$R_{20}$ is a chemical bond or —S—; or (3) amino protected by an amino-protecting group selected from the group consisting of phthaloyl, p-tert-butylbenzoyl, p-tert-butylbenzenesulfonyl, benzenesulfonyl, toluenesulfonyl, formyl, monochloroacetyl, dichloroacetyl, trichloroacetyl, methanesulfonyl, ethanesulfonyl, trifluoroacetyl, maloyl, succinyl, benzyloxycarbonyl, p-nitrobenzyloxycarbonyl, p-methoxybenzyloxycarbonyl, 2-trimethylsilylethoxycarbonyl, methoxycarbonyl, trityl, 2-nitrophenylthio, benzylidene, 4-nitrobenzylidene, di- or trialkylsilyl, t-butyldimethylsilyl and t-butyldiphenylsilyl;

$R_4$ is a group of the formula —S—Y—Z where Y is an alkylene group of 1 to 3 carbon atoms or an alkenylene group of 2 to 3 carbon atoms, and Z is ① an alkanoyloxy group of 2 to 4 carbon atoms, ② a sulfocarbamoyl group, ③ an optionally protected carbamoyloxy group, ④ a sulfocarbamoyloxy group, or ⑤ an amino group which may be mono-substituted by a sulfo group, an alkanoyl group of 2 to 4 carbon atoms, a benzyloxycarbonyl group or a phenethyloxycarbonyl group or a pharmaceutically acceptable salt or pharmaceutically acceptable ester thereof.

2. A pharmaceutical composition which comprises an antibacterially effective amount of a compound or pharmaceutically acceptable salt or pharmaceutically acceptable ester thereof as defined in claim 1 as an effective ingredient, and a pharmaceutically acceptable carrier therefor.

3. A compound as claimed in claim 1, wherein $R_4$ is a group of the formula, —S—Y—Z where Y is an alkylene group of 1 to 3 carbon atoms, Z is an alkanoyloxy group of 2 to 4 carbon atoms, an optionally protected carbamoyloxy group, or an amino group which may be mono-substituted by a benzyloxy carbonyl group.

* * * * *